United States Patent [19]

Selsted et al.

[11] Patent Number: 5,844,072
[45] Date of Patent: Dec. 1, 1998

[54] ANTIBIOTIC CRYPTDIN PEPTIDES AND METHODS OF THEIR USE

[75] Inventors: Michael E. Selsted, Irvine, Calif.; Andre J. Ouellette, Lynn, Mass.

[73] Assignee: University of California, Alameda, Calif.

[21] Appl. No.: 342,268

[22] Filed: Nov. 18, 1994

Related U.S. Application Data

[63] Continuation-in-part of Ser. No. 930,649, Aug. 14, 1992, Pat. No. 5,422,424, which is a continuation-in-part of Ser. No. 889,020, May 26, 1992, abandoned.

[51] Int. Cl.$^6$ .............................. C07K 5/00; C07H 21/02; A01N 37/18; A01N 25/26
[52] U.S. Cl. ..................... 530/300; 536/23.1; 536/24.3; 536/24.33; 424/418; 424/409; 424/426; 514/2; 635/6; 635/91.2
[58] Field of Search ...................... 435/6, 91.2; 536/23.1, 536/24.3, 24.33; 530/300, 350; 514/2; 424/418, 409, 426

[56] References Cited

PUBLICATIONS

Talmadge, Advanced Drug Delivery Reviews, 10: 247–299, 1993.
Gantz et al. Eur. J. of Haemotol 44:1–8, 1990.

*Primary Examiner*—W. Gary Jones
*Assistant Examiner*—Dianne Rees
*Attorney, Agent, or Firm*—Campbell & Flores LLP

[57] ABSTRACT

The present invention provides substantially purified cryptdin peptides having a consensus amino acid sequence:

$X_1$-C-$X_2$-C-R-$X_3$-C-$X_4$-E-$X_5$-C-$X_6$-C-C-$X_7$ or having a consensus amino acid sequence:

$X_1$-L-$X_2$-C-Y-C-R-$X_3$-C-K-$X_4$-E-$X_5$-G-T-C-$X_6$-C-C-$X_7$ wherein $X_1$ to $X_7$ each independently is 0 to 10 amino acids. The invention also provides cryptdin analogs, which are devoid of one or more amino acids N-terminal to the first cysteine. In addition, the invention provides nucleic acid molecules encoding cryptdin peptides. The invention further provides methods for detecting inflammatory pathologies in a subject and for treating an inflammatory pathology in a subject by administering a pharmaceutical composition containing a cryptdin peptide.

20 Claims, 27 Drawing Sheets

FIG. 9A

```
        <---------------- Exon 1 ----------------><------------------ Exon 2 ------------------>
        <--SIGNAL PEPTIDE--><------- PROPIECE --------------->  <------  CRYPTDIN  ------------->
        1                                         58                                          93
Cryp01  MKTLVLLSAL VLLAFQVQAD PIQNTDEETK TEEQPGEDDQ AVSVSFGDPE GTSLQEES LRDLVCYCRS RGCKGRERMN GTCRKGHLLY TLCCR
Cryp02  MKTLILLSAL VLLAFQVQAD PIQNTDEETK TEKQPGEEDQ AVSVSFGDPE GSSLQEES LRDLVCYCRT RGCKRRERMN GTCRKGHLMY TLCCR
Cryp03  MKTLVLLSAL VLLAFQVQAD PIQNTDEETK TEEQPGEDDQ AVSVSFGDPE GSSLQEES LRDLVCYCRK RGCKRRERMN GTCRKGHLMY TLCCR
Cryp04  ...LVLLSAL VLLAFQVQAD PIQNTDEETK TEEQPGEEDQ AVSISFGGQE LRGLLCYCRK GHCKRGERVR GTC**G*IRF LYCCPRR
Cryp05  MKTFVLLSAL VLLAFQVQAD PIHKTDEETN TEEQPGEEDQ AVSISFGGQE GSALHEKS LSKKLICYRI RGCKRRERVF GTCRNLFLTF VFCCS
Cryp06  MKTLVLLSAL VLLAFQVQAD PIQNTDEETK TEEQPGEEDQ AVSVSFGDPE GSALHEE LSKKLICYRI RGCKRRERVF GTCRNLFLTF VFCCS
Cryp07  MKTLILLSAL VLLAFQVQAD PIQNTDEETK TEEQPGEDDQ AVSVSFGDPE GSSLQEES LRDLVCYCRA RGCKGRERMN GTCRKGHLLY MLCCR
Cryp08  MKTLVLLSAL VLLAFQVQAD PIQNTDEETK TEEQPGEDDQ AVSVSFGDPE GSSLQEES LRDLVCYCRT RGCKRREHMN GTCRKGHLMY TLCCR
Cryp09  ..LAFQVQAD PIQNTDEETK TEEQPGEDDQ AVSVSFGDPE GSSLQEES LRDLVCYCRK RGCKRREHMN GTCRKGHLMY TLCCR
Cryp10  .KTLVLLSAL VLLAFQVQAD PIQNTDEETK TEEQPGEDDQ AVSVSFGDPE GSSLQEES LRDLVCYCRK RGCKGRERMN GTCRKGHLLY TLCCR
Cryp11  ......AL VLLAFQVQAD PIQNTDEETK TEEQPGEEDQ AVSVSFGDPE GTSLQEES LRDLVCYCRS RGCKGRERMN GTCRKGHLLY MLCCR
Cryp12  MKTLILLSAL VLLAFQVQAD PIQNTDEETK TEEQPGEEDQ AVSVSFGDPE GTSLQEES LRDLVCYCRA RGCKGRERMN GTCRKGHLMY TLCCR
Cryp13  MKTLVLLSAL VLLAFQVQAD PIQNTDEETK TEEQPGEEDQ AVSVSFGDPE GSSLQEES LRDLVCYCRK RGCKRREHMN GTCRRGHLMY TLCCR
Cryp14  ......AL VLLAFQVQAD PIQNTDEETK TEEQPGEDDQ AVSVSFGDPE GSSLQEES LRDLVCYCRT RGCKRRERMN GTCRKGHLMH TLCCR
Cryp15  MKTLVLLSAL VLLAFQVQAD PIQNTDEETK TEEQPGEEDQ AVSVSFGDPE GSSLQEES LRDLVCYCRK RGCKRREHIN GTCRKGHLLY MLCCR
Cryp16  MKTLILLSAL VLLAFQVQAD PIQNTDEETK TEEQPGEEDQ AVSVSFGDPE GTSLQEES LRDLVCYCRS RGCKGRERMN GTCRKGHLMY TLCCR
Cryp17  ........LLAFQVQAD PIQNTDEETK TEEQPGEEDQ AVSVSFGDPE GTSLQEES LRDLVCYCRK RGCKRREHMN GTCRKGHLLY TLCCR
```

| | Base | -40 | -30 | -20 | -10 | +1 | 10 | 20 | 30 | 40 | 50 |
|---|---|---|---|---|---|---|---|---|---|---|---|
| Cryptdin-1 Codon: | | | | | | | MetLysThrLeuValLeuLeuSerAlaLeuValLeuLeuAlaPheGlnValGlnAla 1 10 | | | | |
| Cryp01 | | acacattgagctcctgctcaccaatcctccaggtgactcccagcc | | | | ATGAAGACACTAGTCCTCTCTGCCCTTGTCCTGCTGGCCTTCCAGGTCCAGG | | | | | |
| Cryp01 | | ......T.A...C.G.............................. | | | | .............................T........................ | | | | | |
| Cryp02 | | ......C.A..CG.A.............................. | | | | ..................A.............C...................... | | | | | |
| Cryp03 | | ......T.G...C.G.............................. | | | | .................................C...................... | | | | | |
| Cryp04 | | .............................................. | | | | .................................C...................... | | | | | |
| Cryp05 | | ......T.G...C.G..........T................C.. | | | | .................TT............T....................... | | | | | |
| Cryp06 | | ......C.A...G.A.............................. | | | | ..................A.............C...................... | | | | | |
| Cryp07 | | ......C.A...G.A.............................. | | | | ..................A.............C...................... | | | | | |
| Cryp08 | | .............................................. | | | | ......................................................... | | | | | |
| Cryp09 | | .............................................. | | | | .................................C...................... | | | | | |
| Cryp10 | | .............................................. | | | | .................................C...................... | | | | | |
| Cryp11 | | .............................................. | | | | .................................C...................... | | | | | |
| Cryp12 | | ......T.G...C.G.............................. | | | | .................................C...................... | | | | | |
| Cryp13 | | .............................................. | | | | .................................T...................... | | | | | |
| Cryp14 | | .............................................. | | | | .................................C...................... | | | | | |
| Cryp15 | | ............................CA.............. | | | | .................................T...................... | | | | | |
| Cryp16 | | .............................................. | | | | ..................A.............C...................... | | | | | |
| Cryp17 | | .............................................. | | | | ......................................................... | | | | | |
| Consensus | | acaca-tg-gct-ct-ctcaccaatcctccaggtgactcccagcc | | | | ATGAAGACACTAGTCCTCCTCTCTGCCCT-GTCCTGCTGGCCTTCCAGGTCCAGG | | | | | |

FIG. 10(b)

| Cryptdin-1 | AspProIleGlnAsnThrAspGluGluThrLysThrGluGluGlnProGlyGluAspAspGlnAlaValSerValSerPheGlyAspProGluGlyThr |
|---|---|
| Codon: | 20　　　　　　　　　　　30　　　　　　　　　　　40　　　　　　　　　　　50 |
| Cryp01 | CTGATCCTATCCAAAACACAGATGAAGAGACTAAAACTGAGGAGCAGCCAGGGGAAGACGACCAGGCCGTATCTGTCTCCTTTGGAGACCCAGAAGGCAC |
| Base | 60　　　　　　70　　　　　　80　　　　　　90　　　　　100　　　　　110　　　　　120　　　　　130　　　　　140　　　　　150 |

| | | | | | | | | | | |
|---|---|---|---|---|---|---|---|---|---|---|
| Cryp01 | ................................................................................................C.........................................A |
| Cryp02 | ..........T.....................................................................G.................................................T |
| Cryp03 | ................................................................................C..........................................................T |
| Cryp04 | ..........T....................................................................G............A...C..........G..A.....GT |
| Cryp05 | ........C.A....................T...............................................G..............A..................G..A.....GT |
| Cryp06 | ..........T.....................................................................G.............................................A |
| Cryp07 | ................................................................................C.............................................T |
| Cryp08 | ................................................................................C.............................................T |
| Cryp09 | ................................................................................G.............................................T |
| Cryp10 | ................................................................................C.............................................T |
| Cryp11 | ................................................................................G.............................................A |
| Cryp12 | ................................................................................G...........C.A...C........................A |
| Cryp13 | .............................................................A................G.............................................T |
| Cryp14 | ................................................................................G.............................................T |
| Cryp15 | .............................................................A................C...........C.A...C..........................A |
| Cryp16 | .............................................................A................G...........C.A...C..........................A |
| Cryp17 | ..........T.....................................................................G.............................................A |
| Consensus | CTGATCCTATCCAAAACACAGATGAAGAGACTAAAACTGAGGAGCAGCCAGGGGAAGA-GACCAGGCCAGCAGCCAGGGGAAGA-GACCAGGCTGTGTCTGTCTCTTTTGGAGACCCAGAAGGC-C |

FIG. 10(c)

| Cryptdin-1 | SerLeuGlnGluGluSerLeuArgAspLeuValCysTyrCysArgSerArgGlyCysLysLysGlyArgGluArgMetAsnGlyThrCysArgLysGlyHis |
|---|---|
| Codon: | 60 · · · · · · · · · · · · 70 · · · · · · · · · · · · 80 |
| Cryp01 | TTCTCTTCAAGAGGAATCGTTGAGAGATCTGGTATGCTATTGTAGATCAAGAGGCTGCAAAGGAAGAGAACGCATGAATGGGACCTGCAGAAAGGGTCAT |
| Base | 160     170     180     190     200     210     220     230     240     250 |

| | |
|---|---|
| Cryp01 | ........................................................A....................... |
| Cryp02 | .......................................TC................G..G........................ |
| Cryp03 | .......................................TC................A..G........................ |
| Cryp04 | .G......T..AA....T......G.T..T..........AA.G..CA......A..G......GAG.TCG......T..TG...TAC.ATT. |
| Cryp05 | .G.......T......T..CA.A.A.G...A.........AT................A..G.G.TTT................TCT.TT. |
| Cryp06 | ...................A.....T..............GC................G..G........................ |
| Cryp07 | .........................................AC................A..A........................ |
| Cryp08 | .........................................AA................A..A........................ |
| Cryp09 | .........................................AA................A..A........................ |
| Cryp10 | .........................................AA................G..G.........A............... |
| Cryp11 | .........................................TC................G..G.........A............... |
| Cryp12 | ..........C..............................GC................G..G........................ |
| Cryp13 | .........................................AA................A..A.....................G.. |
| Cryp14 | .........................................AC................A..A........................ |
| Cryp15 | .........................................AA................A..A...A..................... |
| Cryp16 | .........................................TC................G..G........................ |
| Cryp17 | .......T.................................AA................A..A........................ |
| Consensus | TTCTCTTCAAGAGGAATCGTTGAGAGATCTGGTATGCTATTGTAGA--AAGAGGCTGCAAA-GAAGAGAAC-CATGAATGGGACCTGCAGAAAGGGTCAT |

```
Cryp01    cataaaattgttcgcaatatgc(A)n
Base               360         370
Cryp01    ....................................
Cryp02    .............C.T....................
Cryp03    ....................................
Cryp04    A...-GT...CAATATGC.
Cryp05    A.TA..T.GT.CGCA.TATG.
Cryp06    .......C............................
Cryp07    ....................................
Cryp08    ....................................
Cryp09    ....................................
Cryp10    ....................................
Cryp11    ........C...........................
Cryp12    ....................................
Cryp13    ....................................
Cryp14    ........................A...........
Cryp15    ....................................
Cryp16    .............C.T....................
Cryp17    ....................................
Consensus cataaaattgttcgcaatatgc
```

FIG. 11(a)

| Nucleotide | -60 | -50 | -40 | -30 | -20 | -10 | CODON 1 2 3 4 5 6 7 8 9 10 20 |
|---|---|---|---|---|---|---|---|
| | tataaatgcaxxctggxtxxtcactxtccACACATTGXGCTCCTGCTCACCAATCCTCCAGGTGACTCCCAGCCATGAAGACACTGTCCTCTCTGC | | | | | | |
| Cryp1 | .........gg....a.at.....g......A...............................................A............ | | | | | | |
| Cryp2 | .........ga....c.cc....C...............CA.............................C...T..........T....... | | | | | | |
| Cryp3 | .........gg....a.at....c.......G................................................A............ | | | | | | |
| Cryp5 | .........agt...c.ac....c.......G.....................T......C..............T.T............... | | | | | | |
| Cryp6 | .........gg....a.at....c......C.A..G.A.............................................AA........ | | | | | | |
| Cryp1 | ac.tg.g.gtaa.a.cc.tc.caat......A...................................................A.......... | | | | | | |

| CODON | 30 | 40 | 50 | 60 | 70 | 80 | 90 | 100 | 110 | 120 |
|---|---|---|---|---|---|---|---|---|---|---|
| | 10 11 12 13 14 15 16 17 18 19 20 21 22 23 24 25 26 27 28 29 30 31 32 33 34 35 36 37 38 39 40 41 42 | | | | | | | | | |
| | CCTGTCCTGCTGGCCTTCCAGGTCCAGGTCTGATCCTATCCAAAATACAGATGAAGACTAAAACTGAAGAGCAGCAGGTGAAGATGACCAGGCTGTI | | | | | | | | | |
| Cryp1 | ....T...................................................C...........................A....G.....C..A | | | | | | | | | |
| Cryp2 | ....T.....A...T.....T......................................C...........T............A....T...G.........G | | | | | | | | | |
| Cryp3 | ....C......................................................C.................................G....C......G | | | | | | | | | |
| Cryp5 | ....T........................................................C..A..........T............G....G.........G | | | | | | | | | |
| Cryp6 | ....C.........................................................T..............................G....G..A.......G | | | | | | | | | |
| Cryp1 | ....T.C........................A............................C................................GA...A......T | | | | | | | | | |

RAT CRYPTIN 1 cDNA SEQUENCE

```
10         20         30         40         50
1234567890 1234567890 1234567890 1234567890 1234567890
ACACTGGTCT CCAGCTCACC AATCCTCCAG GTGACTTCCA GCCATGAAGA    50
CTCTTGTCCT CCTCTCTGCC CTTGTCCTGC TGGCATTCCA GGTCCAGGCT   100
GATCCCATTC AAGAGGCAGA AGAAGAGACT AAAACTGAGG AGCAGCCAGC   150
AGATGAGGAC CAGGATGTGT CTGTCTCCTT TGAAGGCCCA GAACCCTCTG   200
CTCTTCAAAA TTTAGAGATA GGATGGCCAT TAAAGCAGTG CCATTGCCGA   250
AAGTTCTGCA GACCTTATGA AAAGGCCGAG GGGTCCTGTC GTCCAGGTCT   300
ATTTATAAAA CGCAAAATCT GCTGCATACA ACAATGGACA CCAGGGAGGA   350
CATAACCACG TGAACTGGGA CCTCACAATC TGTCATTCTT GGGCTTCAAC   400
TCGACTGCTT TTCCTTCTCC AATAAACCCC TTGCAGACAA AAAAA        445
```

FIG. 14B

RAT CRYPTIN 2 cDNA SEQUENCE

```
10         20         30         40         50
1234567890 1234567890 1234567890 1234567890 1234567890
ACACTGGTCT CCAGCTCACC AATCCTCCAG GTGACTTCCA GCCATGAAGA    50
CTCTTGTCCT CCTCTCTGCC CTTGTCCTGG TGGCCTACCA GGTCCAGGCT   100
GATCCCATTC AAGGGGCAGA AGAAGAGACT AAAACTGAAG AGCAACCATC   150
AGATGAGGAC CAGGATGTGT CTGTCTCCTT TGAAGGCCCA GAAGCCTCTG   200
CTCTTCAAGA TTTTGAGATA GGAAGGCCAG TGAGGAGGTG CCGTTGCAGA   250
GCAAACTGCG GACCTAAAGA ATATGCCACT GCGTTCTGTG CTCAAGGTCC   300
ATTTAAACAG TTCAAATTCT GCTGCACATG AACATGGATC CCAAGTCTGA   350
GATAACCACG TGCTCTGGGA CCTCACAATC TGTCATTATT GTGCTTGACC   400
TCAACTGCTT TTCCTTCTCC AATAAACTCC TGGCAGACAA AAAAA        445
```

FIG. 14C

RAT CRYPTIN 3 cDNA SEQUENCE

```
10         20         30         40         50
1234567890 1234567890 1234567890 1234567890 1234567890
ACACTGGTCT CCAGCTCACC AATCCTCCAG GTGACTTCCA GCCATGAAGA    50
CTCTTGTCCT CCTCTCTGCC CTTGTCCTGC TGGCATTCCA GATCCAGGCT   100
GATCCCATTC AAGAGGCAGA AGAAGAGACT AAAACTGAGG AGCAGCCAGC   150
AGATGAGGAC CAGGATGTGT CTGTCTCCTT TGAAGGCCCA GAACCCTCTG   200
CTCTTCAAAA TTTAGAGATC AGATGGCCAT GGAAGAGGTG CCATTGCAGA   250
AGTTCTGCA GACCTTATGA AAATCGGACT TCGTTCTGTG CTCAAGGTCT    300
ATTTAAACAA CACAAATTCT GCTGCCTAGA AACATGGCCC CCAAGGATGA   350
AATAACCACG TGCTCTGGGA CCTCACAATC TGTCATCATT GTGCTTGGCC   400
TCAACTTCTT TTCCTTCTCC AATAAACTCC TTGCAGACAA AAAAA        445
```

FIG. 15A(1)

RAT CRYPTIN 1 GENOMIC SEQUENCE

| 10 | 20 | 30 | 40 | 50 | |
|---|---|---|---|---|---|
| 1234567890 | 1234567890 | 1234567890 | 1234567890 | 1234567890 | |
| CCTGAGACCA | ACTCTGTGAT | AATCAGAAAA | GTCAATAATG | TGTCTGAAAT | 50 |
| GTAAGGTGTG | CTTCTTGACT | GATAGTTCTA | AGCCTACAGA | GAGATTCATG | 100 |
| TGGTCATATC | CCATTTAACA | ATGATATATA | TGTTAAATAT | ATAAAGATAT | 150 |
| ATGTATGTTC | AGTATGTATG | TTCAATATGT | ATGTAAATAA | TATTCTTGCT | 200 |
| GCTTCACTAG | CTTTTACACA | GAGCTGTAAG | TAAAAACATT | GTAGCCAATG | 250 |
| AATAGTATTT | ATTAACATGT | AAATAGGAGC | TGGCACCTGT | GACAGTGGGA | 300 |
| CTCCATACAC | TGACTGTAAA | CAACAGGATG | CTCTGGACCT | TTTGCTGTGT | 350 |
| GTGTGGTGAG | AGACATGGGA | TAAACACAGA | CTGAAGAGTG | TTCCTGAATG | 400 |
| ACATGGCGGC | ACTTCTCGAG | ACCGGGTAGC | AGCTTCTGAG | CCTCTCTACA | 450 |
| TTGTGGATGT | CCTTTCCTGT | AGGTCAGGTC | TCATTGTCTA | AAAGTAAAAG | 500 |
| CATTGCAGCA | TCTCAGACCT | GGGAAACACC | CCATGGCTTG | AGGGTCCTGA | 550 |
| GCATGAAGAG | CCACCTGGAG | CTCACTCTTG | GCAGATGTGT | TCCATGACTT | 600 |
| TGGCTTCTTC | AGAACAACCC | ACTACAGCTT | CACTCTGACA | AATCCTAGAA | 650 |
| ACTTGAACTC | AATTCACTAG | AGGGCACCAT | AAAGCCATCA | TACCTTATAA | 700 |
| TGGCCCCAAA | GGAGGTGATT | CACAAAGTTT | GCCTTGATGA | GGACAATTGC | 750 |
| TAATACACAA | AAACTTGCAA | AAAAAAATTG | AGTGTCCAGT | CCACCTGGTC | 800 |
| AAGGACTGGT | CCCGGATCCA | CAGTTTCTGA | GAATAGCAGG | CTCTAACTTG | 850 |
| AAAACACAAA | AATTGTTTGT | TCTATGAGCT | CATTAAATTA | GGCAGTGTTC | 900 |
| AGCTATTTTC | TTTCCTGACC | ACTGAGAGGT | AAATACTCAA | GCAGATGGGA | 950 |
| AACAGGGGAG | GACAGTAAAG | CCTGTTCATC | ATTATCAGTG | GGAGTGTGCA | 1000 |
| TGAGGGGAGG | GGTGTCAGTG | AACACACAGA | GCATCAGGAA | GGAAGCCTTG | 1050 |
| AGGACAGAGG | AACATCAAAG | GGATCCTGAG | GACAACAGCT | GGGAGCAGTT | 1100 |
| GCCATCAATG | AGTGCCTTCT | CTAAGTATGG | GGCATGTTCT | TTGCCCTATA | 1150 |
| AATGCAGGCT | GGCTTCTCTC | TCCACACACT | GGTCTCCAGC | TCACCAATCC | 1200 |
| TCCAGGTGAC | TTCCAGCCAT | GAAGACTCTT | GTCCTCCTCT | CTGCCCTTGT | 1250 |
| CCTGCTGGCA | TTCCAGGTCC | AGGCTGATCC | CATTCAAGAG | GCAGAAGAAG | 1300 |
| AGACTAAAAC | TGAGGAGCAG | CCAGCAGATG | AGGACCAGGA | TGTGTCTGTC | 1350 |
| TCCTTTGAAG | GCCCAGAACC | CTCTGCTCTT | CAAAATTTAG | GTGCGTGCTT | 1400 |
| GTGCACAGAA | TGATGGAGGC | TTGGAGTCTC | CTGATGGAGG | GTTGTAGATT | 1450 |
| AGCCCTGGAG | TCCTGTCAAG | GACAGTCTGG | TTCAGGTAGC | TGTCTACTGA | 1500 |
| TCCTTTCAGA | ACTTCCCTGT | CTTATTCATA | GAAATAACAG | TGAGAGACAA | 1550 |
| GCCATTGGGC | TTGACTTTTT | CCTTTTAAGA | TTTCGGTCTA | ACAATTTATC | 1600 |
| TGTGAAAAAC | CTTTAAAATA | TAAAACATAT | TGATTAGTTC | TTTAAACCTG | 1650 |
| AGTGATAATT | TTCTTACAGG | AAGAAATATC | CGTTTTACCC | TAAAAATTAG | 1700 |
| ATTGGTACCC | AAATGCCAGT | GTATGAAGGT | GTTGGGTCAA | GAAAACACAA | 1750 |
| AAAAACTGTT | AGAATATGGT | GTAGATGAAA | ATTCCTATAT | GTGATTAACA | 1800 |
| CTTGTTAAAC | ATCTTATCTC | CATGTGTTTG | GGGTTGATCA | CTGTGCTGGC | 1850 |
| TGTGATGTCA | CCCACACAGC | AAACCTACTC | TCTACCATGC | ACAGGACATC | 1900 |

FIG. 15A(2)

RAT CRYPTIN 1 GENOMIC SEQUENCE

|  10        |  20        |  30        |  40        |  50        |      |
|------------|------------|------------|------------|------------|------|
| 1234567890 | 1234567890 | 1234567890 | 1234567890 | 1234567890 |      |
| TTCATGGGGT | AGTTCACTGT | TACACACTAC | TGGCCTCCTT | ACTTCATGCC | 1950 |
| TGATGCTTTC | TTGTTTCCTC | AGAGATAGGA | TGGCCATTAA | AGCAGTGCCA | 2000 |
| TTGCCGAAAG | TTCTGCAGAC | CTTATGAAAA | GGCCGAGGGG | TCCTGTCGTC | 2050 |
| CAGGTCTATT | TATAAAACGC | AAAATCTGCT | GCATACAACA | ATGGACACCA | 2100 |
| GGGAGGACAT | AACCACGTGA | ACTGGGACCT | CACAATCTGT | CATTCTTGGG | 2150 |
| CTTCAACTCG | ACTGCTTTTC | CTTCTCCAAT | AAACCCCTTG | CAGACAAATA | 2200 |
| ACCTGTTTAT | GTTTTTTTGA | TGCTTTCTAT | GTGGCGTAGA | CAGGACTCTC | 2250 |
| CTGAGCCATG | TAGCAAAATC | TTCAGTGAAT | CCTTTGTAAA | AGAAGTCTTG | 2300 |
| GTCACATTTC | AGCAGTCATA | TCAAGGATGA | GCAGGAGGTT | AGATCCAAAG | 2350 |
| AGACAAGATG | GTCTGCGCCA | GCTGCTTCTG | TGTCTATCAA | GTCTTCTGTC | 2400 |
| CTTTAGATTA | GAGTCACCCT | CAAAAATTAG | TTCCAGATTT | TCATGTTCTA | 2450 |
| TTTTTTC    |            |            |            |            | 2457 |

FIG. 15B(1)

RAT CRYPTIN 2 GENOMIC SEQUENCE

| 10 | 20 | 30 | 40 | 50 | |
|---|---|---|---|---|---|
| 1234567890 | 1234567890 | 1234567890 | 1234567890 | 1234567890 | |
| TATTACGAAT | TCGAGCTCGG | TACCGGTATA | TGAAGAGCGA | CCACTGCCAG | 50 |
| GACGAAAGTG | CAATGCGGCA | TACCTCAGTG | GCGTGGAGTG | CAGGTATACA | 100 |
| GATTAATCCG | GCAGCGTCCG | TCGTTGTTGA | TATTGCTTAT | GAAGGCTCCG | 150 |
| GCAGTGGCGA | CTGGCGTACT | GACGGATTCA | TCGTTGGGGT | CGGTTATAAA | 200 |
| TTCTGATTAG | CCAGGTAACA | CAGTGTTATG | ACAGCCCGCC | GGAACCGGTG | 250 |
| GGCTTTTTTG | TGGGGTGAAT | ATGGCAGTAA | AGATTTCAGG | AGTCCTGAAA | 300 |
| GACGGCACAG | GAAAACCGGT | ACAGAACTGC | ACCATTCAGC | TGAAAGCCAG | 350 |
| ACGTAACAGC | ACCACGGTGG | TGGTGAACAC | GGTGGGCTCA | GAGAATCCGG | 400 |
| ATGAAGCCTG | CTTTTTTATA | CTAAGTTGGC | ATTATAAAAA | AGCATTGCTT | 450 |
| ATCAATTTGT | TGCAACGAAC | AGGTCACTAT | CAGTCAAAAT | AAAATCATTA | 500 |
| TTTGATTTCA | ATTTTGTCCC | ACTCCCTGCC | TCTGTCATCA | CGATACTGTG | 550 |
| ATGCCATGGT | GTCCGACTTA | TGCCCGAGAA | GATGTTGAGC | AAACTTATCG | 600 |
| CTTATCTGCT | TCTCATAGAG | TCTTGCAGAC | AAACTGCGCA | ACTCGTGAAA | 650 |
| GGTAGGCGGA | TCTGGGTCGA | CTCTAGGCCT | CACTGGCCTA | ATACGACTCA | 700 |
| CTATAGGGAG | CTCGAGGATC | ATTGCTAATA | CCATGAAACT | TGACCACCTG | 750 |
| GTCAAGGACT | GGTCCAGGGT | CCACAGTTTC | TGAGAAGAGC | AGGCTCCAAC | 800 |
| TTCTAACCAC | AAAAACTATT | TTTTCCATGC | GCTCCTTAAA | TTAGGCAGCG | 850 |
| CCCAGCTATT | TTCTTTCCTG | ACCACTGAGA | GGTAAATACT | CAAGCAGATG | 900 |
| GGAAACAGGG | GAAGATAGCA | AGGCCTCTTC | ATCATTATCA | CTGGGTGTGT | 950 |
| GCGTGAGGGG | AGGGGTGTCA | TTGCATACAC | AGGGCAACAT | CAGGATGGAA | 1000 |
| GCCTTGAGGA | CAGAGGAACA | TCAAAGGGAT | CCTGAGGACA | ACAGCTGGGA | 1050 |
| GCAGTTGCCA | TCAGTGAGTG | CCTTCTCTAA | GTGTGGGGCC | TTTCTCTGCC | 1100 |
| ACATAAATGC | AGGCTGCCTC | CTCTCTCCAC | ACACTGGTCT | CCAGCTCACC | 1150 |
| AATCCTCCAG | GTGACTTCCA | GCCATGAAGA | CTCTTGTCCT | CCTCTCTGCC | 1200 |
| CTTGTCCTGG | TGGCCTACCA | GGTCCAGGCT | GATCCCATTC | AAGGGGCAGA | 1250 |
| AGAAGAGACT | AAAACTGAAG | AGCAACCATC | AGATGAGGAC | CAGGATGTGT | 1300 |
| CTGTCTCCTT | TGAAGGCCCA | GAAGCCTCTG | CTCTTCAAGA | TTTTGGTGAG | 1350 |
| TGCTTATGCA | CAGAATGATG | GAGGCTTGGA | GTCTCCTGAT | GGAGGGTTGT | 1400 |
| AGATTAGACC | TGGAATCCTG | TCAAGAACTG | TCTGGTTCAG | GTAGCTGTCT | 1450 |
| CTTGGTCCCT | TTACATTCCT | TGTCTTCTTC | ATAGAAGTAA | CGGAGAGAGA | 1500 |
| TTAACCATTG | GGCTTGACTT | TTTTCCTTTT | AAAATTTTTG | ATCTAACAAT | 1550 |
| TTATCTGTGG | AAAACCTTTA | AAATATAAAA | CATATTGATT | AGTTCTTTTA | 1600 |
| GACCTGATTG | ATAATTTTGT | TATAAGAAGA | AATATTCGTT | CTACTTTAAA | 1650 |
| AATTAGATTT | GGGACCCAAA | TGCCAGTGTA | TGAAGCTGTT | GGGTAAGGAA | 1700 |
| AAACCAAAAA | TGGTGATAGA | ATGTTGTGTA | GATGACAATT | CCTTTATGCG | 1750 |
| ATTAACACTT | TTTAAAATGT | CTTATCTCCA | TGTGTTTGGG | GTTGATCATG | 1800 |

FIG. 15B(2)

RAT CRYPTIN 2 GENOMIC SEQUENCE

| 10 | 20 | 30 | 40 | 50 | |
|---|---|---|---|---|---|
| 1234567890 | 1234567890 | 1234567890 | 1234567890 | 1234567890 | |
| GTGCTGACTG | TGATGTCACC | CACAGAGCAA | ACCTACTCTC | TACCATGCAC | 1850 |
| AGGACATCTT | CATAGGGTAG | TTCACTGTCA | CACACTGCTG | GCCTCGTTAC | 1900 |
| TTCATGCCTG | ATGCTTTCTT | GTTTCCTCAG | AGATAGGAAG | GCCAGTGAGG | 1950 |
| AGGTGCCGTT | GCAGAGCAAA | CTGCGGACCT | AAAGAATATG | CCACTGCGTT | 2000 |
| CTGTGCTCAA | GGTCCATTTA | AACAGTTCAA | ATTCTGCTGC | ACATGAACAT | 2050 |
| GGATCCCAAG | TCTGAGATAA | CCACGTGCTC | TGGGACCTCA | CAATCTGTCA | 2100 |
| TTATTGTGCT | TGACCTCAAC | TGCTTTTCCT | TCTCCAATAA | ACTCCTGGCA | 2150 |
| GACAAATAAT | CGGTATATGT | TTATTTGATG | CTTTCTATTT | GGCTTAGACA | 2200 |
| GAACTCTCCT | GAGCCATGTA | GCTGAATCTT | CAGTGAATCC | TTTGTAAAGG | 2250 |
| TCACATTTCA | GCAGTCATAT | CAAGGATGAG | CAGGAGGTTA | GATACAAAGA | 2300 |
| GACAAGATGG | TCTGCGCCAG | CTGCTTCTTT | GTCTATCAAG | TCTGCTTTCC | 2350 |
| TTTAGATTAG | AGTCACCATC | AAAAATTATT | CCCACATTTT | CATGTTCTAT | 2400 |
| ATTTTTTT | | | | | 2408 |

FIG. 15C(1)

RAT CRYPTIN 3 GENOMIC SEQUENCE

| 10 | 20 | 30 | 40 | 50 | |
|---|---|---|---|---|---|
| 1234567890 | 1234567890 | 1234567890 | 1234567890 | 1234567890 | |
| CCTGAGACCA | ACTCTGTGAT | AATCAGAAAA | GACAATTATG | TGTCTTAAAT | 50 |
| GTAAGGTTTG | CTTCTTGACT | GATAGATCTA | ACCCTACAGA | GAGATTCAAG | 100 |
| TGGTCTTGTC | CCATTGAACA | ATAGTATATA | TGTTTTATAT | ATATATATAT | 150 |
| ATATATGTAT | ATGTATATAT | ATATGTGTGT | GTGTGTGTGT | GTGTGTCTGT | 200 |
| GTCTGTGTGT | CTGTGTGTCT | GTGTGTCTGT | GTGTCTGTGT | GTGTATGTGT | 250 |
| GTGTATGTGT | ACATATGTTC | AATATGTCTG | TAAAATAGTA | TTCTTGTAGC | 300 |
| TTCACTTACT | TTTGCACAGA | GCTGTAAATA | AGAACATTGT | AGCCAATGAA | 350 |
| TAGTATTTAT | TAACATGTAA | ATAGGAGCTG | GCACCTCTGA | CAGTGGGACT | 400 |
| CCATACAGTG | ACTGTAAACA | ACAGGATGCT | CTAGACCTTT | TGCTGTGTGT | 450 |
| GTGGTGAGAG | ACATGGGATA | AACACAGACT | GAAGTGTATG | ACATGGCGGC | 500 |
| ACTTCTCGAG | ACCGGGTAGC | AGCTTCTGAG | CCTCTCTACA | TTGTGGATGT | 550 |
| CCTTTCCTGT | AGGTCAGGTC | TCATTGTCTA | AAAGTAAAAG | CATTGCAGCA | 600 |
| TCTCAGACCT | GGGAAACACC | CCATGGCTTG | AGGGTCCCGC | AGGTGAAGAG | 650 |
| CCACCTGGAG | CTCACTCTTG | GCAGATGTGT | TCCATGACTT | TGGCTTCTTC | 700 |
| AGAACCACCC | ACTACAGCTT | CACTCTGACA | AATCTTAGAA | ACTTGAACTC | 750 |
| AATTCACTGG | AGGGCACAAT | AAAGCCATCT | TACTTTCTCT | AAAATGGCCC | 800 |
| CAAAGGAGGG | GATTCACAAA | GTTTGCCTTG | ATGAGGACCA | TTGCTAATAC | 850 |
| CCCAAAACTT | GCAAAAAAAA | TTGAGTGTCC | AGTCAACCTG | GTCAAGGACT | 900 |
| GGTCCTGGAT | CCACAGTTTC | TGAGAAAAGA | AGGCTCCAAC | TTCAAAACAC | 950 |
| AAACCACTCC | TGTTCTATGC | GCTCATTAAA | TTAGGCAGTG | TTAAGCTATT | 1000 |
| TTCTTTCCTG | ACCACTGAGA | GGTAAATACT | CAAGCAGATG | GGAAACAGGG | 1050 |
| GAGGACAGCA | AAGCCTGTTC | ATCATTATCA | GTGGGAGTGT | GCGTGAGGGG | 1100 |
| AGGGGTGTCA | GTGAACACAC | AGAGCATCAG | GAAGGAAGCC | TTGAGGACAG | 1150 |
| AGGAACATCA | AAGGGATCCT | GAGGACAACA | GCTGGGAGCA | GTTGGCATCA | 1200 |
| GTGAGTGCCG | TCTCTAAGTG | TGGGGCCTTT | CTCTGCCACA | TAAATGCAGG | 1250 |
| CTGGCTCCTC | TCTCCACACA | CTGGTCTCCA | GCTCACCAAT | CCTCCAGGTG | 1300 |
| ACTTCCAGCC | ATGAAGACTC | TTGTCCTCCT | CTCTGCCCTT | GTCCTGCTGG | 1350 |
| CATTCCAGAT | CCAGGCTGAT | CCCATTCAAG | AGGCAGAAGA | AGAGACTAAA | 1400 |
| ACTGAGGAGC | AGCCAGCAGA | TGAGGACCAG | GATGTGTCTG | TCTCCTTTGA | 1450 |
| AGGCCCAGAA | CCCTCTGCTC | TTCAAAATTT | AGGTGCGTGC | TTGTGCACAG | 1500 |
| AATGATGGAG | GCTTGGAGTC | TCCTGATGGA | GGGTTGTAGA | TTAGCCCTGG | 1550 |
| AGTCCTGTCA | AGGACAGTCT | GGTTCAGGTA | GCTGTCTATT | GATCCTTTCA | 1600 |
| GAACTTCCCT | GTCTTATTCA | TAGAAATAAC | AGTGAGAGAC | AAGCCATTGG | 1650 |
| GCTTGACTTT | TTCCTTTTAA | GATTTTGGTC | TAACAATTTA | TCTGTGAAAA | 1700 |
| ACCTTTAAAA | TATAAAACAT | ATTGATTAGT | TCTTTTAAAC | CTGATTGATA | 1750 |
| ATTTTGTTAT | AGGAAGAAAT | AACTGTTCTA | CTTTAAAAAT | TAGATTTGGT | 1800 |
| ACCTAAATGC | CAGTGTATTA | AGGTGTTGGG | TCAGGAAAAC | ACAATAATGC | 1850 |
| TGATAGAATG | TGGTGTAGAT | GACAATTCCT | ATATGCGATT | AACACTTGTT | 1900 |

FIG. 15C(2)

RAT CRYPTIN 3 GENOMIC SEQUENCE

| 10 | 20 | 30 | 40 | 50 | |
|---|---|---|---|---|---|
| 1234567890 | 1234567890 | 1234567890 | 1234567890 | 1234567890 | |
| AAATTGTCCT | ATCTCCATGT | GTTTGGGGTT | GATCATGGTG | CTGGCTGTGA | 1950 |
| TGTCACCCAC | ACAGCAAACC | TACTTTCTAC | CATGCACAGG | ACATCTTCAT | 2000 |
| AGGGTAGTTC | ACTGTCACAC | ACTGCTGGCC | TCCTTACTTC | ATGCCTGATG | 2050 |
| CTTTCTCGTT | TCCTCAGAGA | TCAGATGGCC | ATGGAAGAGG | TGCCATTGCA | 2100 |
| GAAGTTTCTG | CAGACCTTAT | GAAAATGCCA | CTTCGTTCTG | TGCTCAAGGT | 2150 |
| CTATTTAAAC | AACACAAATT | CTGCTGCCTA | GAAACATGGC | CCCCAAGGAT | 2200 |
| GAAATAACCA | CGTGCTCTGG | GACCTCACAA | TCTGTCATCA | TTGTGCTTGG | 2250 |
| CCTCAACTTC | TTTTCCTTCT | CCAATAAACT | CCTTGCAGAC | AAATAACCTG | 2300 |
| TTTATGTTTT | TTTGATGCTT | TCTATGTGGC | TTAGACAGGG | CTCTCCTGAG | 2350 |
| CCATGTAGCA | GAATCTTCAG | TGAATCCTTT | GTAAAAGAAG | TCTTGGTCAC | 2400 |
| ATTTCAACAG | TCATATCAAG | GATGAGCAGG | AGGTTAGATC | CAAAGAGACA | 2450 |
| AGATGCTCTG | CTCCAGCTGC | TTCTTGACTA | TCAAGTCTTC | TGTCCTTCAG | 2500 |
| ATTAGAGTCA | CCCTCAAAAA | TTAGTCCCAC | CTTTTCATGT | TCTATTTTTT | 2550 |
| T | | | | | 2551 |

ANTIBIOTIC CRYPTDIN PEPTIDES AND METHODS OF THEIR USE

This application is a continuation-in-part of U.S. Ser. No. 07/930,649, filed Aug. 14, 1992 now U.S. Pat. No. 5,422,424, which is a continuation-in-part of U.S. Ser. No. 07/889,020, filed May 26, 1992 now abandoned, each of which is incorporated herein by reference.

This invention was made with government support under grant numbers AI22931, AI31696, DK08851, DK44632 and DK33506, awarded by National Institutes of Health. The Government has certain rights in the invention.

BACKGROUND OF THE INVENTION

1. Field of the Invention

This invention relates generally to antimicrobial peptides and more specifically to cryptdin peptides, nucleic acid molecules encoding cryptdins, and their uses.

2. Background Information

Survival in a world teaming with microorganisms depends on a network of host defense mechanisms. Among these mechanisms are phagocytosis by cells are resident in tissues or that circulate in the blood system and ingest, kill and digest potentially harmful microbes. Although pathogenic microbes may vary considerably, phagocytes are able to destroy the vast majority by sequestering them in intracytoplasmic vacuoles and exposing them to a lethal mixture of organic and inorganic toxins.

Perhaps the most remarkable ultrastructural feature of phagocytes are their several thousand cytoplasmic granules, which are membrane-bound organelles typically about 0.3 $\mu$m in diameter. During phagocytosis, some of these granules fuse to phagocytic vesicles thus enabling the contents of the granule to enter the lumen of the vesicle. Early observers surmised correctly that the granules contained factors which were responsible for intraphagosomal killing in digestion of microbes. These granules contain a mixture of antimicrobial molecules including various peptides such as the so-called defensins.

Defensins are abundant antimicrobial peptide components of vertebrate neutrophil and macrophage granules. Members of the defensin family have been identified previously in human, rabbit, guinea pig and rat phagocytes, primarily those phagocytes termed phagocytic granulocytes. Defensins are cationic peptides that have molecular weights between about 3 and 4 kiloDaltons (kDa) and that exhibit broad-range antimicrobial activities against gram negative and gram positive bacteria, many fungi and some enveloped viruses. The peptides are characterized by eight invariant amino acids, including six invariant cysteine residues that constitute a unique disulfide motif. The three disulfide bonds stabilize a tertiary conformation consisting predominantly of β-sheet. The highly ordered structure and the absence of a helix make defensins unique among known antimicrobial peptides. It appears that defensins exert their antibacterial effect by permeabilizing the cytoplasmic membrane of the target microorganism by a mechanism that may involve the formation of ion channels or transmembrane pores.

Until recently, defensins had been identified only in circulating or tissue phagocytes of myeloid origin. However, based on the presence of a particular mRNA, it has been surmised that similar peptides might be present in the epithelial cells of the small intestine. Such intestinal peptides may prevent access of microorganisms through the small intestine into the systemic circulation and, therefore, can be useful as a therapeutic or prophylactic agent. Thus, a need exists to identify peptides that have antimicrobial activity within the mucosal epithelium or in the intestinal lumen. The present invention satisfies this need and provides additional benefits as well.

SUMMARY OF THE INVENTION

The present invention provides a substantially purified cryptdin peptide having a consensus amino acid sequence:

$X_1$-C-$X_2$-C-R-$X_3$-C-$X_4$-E-$X_5$-C-$X_6$-C-C-$X_7$ wherein $X_1$ is 3 to 9 amino acids; $X_2$ is 1 amino acid, preferably Y, H or R; $X_3$ is 2 or 3 amino acids; $X_4$ is 3 amino acids; $X_5$ is 5 amino acids; $X_6$ is 6 to 10 amino acids; and $X_7$ is 0 to 9 amino acids.

The invention also provides a substantially purified mouse cryptdin having a consensus amino acid sequence:

$X_1$-L-$X_2$-C-Y-C-R-$X_3$-C-K-$X_4$-E-$X_5$-G-T-C-$X_6$-C-C-$X_7$ wherein $X_1$ is 3 or 4 amino acids, preferably LRD, LSKK (SEQ ID NO: 1) or LRG;

$X_2$ is 1 amino acid, preferably V, L or I;

$X_3$ is 3 amino acids, preferably KGH or *RG, where * is S, T, K, I or A;

$X_4$ is 2 amino acids, preferably GR, RR or RG;

$X_5$ is 3 amino acids, preferably RMN, RVR, RVF HMN or HIN;

$X_6$ is 6 to 9 amino acids, preferably GIRFLY (SEQ ID NO: 2) or RNLFLTFVF (SEQ ID NO: 3), RRGHLMYTL (SEQ ID NO: 4) or RKGHL*YT* (SEQ ID NO: 5), where * independently is L or M; and $X_7$ is 0 to 3 amino acids, preferably R, S or PRR.

For example, the invention provides various mouse, rat or human cryptdins having the sequence:

1) LRDLVCYCRSRGCKGRERMNGTCRKGHL-LYTLCCR (SEQ ID NO: 6);
2) LRDLVCYCRTRGCKRRERMNGT-CRKGHLMYTLCCR (SEQ ID NO: 7);
3) LRDLVCYCRKRGCKRRERMNGT-CRKGHLMYTLCCR (SEQ ID NO: 8);
4) GLLCYCRKGHCKRGERVRGTCGIRFLYCCPR (SEQ ID NO: 9);
5) LSKKLICYCRIRGCKRRERVFGTCRNLFLTFVFCC (SEQ ID NO: 10);
6) LKQCHCRKFCRPYEKAEGSCR-PGLFIKRKICCIQQWTPG (SEQ ID NO: 11);
7) GLLCYCRKGHCKRGERVRGTCGIRFLYCCPRR (SEQ ID NO: 12);
8) LSKKLICYCRIRGCKRRERVFGTCRNLFLTFVFCCS (SEQ ID NO: 13);
9) LRDLVCYCRARGCKGRERMNGTCRKGHL-LYMLCCR (SEQ ID NO: 14);
10) LKQCHCRKFCRPYEKAEGSCR-PGLFIKRKICCIQQWTPGRT (SEQ ID NO: 15);
11) IGRPVRRCRCRANCGPKEYATAFCAQG-PFKQFKFCCT (SEQ ID NO: 16);
12) IRWPWKRCHCRSFCRPYENATSF-CAQGLFKQHKFCCLDTWPPRMK (SEQ ID NO: 17);
13) TSGSQARATCYCRTGRCATRESLSGV-CEISGRLYRLCCR (SEQ ID NO: 18); and
14) AFTCHCRRSCYSTEYSYGTCTVMGINHRFCCL (SEQ ID NO: 19).

Cryptdins are typically characterized by being naturally found in the epithelial cells of the small intestine, being cationic, being about 30 to about 45 amino acids in length, having at least three and, preferably, three to nine amino acids to the N-terminal of the first cysteine residue, exhibiting specific antimicrobial activity against intestinal pathogens and opportunistic pathogens and being relatively non-toxic to cells of the host organism. However, there may be diversity in these structural and functional characteristics. The invention also provides cryptdin analogs, which are devoid of one or more amino acids N-terminal to the first cysteine. In addition, the invention also provides nucleic acid molecules encoding cryptdin peptides. For example, the invention provides genomic DNA sequences and cDNA sequences encoding mouse and rat cryptdins.

The invention further provides a method for detecting an inflammatory pathology in a subject by determining the amount of cryptdin in a biological sample from the subject and comparing that amount to the amount present in a normal subject. Such a method can be used to determine the presence of an inflammatory pathology such as inflammatory bowel disease, pancreatitis, malignancy, infection or ileitis.

The invention also provides a method for treating an inflammatory pathology in a subject by administering a cryptdin to the subject. Such treatment is particularly advantageous in patients who are immunocompromised due, for example, to malnutrition, radiation burns, immunosuppressive infections, autoimmune disease, neonatality, bone marrow transplantation or chemotherapy. A cryptdin can be administered orally, by nasogastric intubation, by transabdominal catheter, intravenously or by aerosol inhalation. When administered orally, it is preferably in a delayed release formulation designed to permit release in the small intestine. The cryptdin can be administered as a composition with a physiologically acceptable medium, and more than one cryptdin can be administered simultaneously or sequentially.

BRIEF DESCRIPTION OF THE DRAWINGS

FIG. 4.A. Lyophilized luminal lavage of small intestine from 12 mice and 20 $\mu$g protein was fractionated by P-60 gel filtration and electrophoresed on an acid-urea acrylamide gel (lane 2) along side a similarly prepared sample of bowel tissue (lane 1). The positions of cryptdins 1–5 (SEQ ID NOS: 6 to 10, respectively) are indicated.

FIG. 4.B. Partially purified luminal peptides (20 $\mu$g; as for FIG. 4.A., lane 2) were electrophoresed in a second acid-urea gel (lane 3) along with an identical sample previously treated with performic acid (lane 4). In lane 4, rapidly migrating, cyst(e)ine-containing peptides are absent due to the increased net negative charge resulting from the conversion of cyst(e)ines to cysteic acid residues.

FIGS. 6.A. and 6.B., 40X; FIGS. 6.C. and 6.D., 250X; FIGS. 6.E. and 6.F., 640X.

FIGS. 9.A. and 9.B. show the amino acid sequences of mouse cryptdins 1–17 (SEQ ID NOS: 23 to 39, respectively) as determined from the cDNA sequences encoding the specific cryptdin.

FIG. 9.A. shows the entire amino acid sequence of the mouse cryptdins. The amino acid sequences of cryptdins 1–6 (SEQ ID NOS: 23 to 28) were determined by sequencing the purified peptides. The amino acid sequences of cryptdins 7–17 (SEQ ID NOS: 29 to 39) were deduced from the cDNA sequences (see FIG. 10). The amino acids encoded by Exon 1, which encodes the signal peptide and propiece, and Exon 2, which encodes the mature cryptdin peptide, are indicated. A dot indicates the sequence was not encoded by the cDNA clone. "*" indicates a space, which preserves the homology of the sequences.

FIG. 9.B. indicates the degree of relatedness of the mouse cryptdins. Amino acids that are identical to the amino acid shown for cryptdin 1 (SEQ ID NO: 23) are indicated by a dot.

FIG. 10 shows the nucleic acid sequences for the cDNA sequences encoding mouse cryptdins 1–17 (SEQ ID NOS: 40 to 56, respectively). A consensus nucleotide sequence also is shown (SEQ ID NO: 57). A dot indicates the nucleotide is the same as shown for cryptdin 1. The amino acid sequence for cryptdin 1 (SEQ ID NO: 23) is shown above the nucleic acid sequence. Numbers below the nucleotide sequence indicate the nucleotide position relative to the methionine start codon (+1). Numbers above the amino acid sequence indicate the amino acid position. Italics indicate the mature cryptdin peptide sequence. Nucleotides in lower case letters indicate non-coding sequences. "***" indicates a stop codon. "(A)$_n$" indicates poly-A tail. "*" indicates a space and "-" indicates the particular nucleotide could not be determined unambiguously.

FIG. 11 shows the genomic DNA sequences for mouse cryptdins 1, 2, 3, 5 and 6 (SEQ ID NOS: 58 to 62, respectively) and the genomic sequence for the apparently inactivated mouse cryptdin i gene (Crypi; SEQ ID NO: 63), in which a stop codon (TGA) is substituted for a cysteine residue. Numbering is as described in the legend to FIG. 11. The upper sequence represents a consensus cryptdin gene sequence (SEQ ID NO: 64). "X" indicates positions at which at least two sequences containing nucleotide changes. The TATAAA box is shown in lowercase italics; exons are shown in capital letters; "**" indicates intron DNA; "n" represents approximately 500 base pairs that were not sequenced. "@" indicates the start of the cryptdin peptide coding region at codon 59. Coding sequences are indicated in bold print. Prepro-regions are coded by nucleotides 1–172; cryptdin peptides are coded by nucleotidase 173–279. The stop codon is underlined.

Figure 1:
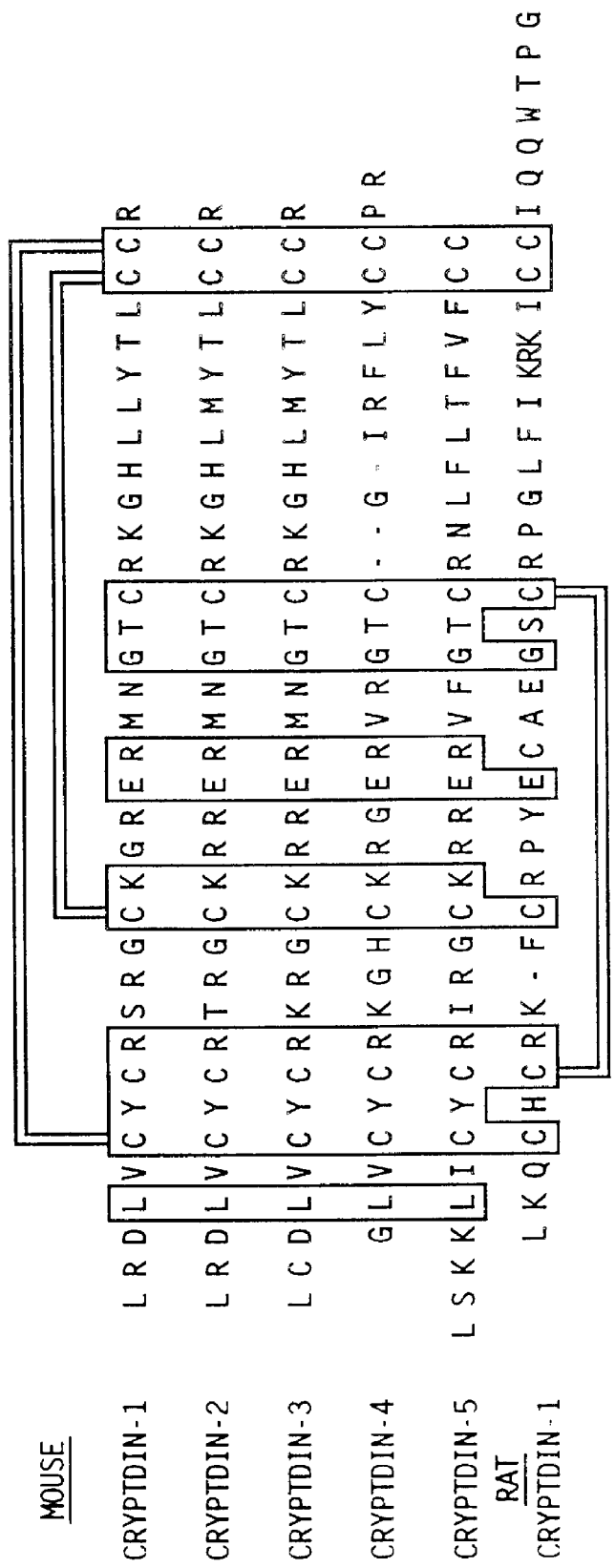
FIG. 1 provides the structures of mouse cryptdins 1–5 (SEQ ID NOS: 6 to 10, respectively) and rat cryptdin 1 (SEQ ID NO: 11). Amino acid residues are indicated by single letter code. Dashed lines are included in mouse cryptdin 4 (SEQ ID NO: 9) and rat cryptdin 1 (SEQ ID NO: 11) in order to preserve the consensus sequence where these peptides are shorter than other cryptdins. Invariant residues in the enteric cryptdin peptides are boxed. Disulfide bonding motifs are depicted by connecting double lines.

GenBank accession numbers for these sequences are 002994 (cryptdin 1, exon 1); 002995 (cryptdin 1, exon 2); 002996 (cryptdin 2, exon 1); 002997 (cryptdin 2, exon 2); 002998 (cryptdin 3, exon 1); 002999 (cryptdin 3, exon 2); 003000 (cryptdin 5, exon 1); 003001 (cryptdin 5, exon 2); 003002 (cryptdin 6, exon 1); 003003 (cryptdin 6, exon 2); 003004 (cryptdin i, exon 1); and 003005 (cryptdin i, exon 2).

Figure 12A:
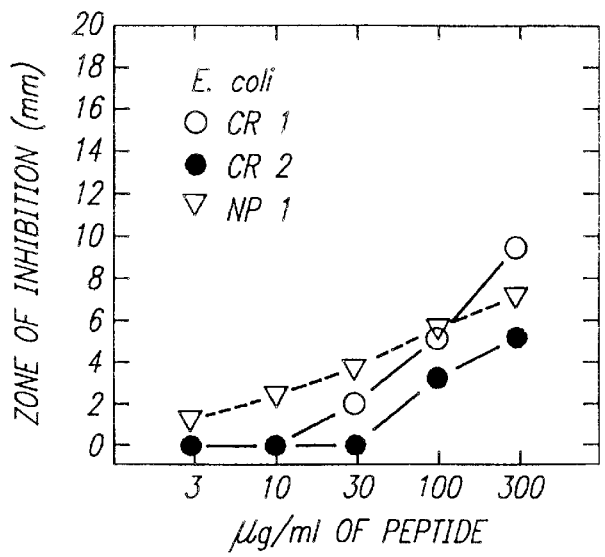
Figure 12B:
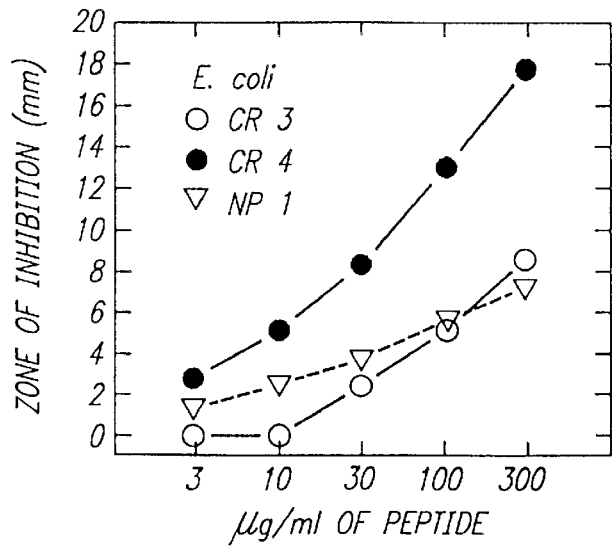
Figure 12C:
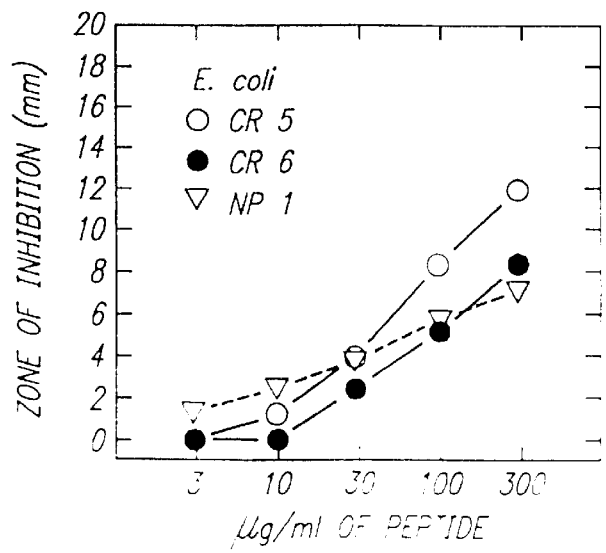

FIGS. 12.A. to 12.C. demonstrate the effectiveness of mouse cryptdins (as indicated) in inhibiting the growth of *E. coli* ML35 cells in an agar diffusion assay.

Figure 13A:
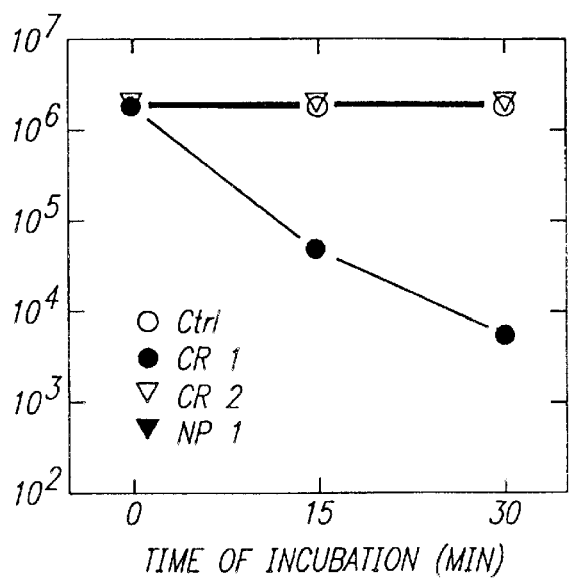
Figure 13B:
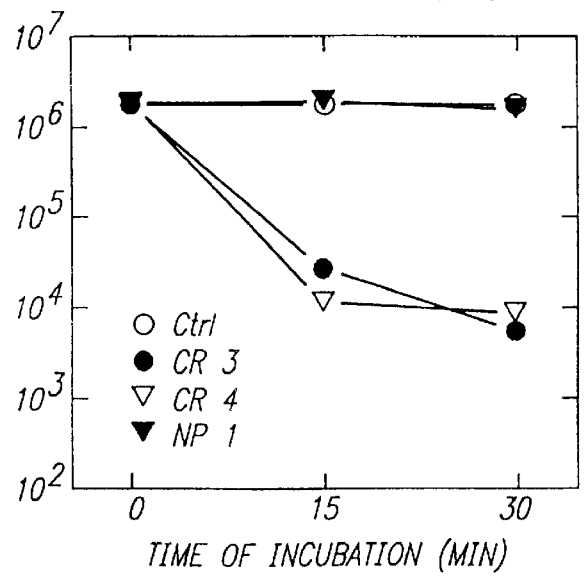
Figure 13C:
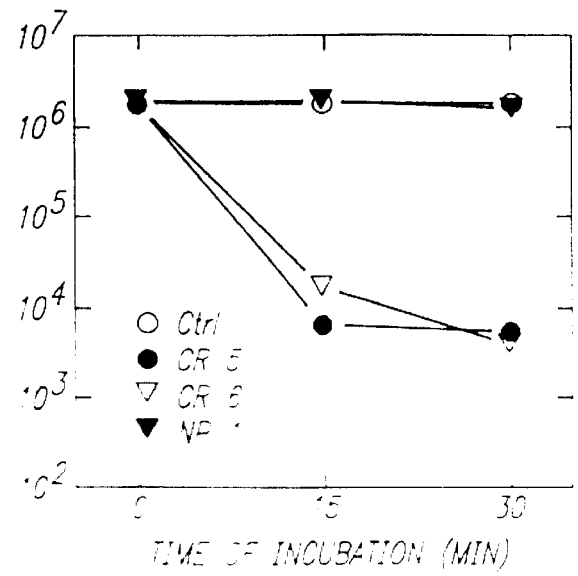

FIGS. 13.A. to 13.C. demonstrate the effectiveness of mouse cryptdins (as indicated) in killing *E. coli* cells in suspension.

FIGS. 14.A. to 14.C. show the cDNA sequences encoding rat cryptdin 1 (FIG. 14.A.), rat cryptdin 2 (FIG. 14.B.) and rat cryptdin 3 (FIG. 14.C.). Nucleotide numbers are indicated.

FIGS. 15.A. to 15.C. show the genomic DNA sequences encoding rat cryptdin 1 (FIG. 15.A.), rat cryptdin 2 (FIG. 15.B.) and rat cryptdin 3 (FIG. 15.C.). Nucleotide numbers are indicated.

DETAILED DESCRIPTION OF THE INVENTION

The invention provides small peptide molecules, termed cryptdins, which express a broad range of antimicrobial activity, particularly against intestinal pathogens, and for this reason are useful antimicrobial agents. For example, cryptdins have antimicrobial activity against gram negative and gram positive bacteria and against protozoan pathogens (see Example III). Cryptdin peptides and nucleic acid sequences encoding cryptdins were isolated from the small intestine and are active within the epithelial lining of the small intestine and within the lumen of the intestine. Because it is indicative of inflammatory processes, the presence of cryptdins can be utilized in the diagnosis of a wide range of inflammatory conditions.

As used herein, the term "cryptdin" or "enteric defensins" refers to peptides having generally between about 30 and 45 amino acids. Cryptdins are characterized, in part, by a consensus sequence containing six cysteine residues. Illustrative sequences are provided in FIG. 1, which shows invariant residues and the disulfide bonding motif. In addition, those residues which are preferably invariant are identified (see, also, FIGS. 8 and 9).

Cryptdins are further characterized by their cationic charge and their broad range of antimicrobial activity. While related to leukocyte-derived defensins, cryptdins are distinguished from these other molecules by the presence of 3 to 9 amino acids N-terminal to the first cysteine molecule. Cryptdins may have C-terminal extensions as well. In addition, they exhibit antimicrobial activity against enteric microorganisms, which can become blood-borne pathogens if the intestinal barrier is breached. Since cryptdins are associated with the secretory granules of Paneth cells in the small intestine, they can be secreted from the cells in which they are produced (Satoh, *Cell Tiss. Res.* 251:87–93 (1988); Satoh et al., *Acta Histochem.* 83:185–188 (1988)). Unlike leukocyte-derived defensins, cryptdins are not toxic to mammalian cells.

It should be appreciated that various modifications can be made to the cryptdin amino acid sequence without diminishing the antimicrobial activity of the peptide. It is intended that peptides exhibiting such modifications, including amino acid additions, deletions or substitutions are within the meaning of the term "cryptdin" and, therefore, within the scope of the invention. For example, cryptdin analogs, which are devoid of one or more amino acids N-terminal to the first cysteine residue, are within the present invention. Such cryptdin analogs can be synthesized using well known methods (see Example VI) or can be purified from the intestine where they may occur naturally due, for example, to partial proteolysis of a cryptdin peptide in the intestinal lumen.

Use of the phrase "substantially pure" in the present specification and claims as a modifier of peptide, protein or nucleic acid means that the peptide, protein or nucleic acid so designated has been separated from its in vivo cellular environment. As a result of the separation and purification, the substantially pure peptides, proteins and nucleic acids are useful in ways that the non-separated impure peptides, proteins and nucleic acids are not.

Figure 8:
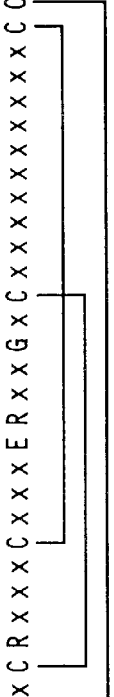
FIG. 8 shows the amino acid sequences for rat cryptdins 1–3 (SEQ ID NOS: 15–17, respectively), human cryptdins 5 and 6 (SEQ ID NOS: 18 and 19; HD-5 and HD-6) and a consensus sequence (Def consensus). Also shown are the amino acids sequences for rat prepro-cryptdins 1–3 (SEQ ID NOS: 20–22) as deduced from cDNA or genomic DNA sequences as indicated.
Figure 9B:
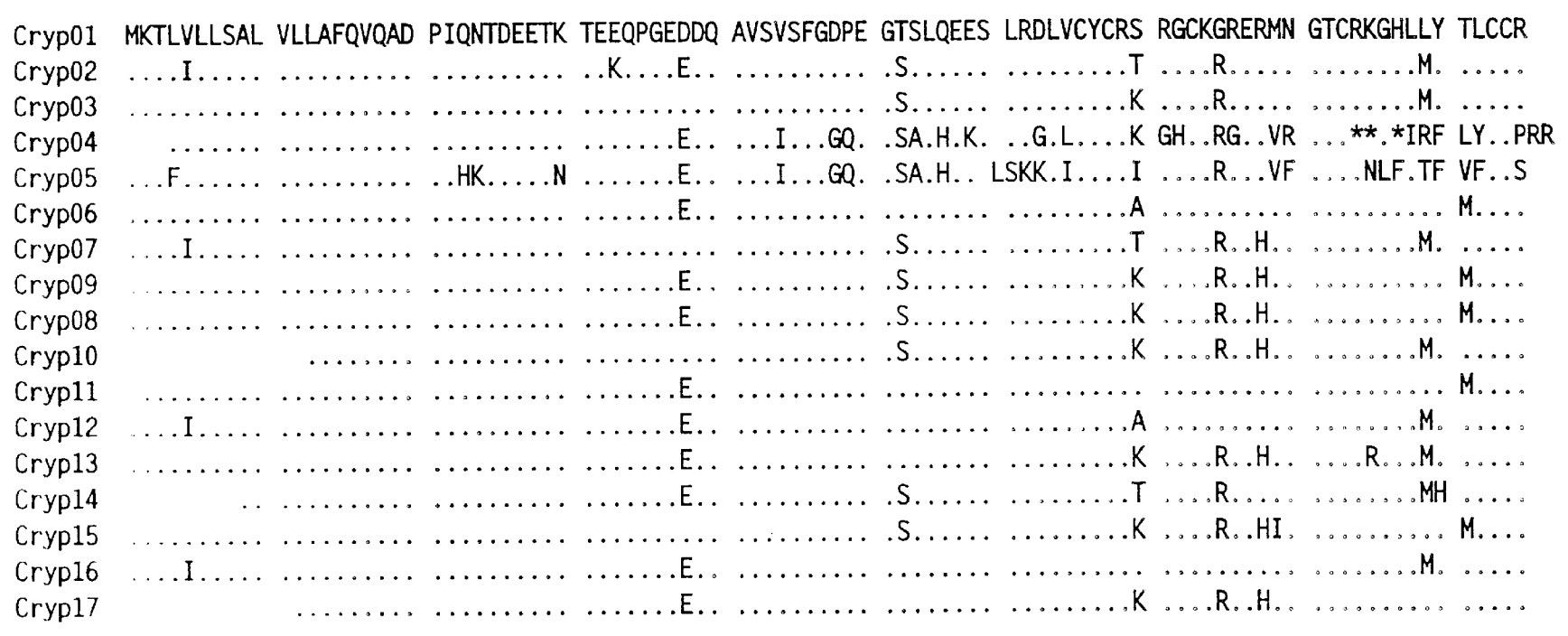

The cryptdin peptides of the present invention preferably contain between about 30 and 45 amino acids (see FIGS. 1, 8 and 9). Cryptdins can be synthesized by methods well known in the art, such as through the use of automatic peptide synthesizers or by well-known manual methods of peptide synthesis (see Example VI). In addition, they can be purified from natural sources such as small intestinal epithelium of vertebrate, preferably mammalian, origin (see Example I). Such epithelium can be obtained, for example, from rats, mice or humans using means well known to those skilled in the art.

As disclosed herein, various cryptdin peptides were isolated from intestinal epithelium, purified by chromatographic methods and characterized by electrophoresis and amino acid sequencing. Cryptdins were identified by their rapid migration on acid-urea PAGE and by their apparent molecular weight of about 4 kDa (see Examples I and II).

Anti-cryptdin antibodies were made using methods conventional in the art. For example, polyclonal antiserum can raised in appropriate animals, such as rabbits, mice or rats. Cryptdin peptides, either synthetic or obtained from natural sources, can be used to immunize the animal. As described in Example IV, a cryptdin analog, cryptdin C, which corresponds to residues 4–35 of mouse cryptdin 1 (SEQ ID NO: 6) as shown in FIG. 1, was used to immunize rabbits using well known methods. Serum samples were collected until the anti-cryptdin titer was appropriate. Various fractions of the antiserum, such as IgG, can be isolated by means well known in the art. Cryptdin immunogens also can be used to obtain monoclonal antibodies using methods well known in the art (see, for example, Harlow and Lane, *Antibodies: A Laboratory Manual* (Cold Spring Harbor Laboratory Press 1988), which is incorporated herein by reference).

The antimicrobial activity of a cryptdin can be measured against various pathogens. As disclosed in Example III, various microorganisms were grown to an appropriate concentration, mixed with an appropriate medium such as an agarose-trypticase soy medium and contacted with a cryptdin. Antimicrobial activity was apparent, for example, from the clear zones that surrounded the cryptdins in an agar diffusion assay. The area of the clear zones was concentration dependent (see FIG. 12).

Anti-cryptdin antibodies can be used to determine the presence of cryptdin in a biological sample such as a histological sample. For example, sections of small intestine are fixed by means well known to those skilled in the art and incubated with anti-cryptdin antibodies such as an IgG fraction of antiserum. If desired, the anti-cryptdin antibody can be detectably labelled or an appropriate detectable second antibody can be used to identify the presence of the primary antibody attached to the cryptdin. Means of detection include the use of radioactive protein A or enzyme substrates such as peroxidase (see Harlow and Lane, supra, 1988).

Alternative methods of determining the presence of cryptdin in a biological sample obtained, for example, by intestinal lavage or by disrupting cells or tissues can be useful to determine the presence of inflammatory processes. In the presence of inflammatory processes, the concentration of cryptdins is significantly altered from that found in the normal cell. In particular, a deviation from the normal level of cryptdins by one to two standard deviations is indicative of an inflammatory process. Such an inflammatory process can include, for example, inflammatory bowel disease, pancreatitis, malignancy, infection or ileitis.

Because of their broad range of antimicrobial activity and their ability to function within the intestinal epithelium or lumen, cryptdins are potent therapeutic agents for infections of the intestine. In particular, cryptdins are useful where the subject is immunocompromised due, for example, to malignancy, malnutrition, chemotherapy, radiation, immunosuppressive viruses, autoimmune disease or neonatality. In addition, cryptdins are useful in surgical prophylaxis, for example, by functioning to help sterilize the small bowel. Thus, cryptdins can be useful as medicaments for treating a subject having a pathology characterized, in part, by an inflammatory process.

A cryptdin, either purified from natural sources or synthetic, can be administered to a subject in need of such therapy by various means, including orally, preferably in a slow-release type formulation, which will avoid release within the stomach. Alternatively, cryptdins can be administered through nasogastric intubation, transabdominal catheter, intravenously or aerosol administration. Individual species of cryptdin can be administered alone or in combination. Cryptdins administered in combination can be administered simultaneously or sequentially and can be repeated as necessary.

Prior to the characterization of a mouse intestinal defensin cDNA, expression of defensins was thought to be limited to professional phagocytes, i.e., neutrophils and macrophages. The presence of high levels of cryptdin mRNA in Paneth cells led to the hypothesis that defensins synthesized in intestinal epithelium may contribute to antimicrobial barrier function in the small bowel (Ouellette et al., *J. Cell Biol.* 108:1687–1695 (1989a), which is incorporated herein by reference). Isolation and characterization of six mouse cryptdin peptides, two rat cryptdin peptides and 2 human cryptdin peptides, and the demonstration of antimicrobial activity of various cryptdin peptides indicates that the cryptdins have an antimicrobial role in the small intestine. The immunohistochemical localization of cryptdin(s) to Paneth cells is consistent with previous in situ hybridization analysis and suggests that defensins produced by these cells may contribute to restricting the colonization and invasion of the small bowel by bacteria.

Figure 2A:
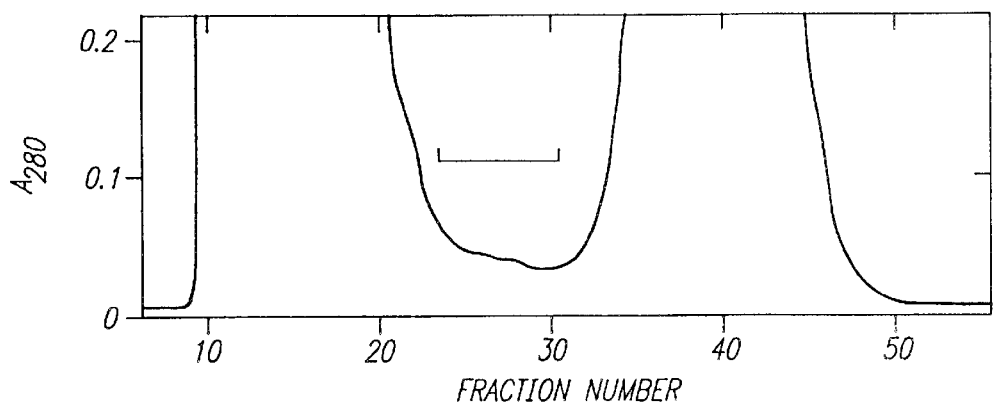
FIGS. 2.A. to 2.C. show chromatograms representing the purification of enteric cryptdins. Acid extract of jejunum and ileum was chromatographed in 30% acetic acid on a P-60 column. Fractions indicated by the bracket (FIG. 2.A.) were pooled and rechromatographed on the P-60 column (FIG. 2.B.). Cryptdin containing fractions (bracket, panel B) were pooled and further purified by reversed-phase high performance liquid chromatography (RP-HPLC) on 0.46×25 cm Vydac C-18 column. Water-acetonitrile gradient elution (--) using 0.13% (vol/vol) HFBA as modifier was used to purify cryptdins 1–5 (SEQ ID NOS: 6 to 10, respectively). The brackets in FIG. 2.C. indicate the peptide contained in each peak, and the portion of each which was subjected to a second round of RP-HPLC.
Figure 2B:
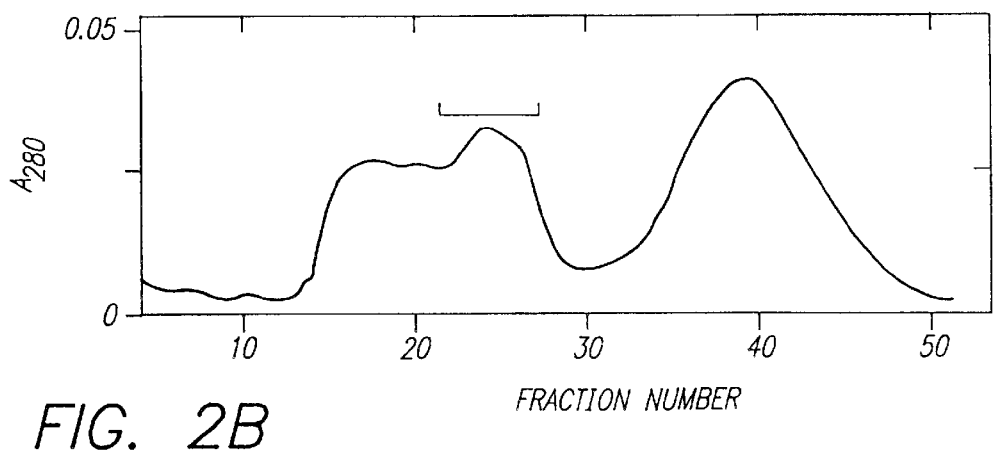
Figure 2C:
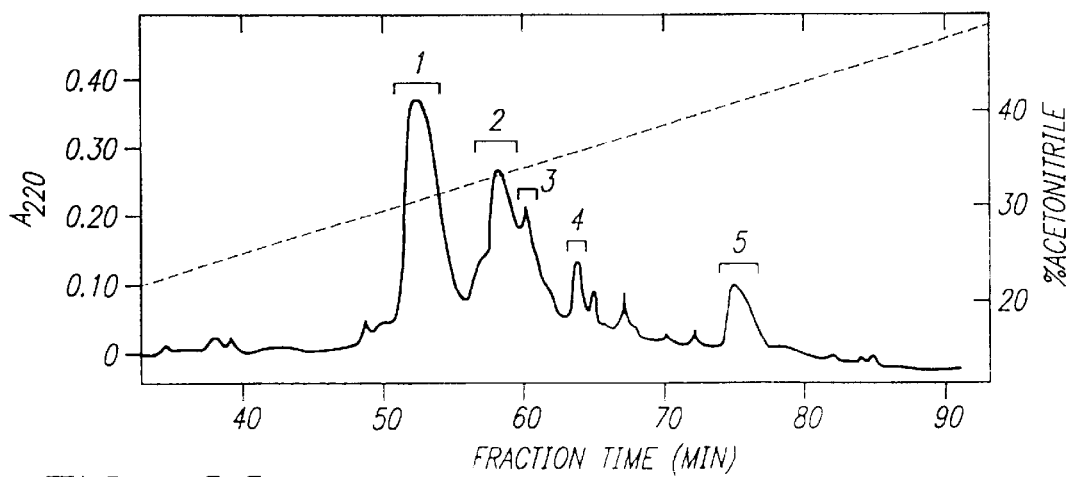
Figure 3:
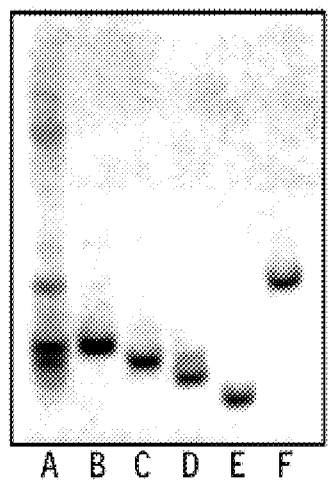
FIG. 3 shows acid-urea PAGE of purified enteric cryptdins. Samples of low molecular weight enteric peptides obtained by P-60 gel filtration (FIG. 2, panel B) and purified cryptdins were electrophoresed on a 12.5% acid-urea gel and stained with formalin-containing Coomassie Blue. Lane A: approximately 20 $\mu$g P-60 low molecular weight peptide fractions; lanes B–F: 1 $\mu$g each of cryptdins 1–5 (SEQ ID NOS: 6 to 10), respectively.

Initial efforts to purify intestinal defensins focused on the isolation of mouse cryptdin 1 (SEQ ID NO: 6), the peptide predicted from the cryptdin cDNA sequence. Since the deduced structure of the peptide is highly cationic, intestinal peptides were solubilized by homogenizing intact mouse jejunum and ileum in 30% formic acid. Acid-urea PAGE of the crude extract revealed several bands with $R_f$ values similar to those of rabbit defensin NP-1 and cryptdin C, a folded synthetic defensin congener corresponding to residues 4 to 35 in cryptdin 1 (SEQ ID NO: 6). Peptides corresponding to these bands were purified approximately 200-fold by sequential gel filtration chromatography on Bio-Gel P-60 (FIGS. 2.A. and 2.B.). Electrophoresis of P-60 column fractions on acid-urea gels showed that five fractions eluting between two prominent peaks (FIGS. 2.A. and 2.B., brackets) contained putative cryptdin peptides (FIG. 3, lane a). Peptides in these P-60 fractions migrated with an apparent molecular mass of approximately 4 kDa on SDS-PAGE (not shown), consistent with the molecular weight of defensins. Furthermore, treatment of P-60 fraction samples with performic acid reduced the electrophoretic mobility of the five putative mouse cryptdins in acid-urea gels, behavior that is characteristic of defensins and polypeptides that contain multiple cysteine residues.

Defensins in pooled P-60 fractions were purified further using sequential rounds of RP-HPLC utilizing different ion-pair agents. Initial HPLC fractionation utilized water-acetonitrile gradients containing 0.13% heptafluorobutyric acid (HFBA) as the ion-pairing agent, whereby each of the five peptides contained in the pooled P-60 fractions was resolved to near purity in a single run (FIG. 2.C.). Complete purification of five peptides, mouse cryptdins 1–5 (SEQ ID NOS: 6 to 10, respectively), was achieved by subsequent RP-HPLC using 0.1% trifluoroacetic acid (TFA) (FIG. 3, lanes B–F). Assuming extraction of individual peptides is equally efficient, both acid-urea gel electrophoresis and RP-HPLC of the P-60 fractions containing putative cryptdins showed that the relative abundance of the peptides is cryptdin 1> cryptdin 2> cryptdin 5> cryptdin 3> cryptdin 4. The relative amounts of cryptdins 1–5 (SEQ ID NO: 6 to 10, respectively) have been qualitatively reproducible in every preparation of acid-extracted protein from mouse small intestine.

Using a modification of the method described above, mouse cryptdin 6, rat cryptdin 2, and human cryptdins 5 and 6 also were isolated (see Examples I and II; see, also, FIGS.

8 and 9). In addition, longer forms of mouse cryptdins 4 and 5 (compare SEQ ID NOS: 9 and 12; 10 and 13) and rat cryptdin 1 (compare SEQ ID NOS: 11 and 15) were obtained. This result suggests that the initial method of purifying cryptdin peptides resulted in partial degradation of the C-termini of some peptides. Significantly, both forms of the purified cryptdin peptides have antimicrobial activity.

Biochemical characterization of the isolated cryptdins demonstrated that these peptides are defensins. Amino acid analysis of each peptide showed their compositions (cationic peptides of about 30 to 45 amino acid residues, including 6 half-cysteines) are compatible with defensin-like molecules. The complete sequences of mouse cryptdins 1–6 (SEQ ID NOS: 23 to 28), rat cryptdins 1 and 2 (SEQ ID NOS: 11, 15 and 16) and human cryptdins 5 and 6 (SEQ ID NOS: 18 and 19) were determined by automated Edman degradation and, in some cases, by amino acid analysis of carboxyl terminal chymotryptic peptides (see FIGS. 1, 8 and 9). The primary structures of the cryptdins contain the distinctive structural features of human, rabbit, rat and guinea pig neutrophil defensins (Lehrer et al., *Cell* 64:229–230 (1991a), which is incorporated herein by reference), i.e., the six invariant cysteine residues and the glycine and glutamic acid in positions that are highly conserved in myeloid defensins.

The cryptdin peptides disclosed herein contain features that are unique and distinct from defensins of myeloid origin. For example, mouse cryptdins 1, 2, 3 and 6 (SEQ ID NOS: 23 to 25 and 28, respectively) are almost identical, differing only at two or three positions (see FIG. 9.A.). Analysis of codons from which these amino acid differences could arise shows that the conversion, for example, of $Ser^{10}$ to $Lys^{10}$ in cryptdin 1 (SEQ ID NO: 23) and cryptdin 3 (SEQ ID NO: 25), respectively, requires two nucleotide substitutions. On the other hand, single nucleotide changes in the codon encoding $Thr^{10}$ in cryptdin 2 (SEQ ID NO: 24) could give rise to cryptdins 1, 3 and 6, suggesting that the cryptdin 2 gene may be an intermediate or progenitor of the cryptdin 1, 3 and 6 genes. Similarly, a single nucleotide change in the codon for $Thr^{10}$ of cryptdin 2 can account for the deduced amino acid at position 10 in cryptdins 7–17 (see FIG. 10, nucleotides 203–205; SEQ ID NOS: 46 to 56).

By homology with the structures of known myeloid defensins, the cryptdin 1 N-terminus was predicted to begin at $Leu^4$ or $Val^5$, which is 1–2 residues prior to the first conserved cysteine. However, compared to myeloid defensins, cryptdins have variably extended N-termini that contain from three (mouse cryptdin 4, SEQ ID NO: 26; rat cryptdin 1, SEQ ID NO: 11) to nine (human cryptdin 5, SEQ ID NO: 18) amino acids preceding the first cysteine. In mouse cryptdins 1–3 and 6–17 (SEQ ID NOS: 23 to 25 and 28 to 39, respectively), the N-peptidyl extensions consist of two charged internal residues flanked by amino acids with hydrophobic sidechains. Since natural variation in defensin amino termini correlates with relative antimicrobial potency in vitro (Ganz et al., *J. Clin. Invest.* 76:1427–1435 (1985), which is incorporated herein by reference), the extended N-termini of enteric defensins may have evolved for a unique role in the bowel.

Mouse cryptdin 4 (SEQ ID NO: 9), the most cathodal and, apparently, least abundant mouse enteric defensin, was the first defensin found to contain a chain length variation between the fourth and fifth cysteine residues. Unlike the majority of previously known defensins, in which nine amino acids separate the fourth and fifth cysteines (Lehrer et al., supra, 1991a), mouse cryptdin 4 (SEQ ID NO: 9) contains only six residues between the same two amino acids (FIG. 1). In addition, rat cryptdins 1–3 (SEQ ID NOS: 11 and 15–17) contain ten amino acid residues between the fourth and fifth cysteines. These findings indicate the defensin fold involving this stretch of the peptide chain can accommodate significant variability in the size of the loop, as compared to the invariant loop size defined by crystal and NMR structures, respectively, of human and rabbit neutrophil defensins. Also, rat cryptdins 1–3 (SEQ ID NOS: 11 and 15–17) are the only cryptdins containing three, instead of four, amino acid residues between the second and third cysteine residues.

Since cryptdin MRNA levels increase during postnatal development of mouse small bowel (Ouellette et al., supra, 1989a), it was investigated whether accumulation of enteric defensins was regulated similarly. Analysis of intestinal acid extracts from male and female mice showed that mouse cryptdins 1–3 and 5 (SEQ ID NOS: 6 to 8 and 10, respectively) are present in adult mice, regardless of gender. On the other hand, extracts from 9 day-old mice lack the peptides, consistent with postnatal accumulation of cryptdin MRNA.

Figure 5:
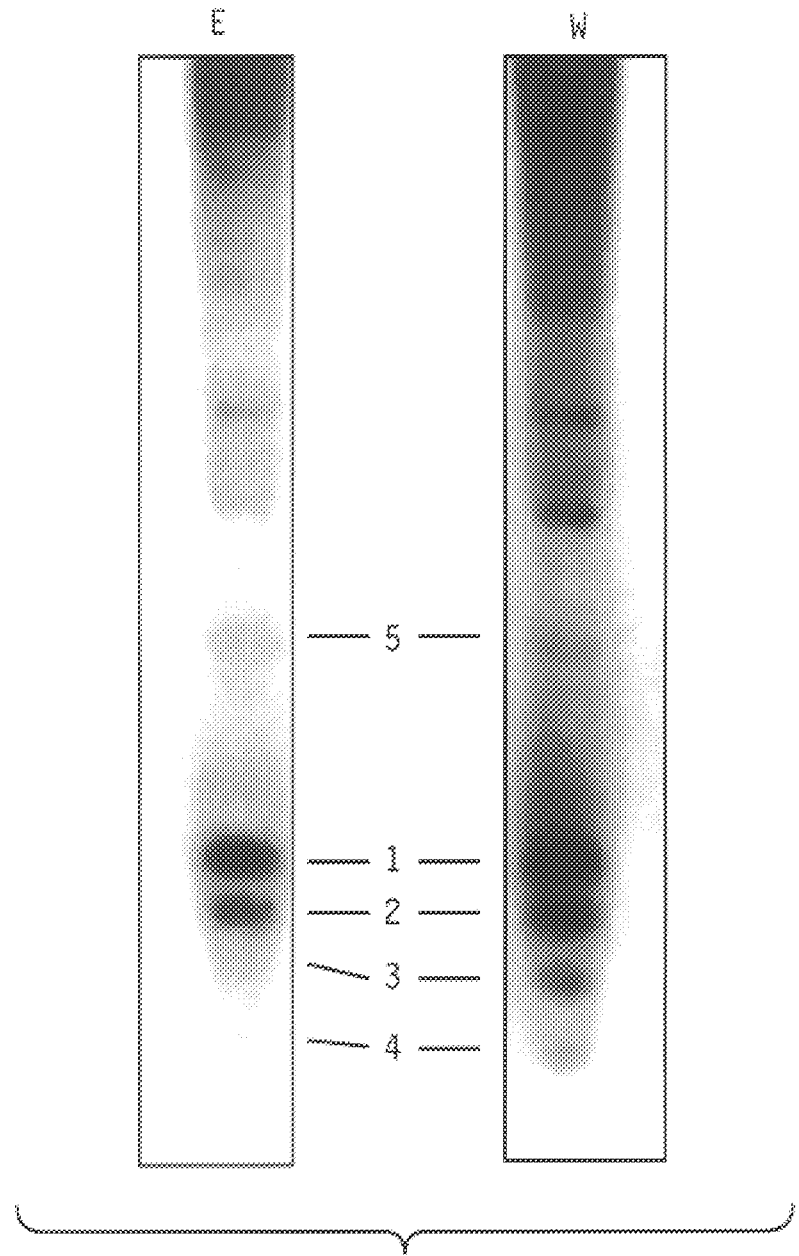
FIG. 5 shows the identification of mouse cryptdins 1–5 (SEQ ID NOS: 6 to 10, respectively) in small intestine epithelium. Acid extracts of intact, whole small intestine (W) or epithelial sheets (E) were lyophilized, dissolved in sample solution and resolved on a 12.5% acid-urea acrylamide gel. Cryptdins 1–5 (SEQ ID NOS: 6 to 10) are identified numerically.
Figure 6A:
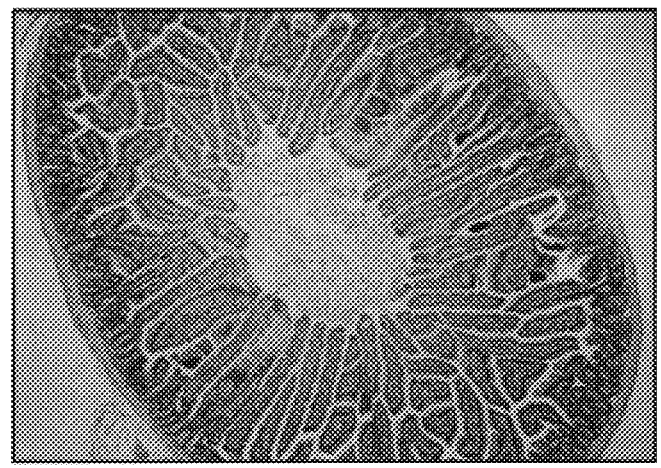
FIGS. 6.A. to 6.F. show the immunohistochemical localization of cryptdin 1 (SEQ ID NO: 6) in small intestine. Full thickness sections of adult mouse jejunem were incubated with preimmune (FIGS. 6.A., 6.C. and 6.E.) or anti-cryptdin C rabbit IgG (FIGS. 6.B., 6.D. and 6.F.) and developed using peroxidase anti-peroxidase secondary antibody magnifications.
Figure 6B:
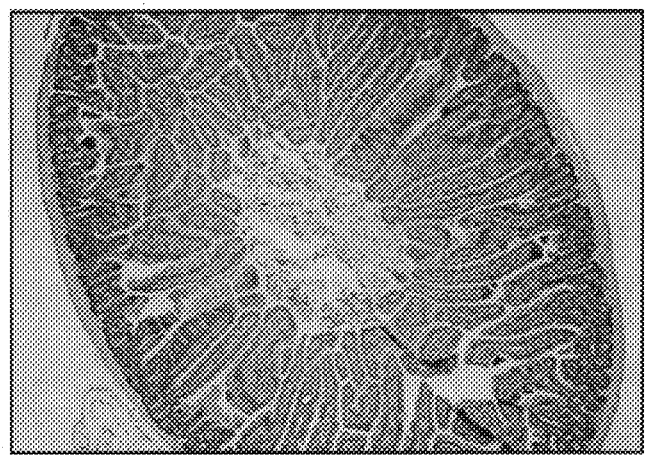
Figure 6C:
Figure 6D:
Figure 6E:
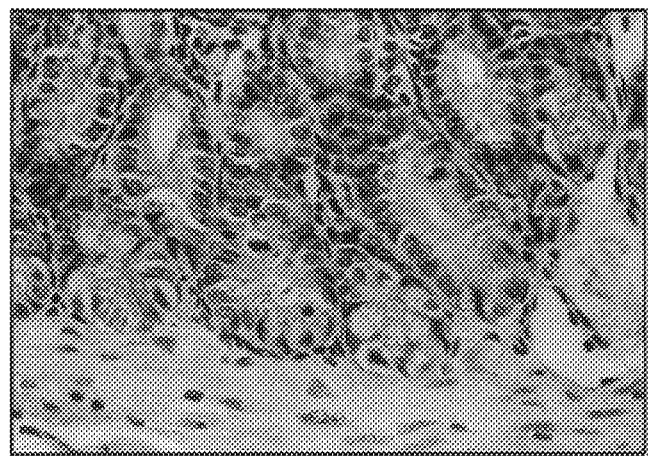
Figure 6F:
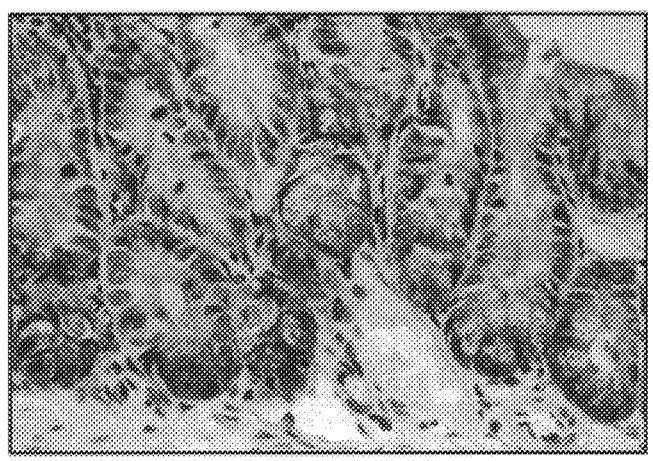

Mouse cryptdins 1–5 (SEQ ID NOS: 6 to 10) were purified from intestinal epithelial cells. In the presence of EDTA, the intestinal epithelium no longer adheres to the underlying basement membrane and floats free of the lamina propria upon gentle agitation (Bjerknes and Cheng, *Am. J. Anat.* 160:51–63 (1981), which is incorporated herein by reference). Preparations of epithelial sheets isolated in this manner were concentrated by low speed centrifugation and extracted with 30% formic acid. Peptides extracted from isolated epithelial sheets comigrate with cryptdins 1–5 (SEQ ID NOS: 6 to 10) when analyzed by acid-urea PAGE (FIG. 5), demonstrating their epithelial origin.

Immunoperoxidase staining of full-thickness sections of small intestine with an anti-cryptdin antibody demonstrate cryptdin antigen in Paneth cells, consistent with localization of cryptdin mRNA by in situ hybridization (Ouellette. et al., supra, (1989a)). Incubation of sections of adult mouse jejunum and ileum with a polyclonal anti-cryptdin IgG produced by rabbits immunized with the synthetic congener cryptdin C localized the immunoperoxidase reaction to granulated cells, morphologically defined as Paneth cells, at the base of every crypt (FIG. 6). The staining pattern accentuates the granular appearance of the cytoplasm in these cells and the immunoreactivity appears particularly strong over Paneth cell granules. The antibody is specific for mouse cryptdin(s), since it is negative both for rat and human Paneth cells (data not shown). Leukocytes in the lamina propria of the villi also were negative, suggesting that related enteric defensins are not expressed by phagocytes or lymphocytes. Because of the extensive similarity of mouse cryptdins 1–3 (FIG. 1; SEQ ID NOS: 6 to 8), the polyclonal antibody produced against cryptdin C probably recognizes the three peptides. Conversely, because mouse cryptdin 4 (SEQ ID NO: 9) and cryptdin 5 (SEQ ID NO: 10) differ markedly from the other mouse cryptdins, the anti-cryptdin C antibody is unlikely to react with cryptdin 4 (SEQ ID NO: 9) and cryptdin 5 (SEQ ID NO: 10), leaving their origin in Paneth cells somewhat unresolved.

Figure 4:
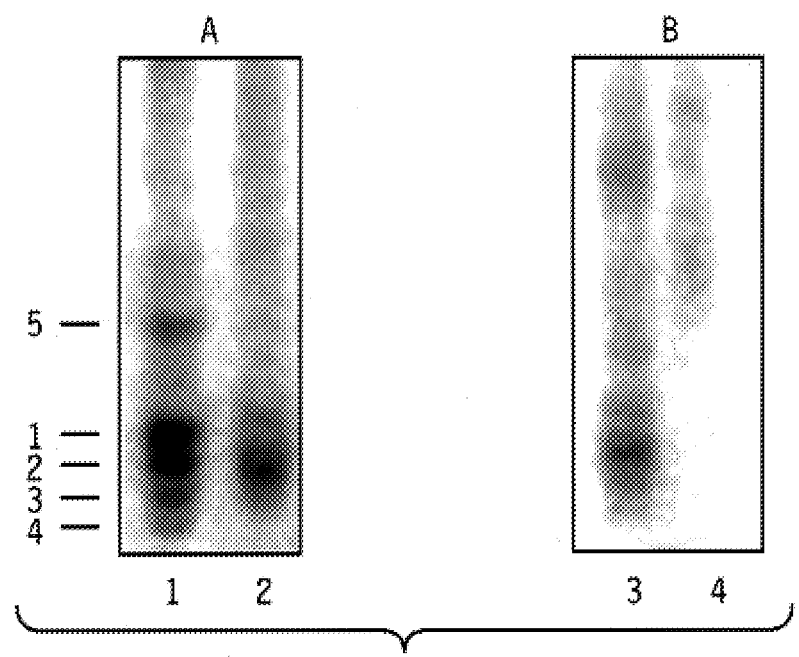
FIG. 4 compare mouse cryptdins 1–5 (SEQ ID NOS: 6 to 10, respectively) and partially purified luminal peptides.

Immunohistochemical data suggest cryptdins are secreted into the intestinal lumen. Material in the small intestinal lumen is strongly positive for the antibody but negative for pre-immune sera or IgG (FIGS. 6.A. and 6.B.). Although the agonist for Paneth cell defensin secretion is unknown, lysozyme, another protein constituent of Paneth cell granules, is secreted into the lumen under cholinergic regulation. Consistent with immunochemical detection of anti-cryptdin C positive material in the intestinal lumen, acid-urea PAGE of saline washes of adult jejunum and ileum contain peptides with mobilities very similar to but distinct from the mobility of cryptdins (FIG. 4). Nevertheless, the peptides are not identical to cryptdins 1–5 (SEQ ID NOS: 6 to 10, respectively) by either migration in acid-urea PAGE or by HPLC analysis, suggesting they may correspond to cryptdins that have been processed further. Conceivably, luminal cryptdin or cryptdin-like material could derive from exfoliated Paneth cells in the lumen, but the low rate of Paneth cell turnover suggests this is unlikely. The release of cryptdins or processed variants into the small bowel by Paneth cells contrasts with the apparent lack of defensin secretion by leukocytes, and it is inferred that a secretory pathway may exist for the constitutive delivery of defensins into the intestinal lumen by Paneth cells.

The antibacterial activity of purified mouse cryptdins 1–5 (SEQ ID NOS: 6–10) was tested against wild type and phoP mutant *S. typhimurium* using a modified plate diffusion assay (Lehrer et al., *J. Immunol. Methods* 137:167–173 (1991b), which is incorporated herein by reference). phoP is a two-component regulatory locus that is essential to *S. typhimurium* virulence and survival within macrophages (Fields et al., *Science* 243:1059–1062 (1989); Miller et al., *Proc. Natl. Acad. Sci., USA* 86:5054–5058 (1989), each of which is incorporated herein by reference). Mutants in the phoP locus are particularly sensitive to rabbit defensins NP-1 and NP-2 when compared to wild type parent strains (Fields et al., supra, 1989; Miller et al., *Infect. Immun.* 58:3706–3710, (1990), which is incorporated herein by reference).

Figure 7A:
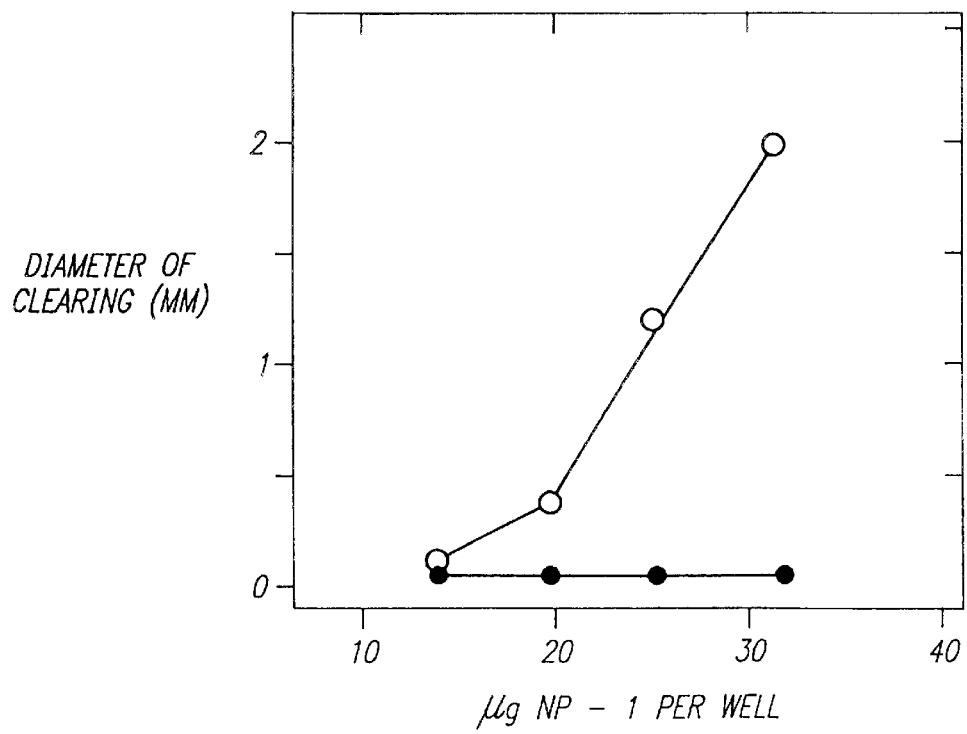
FIGS. 7.A. and 7.B. depict the antimicrobial activity of mouse cryptdin 1 (SEQ ID NO: 6). Samples of purified natural mouse cryptdin 1 (FIG. 7.A.) or rabbit NP-1 (FIG. 7.B.) were dissolved in 0.01% acetic acid and pipetted into wells produced in a 0.6% agarose/0.3% tryptone plate containing $1 \times 10^6$ log phase bacterial cells. After incubation at 37° C. for 18 hr, antimicrobial activity was evaluated by measuring the diameters of the clear zones. Closed circles denote wild type S. typhimurium; open circles denote the phoP$^-$ mutant.
Figure 7B:
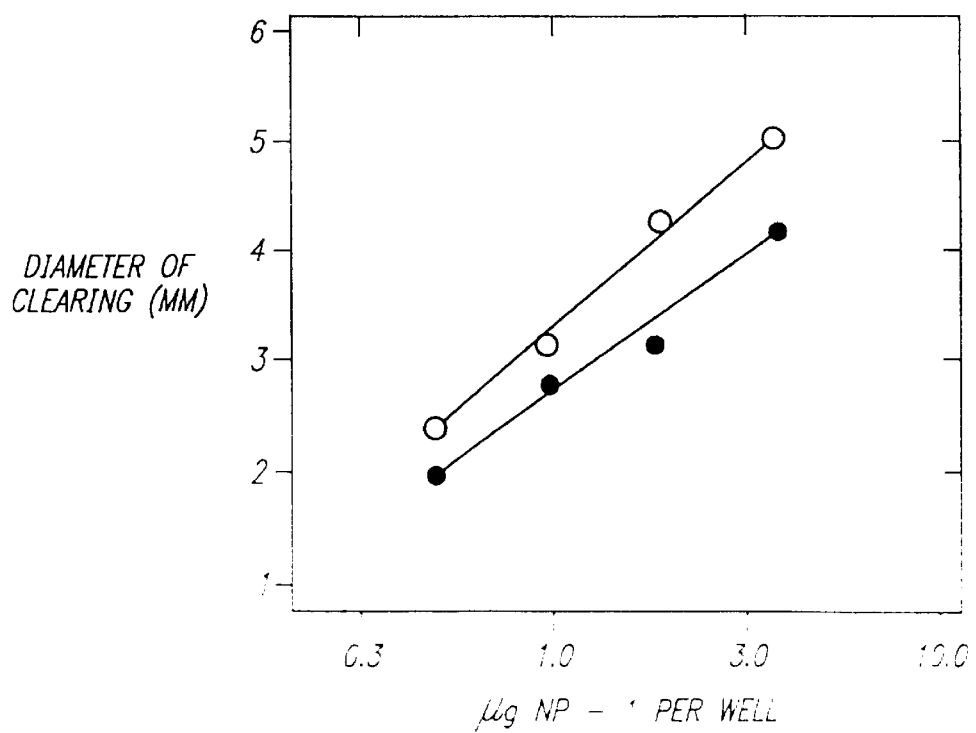

Under assay conditions using a phosphate buffer as described in Example III, the antimicrobial activity of rabbit defensin NP-1 against wild type and the phoP mutant organisms was quite similar (FIG. 7.B.). On the other hand, at concentrations of mouse cryptdin 1 (SEQ ID NO: 6) that are effective against the attenuated mutant, wild type *S. typhimurium* is completely resistant to the effects of the peptide (FIG. 7.A.).

The differential activity of cryptdin 1 (SEQ ID NO: 6) against avirulent *S. typhimurium* suggests that resistance to mucosal defensins may be important for the evolution of virulence in enteric pathogens. However, in experiments using HEPES or PIPES as buffers as described in Example III, concentrations of 100 µg/ml or 300 µg/ml cryptdin 1 were as effective as NP-1 in inhibiting the growth of wild type *S. typhimurium*. Furthermore, at these concentrations, cryptdins 4 and 5 were more effective than NP-1 in preventing the growth of mutant and wild type *S. typhimurium* (not shown).

Figure 10D:
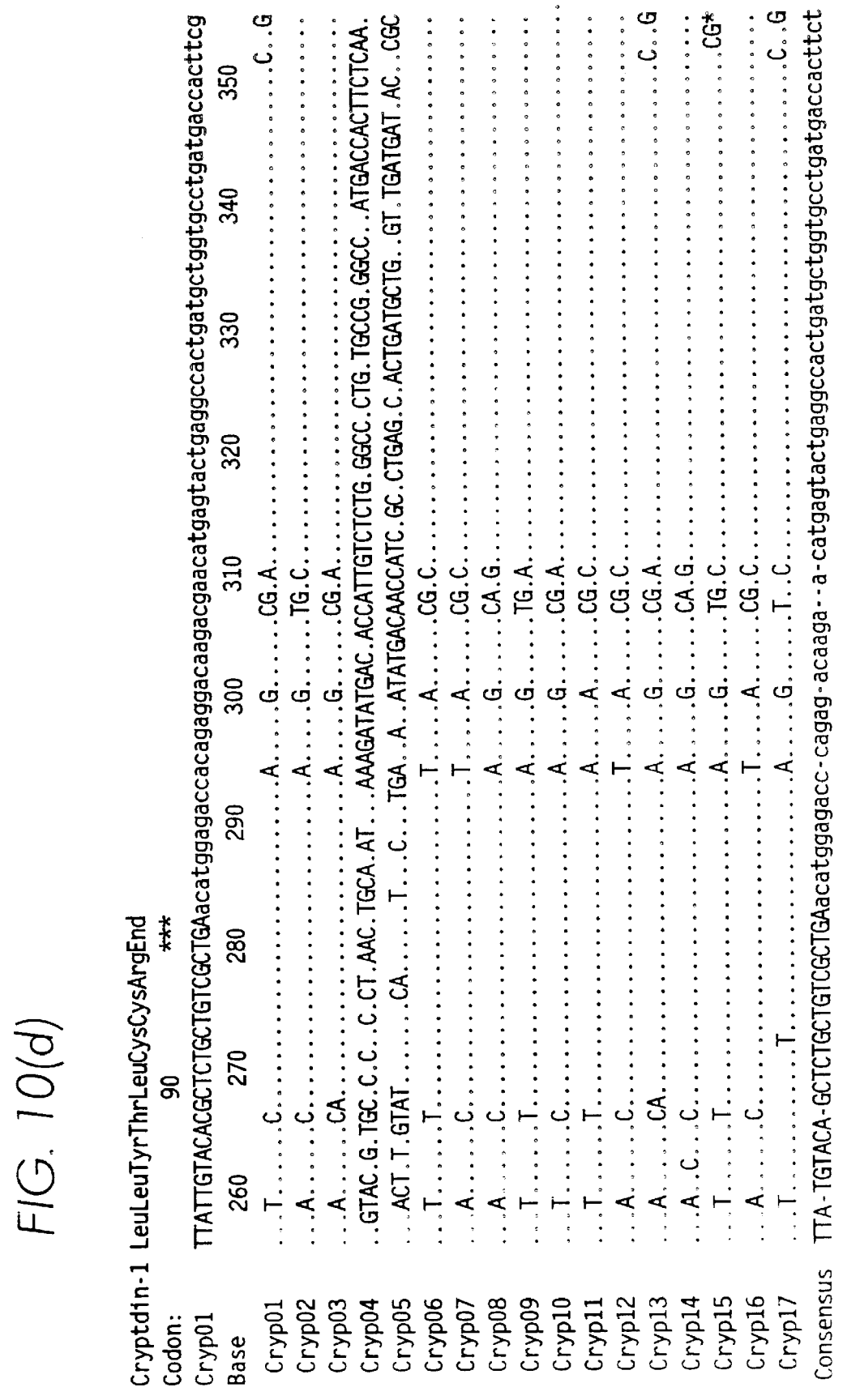

The present invention also provides substantially purified nucleic acid sequences encoding cryptdins. For example, the cDNA sequences for mouse cryptdins 1–17 (SEQ ID NOS: 40–56) are shown in FIG. 10 and the cDNA sequences for rat cryptdins 1–3 (SEQ ID NOS: 65–67) are shown in FIGS. 14.A. to 14.C. In addition, the genomic DNA sequences for mouse cryptdins 1, 2, 3, 5 and 6 (SEQ ID NOS: 58–62) and for an apparently inactivated cryptdin gene, cryptdin i (SEQ ID NO: 63) are shown in FIG. 11 and the genomic DNA sequences for rat cryptdins 1–3 (SEQ ID NOS: 68–70) are shown in FIGS. 15.A. to 15.C.

Figure 11B:
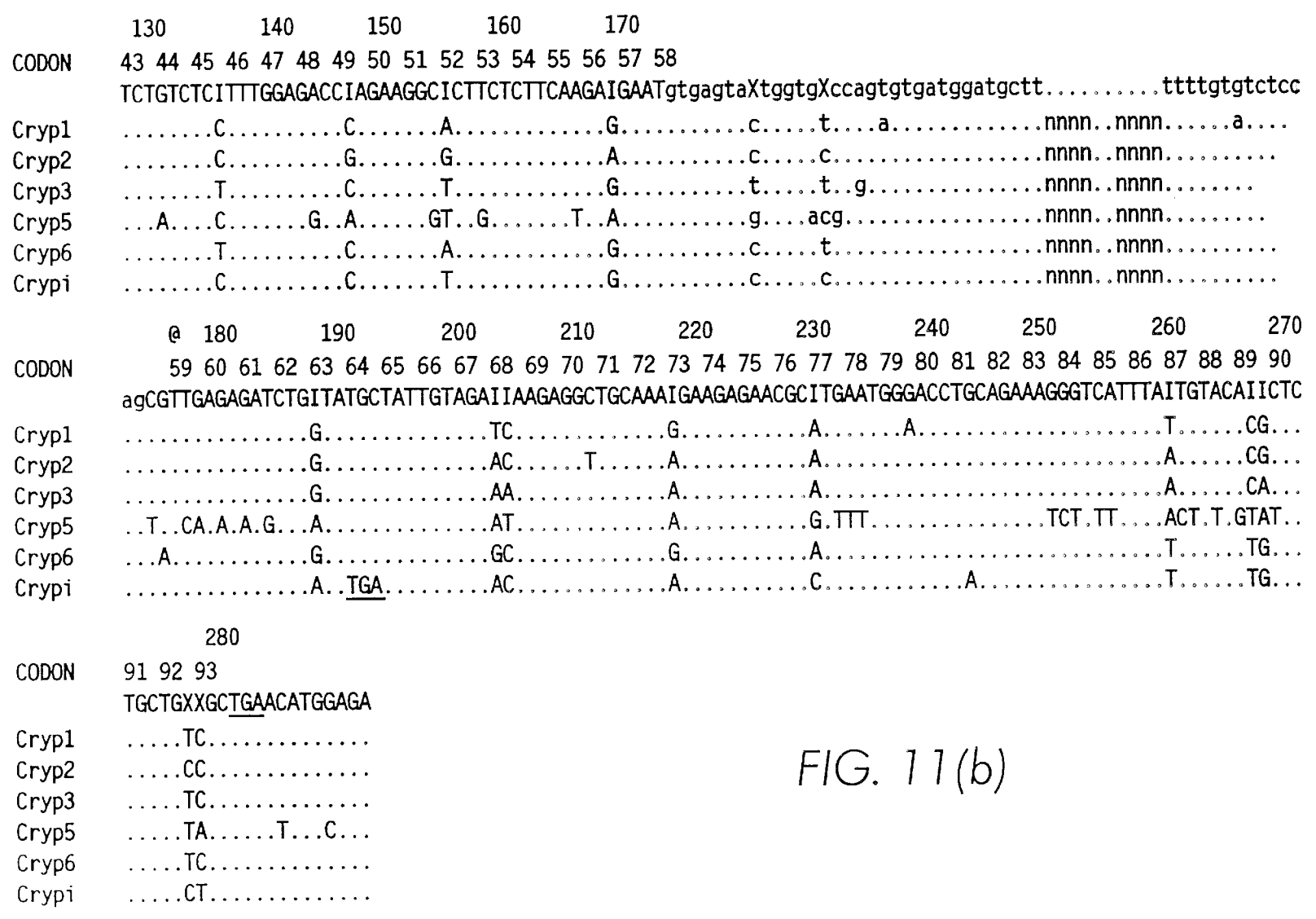

The skilled artisan would recognize that various nucleotide substitutions could be made in the nucleic acid sequences shown in FIGS. 10, 11 14. and 15 without altering the amino acid sequence of the encoded cryptdin peptide due to degeneracy of the genetic code. Such nucleotide sequences, which are equivalent to the sequences shown in FIGS. 10, 11, 14 and 15 are encompassed within the claimed invention.

The invention also provides nucleotide sequences that consist of a portion of a nucleic acid sequence as shown in FIGS. 10, 11, 14 and 15. Such a nucleotide sequence can be useful, for example, as a probe, which can hybridize under relatively stringent conditions to a nucleic acid molecule encoding a cryptdin peptide. For hybridization, such a nucleotide sequence should be at least about 10 nucleotides in length. One skilled in the art would know that appropriate conditions for hybridization can be determined empirically or can be calculated based, for example, on the G:C content of the nucleotide sequence, the length of the sequence and the number of mismatches, if any, between the probe and the target sequence (see, for example, Sambrook et al., *Molecular Cloning: A laboratory manual* (Cold Spring Harbor Laboratory Press 1989), which is incorporated herein by reference).

A nucleotide sequence as described above can be detectably labelled by attaching, for example, a radioactive label or biotin, or can be unlabelled. A labelled or unlabelled sequence also can be used as a primer for the polymerase chain reaction (PCR; see, for example, Erlich, *PCR Technology: Principles and applications for DNA amplification* (Stockton Press 1989), which is incorporated herein by reference). Such a sequence can be useful, for example, to identify a nucleic acid sequence encoding a cryptdin in a cell.

A nucleic acid molecule as shown in FIGS. 10, 11, 14 and 15 or a nucleotide sequence derived therefrom also can be useful, for example, for preparing a cryptdin peptide or a portion of a cryptdin peptide using well known methods of recombinant DNA technology. For example, the nucleic acid sequence can be cloned into an expression vector such as a baculovirus vector or a viral vector, which can infect a mammalian cell and express an encoded cryptdin peptide in the cell. Expression from such a vector can be useful for producing large amounts of a cryptdin, which can be used to treat a subject having an inflammatory pathology as described herein, or for producing a cryptdin directly in a subject. Thus, the invention provides vectors containing a nucleic acid molecule as shown in FIGS. 10, 11, 14 and 15 as well as specific host cells, in which the vector can propagate or can express a cryptdin.

The following examples are intended to illustrate but not limit the invention.

EXAMPLE I

Purification of Enteric Defensins

Outbred Swiss mice, (Crl:CD-1)(ICR)BR, 45 day old males (30–35 g) or timed-pregnant dams, were obtained from Charles River Breeding Laboratories, Inc. (North Wilmington Mass.). In studies of newborn mice, litters were culled to 8 pups within 12 hr of delivery. Mice were housed under 12 hr cycles of light and darkness and had free access to food and water.

Cryptdins were isolated by a modification of the method described by Selsted et al., *J. Cell. Biol.* 118:929–936 (1992); Ouellette et al., *Infect. Immun.* 62:5040–5057 (1994), each of which is incorporated herein by reference. Jejunal and ileal intestinal segments were excised from 60 mice immediately after carbon dioxide euthanasia. The tissue was washed and the lumen was flushed with ice cold water prior to homogenization in 500 ml ice cold 30% acetic acid. The homogenate was clarified by centrifugation, lyophilized, dissolved in 200 ml 30% acetic acid, clarified by filtration through Whatman 541 filter paper and applied to a 10×60 cm Bio-Gel P-60 column equilibrated with 30% acetic acid. The elution rate was 100 ml/hr. Fractions containing cryptdins were identified by electrophoresis in acid-urea polyacrylamide gels (Selsted and Harwig, *Infect. Immun.* 55:2281–2285 (1987), which is incorporated herein by reference).

Cryptdin-containing fractions were pooled and lyophilized, then purification was completed by RP-HPLC. Initial separation of mouse cryptdins 2–5 was achieved by HPLC on a 1×25 cm Vydac C-18 column using a gradient of water and acetonitrile containing 0.13% HFBA. Solvents were delivered at 3 ml/min to generate the following acetonitrile gradient: 0–28% (10 min); 28–34% (20 min); and 34–40% (60 min). Cryptdins 1 and 6, which coeluted under these conditions, were resolved by C-18 RP-HPLC using 0.1% TFA as the ion pair and a 16–21% acetonitrile gradient delivered in 35 min at 3 ml/min. To eliminate traces of residual HFBA, preparations of cryptdins 2–5 were subjected to an addition RP-HPLC step using 0.1% TFA. All peptides were lyophilized and quantitated by amino acid analysis prior to antimicrobial testing. Essentially identical methods were used to purify rat and human cryptdin peptides, except that rat cryptdins were isolated from the small intestine of adult Sprague-Dawley rats and human cryptdins were isolated from a surgically resected normal adult human male small intestine.

EXAMPLE II

Peptide Characterization

Amino acid analyses were performed on 6 N HCl hydrolysates (150° C., 2 hr) of unmodified or performic acid-oxidized peptides. Hydrolysates were derivatized with phenylisothiocyanate and the resulting phenylthiocarbamyl amino acids were quantitated as described previously (Selsted and Harwig, supra, 1987; Selsted et al., supra, 1992; Ouellette et al., *FEBS Lett.* 304:146–148 (1992), which is incorporated herein by reference). Peptide samples were reduced with dithiothreitol (DTT) and pyridylethylated with 4-vinyl pyridine for sequencing (Henschen, In *Advanced Methods in Protein Microsequence Analysis* (Wittmann-Liebold et al., pages 244–255 (1986), which is incorporated herein by reference). Sequence determinations were performed by automated Edman degradation on an ABI model 477 system (Applied Biosystems, Inc.; Foster City Calif.) with on-line PTH amino acid analysis. In some cases, the C-terminus of a cryptdin peptide was confirmed by amino acid analysis of chymotryptic peptides. Cryptdins 4 and 5 also were analyzed by positive-ion fast atom bombardment mass spectrometry on a VG 7070E-HF instrument (Ouellette et al., supra, 1994).

EXAMPLE III

Antimicrobial Assays

Antibacterial activity was measured in an agar radial diffusion assay (Lehrer et al., supra, 1991b) using wild type *S. typhimurium* (ATCC 10428) or an isogenic phoP mutant of *S. typhimurium* (strain CS015 phoP102::Tn10d-Cam, Miller et al., supra, 1989). Cells were grown to log phase in trypticase soy broth at 37° C., harvested by centrifugation and resuspended to $1\times10^7$ colony forming units (CFU) per ml in 10 mM sodium phosphate buffer (pH 7.4).

A 100 µl aliquot of each organism was mixed with 10 ml 1% agarose in 0.03% (w/v) trypticase soy medium, 10 mM sodium phosphate (pH 7.4) at 42° C. Five µl samples of peptide solution were pipetted into 3 mm diameter wells formed in the agarose with a sterile punch. After 3 hr at 37° C., the inoculated agarose plate was overlayed with 1% agarose containing 6% trypticase soy medium. After 12–16 hr, antimicrobial activity was apparent as clear zones surrounding wells loaded with antibacterial samples; the sizes of the clear zones were concentration-dependent.

Cryptdin antimicrobial activity in vitro was substantially enhanced in piperazine-N,N'-bis (2-ethane sulfonic acid) (PIPES) or in N-2-hydroxyethylpiperazine-N'-2-ethanesulfonic acid (HEPES) as compared to the activity in sodium phosphate. Purified cryptdin peptides were dissolved at 3 to 300 µg/ml in 0.01% acetic acid and activity was examined against *E. coli* ML35 (ATCC). In the radial diffusion assay, 5 µl peptide solution was transferred into wells formed in plates of 1% agarose buffered with 10 mM PIPES (pH 7.4) and containing $1\times10^6$ log-phase bacteria grown in trypticase soy broth. After 3 hr at 37° C., the plates were overlayed with 0.8% agarose containing 2× trypticase soy broth and incubated overnight. The antibacterial activities of cryptdin peptides was compared with the activity of rabbit neutrophil defensin NP-1, which was purified from peritoneal exudates as described by Selsted et al. (*J. Biol. Chem.* 260:4579–4584 (1985), which is incorporated herein by reference). Antibacterial activity was determined by measuring the diameter of clearing around each well and plotted as a function of peptide concentration.

As shown in FIG. 12, each cryptdin peptide produced a dose-dependent zone of clearing, which indicates that *E. coli* growth was inhibited. The potencies of the cryptdins varied, with cryptdins 1, 3 and 6 showing similar activity, which was about 3–5× greater than the activity of cryptdin 2. Cryptdin 5 was approximately 5× more active than rabbit NP-1 at concentration above 100 µg/ml (FIG. 12.C.) and cryptdin 4 was at least 50× more active than NP-1 when compared at 100 µg/ml and 300 µg/ml (FIG. 12.B.). These higher concentrations of cryptdins 4 and 5 also were more effective than the same concentration of NP-1 at inhibiting the growth of *S. aureus* and of wild type and mutant strains of *S. typhimurium* (not shown). These results demonstrate that various cryptdin peptides can inhibit bacterial growth.

In order to determine whether the effect of the cryptdin peptides against *E. coli* is bacteriostatic or bacteriocidal, bacterial killing was quantitated as a function of time. Bactericidal assays were performed by incubating $1-2\times10^6$ log-phase bacteria in 10 mM PIPES containing 10 µg peptide/ml. After incubation for 15 or 30 min at 37° C., aliquots were removed, serially diluted and plated on trypticase soy agar. Bactericidal activity was quantitated by counting colonies after overnight incubation at 37° C.

As shown in FIG. 13, cryptdins 1 and 3–6 rapidly killed the *E. coli* cells. In each of these cases, survival was reduced to less than 1% after only 15 min incubation. Cryptdin 2 was the only peptide tested that was not bactericidal under the assay condition. Cryptdins 2 and 3 differ only at amino acid position 10 (threonine and lysine, respectively).

The bactericidal activity of rat cryptdin 1 also was examined. *E. coli* ML35 cells, S. aureus 502A cells or mutant or wild type *S. typhimurium* cells were incubated with various concentrations of rat cryptdin 1 or rabbit NP-1. Ten µg/ml rat cryptdin 1 killed about 90% of the *S. aureus* cells and greater than 99% of the *E. coli* and mutant *S. typhimurium* cells, but was relatively ineffective in killing wild type *S. typhimurium* (not shown). Rat cryptdin 1 was more effective than NP-1 in killing the *E. coli* and mutant *S. typhimurium* cells, whereas NP-1 was more effective in killing *S. aureus*.

The effect of mouse cryptdins 1–3 and 6 at inhibiting the growth of the protozoan, *Giardia lamblia*, which is the most common cause of protozoan disease in the human small intestine, also was examined. Briefly, trophozoites of the C6 clone of *Giardia lamblia* WB (ATCC 30957) were grown to late log phase in TYI-S-33 medium containing bovine bile. Free-swimming trophozoites were discarded and tubes with attached trophozoites were refilled with warm Dulbecco's PBS. Trophozoites were detached by chilling 10 min on ice, then harvested by centrifugation, resuspended at $2 \times 10^7$/ml in 25 mM HEPES (pH 7.5) containing 9% (isotonic) sucrose and incubated for 2 hr at 37° C. with various concentrations of mouse cryptdins 1–3 or 6. Following incubation, trophozoite viability was determined by trypan blue exclusion.

The cryptdin peptides killed Giardia trophozoites in a dose-dependent manner (not shown). In particular, 20 μg/ml of cryptdin 2 or cryptdin 3 reduced Giardia growth by greater than 2 orders of magnitude (not shown). These results indicate that cryptdins are active against a variety of microorganisms.

EXAMPLE IV

Anti-cryptdin Antibody

A polyclonal rabbit antibody was prepared to a synthetic analogue of cryptdin 1. The peptide, termed cryptdin C, corresponding to residues 4–35 in cryptdin 1 (SEQ ID NO: 6; FIG. 1) was synthesized by solid phase chemistry using $N^\alpha$-butoxycarbonyl protection (Kent, *Ann. Rev. Biochem.* 57:957–989 (1988), which is incorporated herein by reference). Following cleavage/deprotection of synthetic cryptdin C with TFA-trifluoromethanesulfonic acid, the peptide was precipitated in ethyl ether and dried in vacuo. A 100 mg sample was dissolved in 10 ml 6.0 M guanidine-HCl, 0.2 M Tris-HCl, pH 8.2, containing 20 mg DTT. The sample was purged with nitrogen, heated to 50° C. for 4 hr and diluted 100-fold with deionized water, then was dialyzed exhaustively, first against 0.1 M sodium phosphate (pH 8.2), 20 mM guanidine-HCl, 100 mM NaCl, then against 5% acetic acid. The sample was lyophilized, dissolved in 10 ml 5% acetic acid and subjected to RP-HPLC on a 1×25 cm Vydac C-18 column. The earliest eluting peak, representing about 0.5% of the crude peptide, was determined by amino acid analysis to have the desired composition.

A sample (1.5 mg) of cryptdin C was supplied, without conjugation to carrier, to Berkeley Antibody Company (Berkeley, Calif.) for immunization of 2 New Zealand White rabbits. Serum samples were collected for 12 weeks, until the anti-cryptdin C titer, determined by ELISA, reached about 1:10,000 for each rabbit. IgG was isolated from antiserum using DEAE Econo-Pac chromatography (Bio-Rad; Richmond Calif.) as described by the manufacturer.

EXAMPLE V

Immunohistochemistry

Paraffin sections of formalin-fixed mouse mid-small bowel were deparaffinized, treated with 1.1% hydrogen peroxide for 40 min, then washed extensively with water followed by PBS. Slides were treated for 20 min at 37° C. with 500 μg/ml trypsin in PBS, washed twice with PBS, and blocked by incubation for 20 min with 5% porcine serum. Slides were incubated for 20 min in rabbit anti-cryptdin IgG (1:10 dilution relative to serum IgG concentration), then washed with blocking serum. Porcine anti-rabbit IgG was used as linking reagent between the primary antibody and rabbit antiperoxidase-peroxidase conjugate (Dako; Carpinteria Calif.). Diaminobenzidine was used as peroxidase substrate and parallel incubations were performed using equivalent dilutions of rabbit preimmune IgG as the primary antibody.

EXAMPLE VI

Preparation of Synthetic Cryptdin 1

This example provides a method for synthesizing, purifying and characterizing synthetic cryptdin 1.

A. Synthesis

Synthesis was initiated at the 0.13 mmole scale using Wang resin coupled to flourenylmethoxycarbonyl (Fmoc)-arginine using an acid labile linker. Synthesis was carried out in dimethylformamide (DMF) using (relative to resin substitution) a 3-fold excess of Fmoc-amino acids activated in situ with a 3-fold excess of BOP (benzotriazol-1-yl-oxy-tris (dimethylamino) phosphonium hexafluorophosphate) and HOBt (hydroxybenzotriazole) and a 6-fold molar excess of N-methylmorpholine (Nmm). Fmoc removal during synthetic cycles was achieved using cycles of 50% and 25% piperidine in DMF. The side-chain protection scheme utilized the following Fmoc-amino acids: OtBut-aspartic acid, Pmc-arginine, tBut-tyrosine, tBut-serine, Trt-cysteine, tBoc-lysine, OtBut-glutamic acid, Trt-asparagine, tBut-threonine and Trt-histidine.

The peptide chain was assembled in a Synostat batch synthesizer using single couplings at all additions except at leucine and valine which were double coupled. The cycle sequence is as follows:

1. Wash with DMF 4× for 2 min;
2. Deblock: 50% piperidine 1× for 5 min;
3. Deblock: 25% piperidine 1× for 15 min;
4. Wash with DMF 4× for 2 min;
5. Dissolve amino acids+BOP+HOBt in DMF and transfer to reaction vessel;
6. Add Nmm to RV and mix for 60 min; and
7. Wash with DMF 1× for 2 min.

After coupling of the amino terminal residue, the terminal Fmoc group was removed using the following cycle:

1. Wash with DMF 4× for 2 min;
2. Deblock: 50% piperidine 1× for 5 min;
3. Deblock: 25% piperidine 1× for 15 min;
4. Wash with DMF 4× for 2 min;
5. Wash with dichloromethane 1× for 5 min;
6. Wash with isopropanol 4× for 5 min;
7. Dry under stream of $N_2$ 1× for 10–20 min; and
8. Dry under vacuum 1× for 12 hr.

The peptide-resin was weighed to determine mass increase. To cleave and deprotect the peptide-resin, it was first reswelled in dichloromethane, then cleaved and deprotected by addition of reagent R (90% trifluoroacetic acid, 5% thioanisole, 3% ethanedithiol, 2% anisole) at a ratio of 10 ml/g peptide-resin. Cleavage/deprotection was carried out under nitrogen for 18 hr at RT.

B. Purification

The cleavage mixture was separated from resin by filtration through a scintered glass funnel, washed with 1–2 ml fresh reagent R and diluted 5-fold with 50% acetic acid. Glacial acetic acid was added to a final acetic acid concentration of 50%. The resulting solution was extracted 3× with 0.33 vol methylene chloride and the aqueous phase was lyophilized to dryness, then dissolved in 50% acetic acid and relyophilized. The extraction and lyophilization steps were repeated 3–4 times, then the dry peptide was dissolved in 30% acetic acid at a concentration of 20 mg/ml and passed over an 800 ml Sephadex G-10 column equilibrated in 30% acetic acid. Peptide-containing fractions were pooled, lyophilized, dissolved in 5% acetic acid, then diluted tenfold with water to a final protein concentration of about 1 mg/ml. The solution was adjusted to pH 8.0 with ammonium hydroxide and mixed rapidly with a magnetic stirrer at RT in a beaker open to room air. The pH was adjusted periodically to pH 8.0 over a period of 4 days. The solution was then acidified with acetic acid to pH 3.5 and lyophilized.

C-18 RP-HPLC using 0.1% TFA-water/acetonitrile gradients was used to purify the folded peptide. Fractions were analyzed on acid-urea gels and compared to natural cryptdin 1. The yield from an initial crude peptide preparation of 500 mg was approximately 30 mg.

C. Characterization

Synthetic cryptdin 1 was compared to natural peptide on analytical RP-HPLC, SDS-PAGE and under three different conditions on acid-urea PAGE. For analysis on acid-urea PAGE, peptide was electrophoresed either without modification, after reduction with DTT or after performic acid oxidation. Under all conditions described, native and synthetic cryptdin 1 behaved identically. The amino acid compositions of natural and synthetic cryptdin 1 were indistinguishable.

EXAMPLE VII

Cloning of Nucleic Acid Molecules Encoding Cryptdins

Individual crypts were isolated using a modification of the EDTA elution method of Bjerknes and Cheng, supra, 1981, as described by Cano-Gauci et al., *Expt. Cell Res.* 208:344–349 (1993), which is incorporated herein by reference. Briefly, the central 10 cm of small intestine from an adult C3H/HeJ mouse was everted on a Buchler gradient-making apparatus, then intact crypts were dislodged by vibration in ice cold 30 mM EDTA in calcium-free, magnesium-free PBS. Isolated crypts were disrupted in a sonicating water bath prior to cDNA synthesis.

The crypt library was constructed by MRNA-directed PCR amplification (Cano-Gauci et al., supra, 1992). Phage were screened at a density of approximately 300 PFU/dish using the partial cDNA clone, asb4/134, as a probe (Ouellette et al., supra, 1989a). Positive phage were collected and denatured plasmid cDNA was sequenced by the dideoxynucleotide termination method using Sequenase™ (U.S. Biochemical Corp.; Cleveland Ohio). Sequencing primers included T3 and T7 promoter primers and Defcr$_{p130}$, which is a 16-mer that corresponds to nucleotides 90–105 in cryptdin 1 MRNA (Huttner et al., *Genomics* 19: 448–453 (1994), which is incorporated herein by reference). Reaction mixtures were separated by electrophoresis in gels consisting of 5% Long Ranger™ (AT Biochem, Inc.; Malvern Pa.) and DNA sequence data were analyzed (Ouellette et al., supra, 1994). Computations for similarity searches of DNA sequences in nonredundant nucleic acid and protein sequence databases were performed at the National Center for Biotechnology Information with the BLAST network service (Ouellette et al., supra, 1994).

A cDNA library also was prepared by amplification of cryptdin mRNA (Huttner et al., supra, 1994). Total RNA was isolated from the small intestine of a male 129/SVJ mouse using RNazol™ (Biotecx Lab; Houston Tex.). First strand cDNA synthesis was performed using the cDNA Cycle Kit (Invitrogen; San Diego Calif.). Amplification of 5' ends was performed using the 5' RACE method (Frohman et al., *Proc. Natl. Acad. Sci., USA* 85:8998–9002 (1988), which is incorporated herein by reference) with a reverse primer that was specific for a conserved region of the cryptdin 3'-untranslated sequence (UTS).

Blot hybridization of the PCR products using an oligonucleotide probe specific for the cryptdin prepro-coding region detected a single band. DNA from the band was isolated using the Geneclean II™ kit (Bio101; La Jolla Calif.), subcloned into the Bluescript II plasmid using the pCR-Script SK(+) cloning kit (Stratagene) and transfected into competent XL-1 Blue cells (Stratagene). Colonies containing cryptdin-related sequences were identified by hybridization to a labelled asb4/134 probe. DNA sequence analysis of the positive clones was performed as described above, except that internal primers were utilized as required.

Using these methods, cDNA sequences encoding 17 distinct mouse cryptdin peptides were identified (FIG. 10; SEQ ID NOS: 40–56). The various mouse cryptdin cDNA sequences share 93–100% nucleotide sequence identity with cryptdin 1, except cryptdin 5 and cryptdin 4 share 73% and 69% sequence identity, respectively, with cryptdin 1.

The amino acid sequences were deduced from the cDNA sequences for the 17 mouse cryptdins (see FIG. 9.A.; SEQ ID NOS: 23 to 39). As shown in FIG. 9.A., the cDNA sequences encode prepro-cryptdin peptides consisting of a signal peptide, a propiece and the cryptdin peptide. The prepro-cryptdins, including the mature cryptdin peptide, share significant amino acid sequence identity with cryptdin 1, although cryptdins 4 and 5 are less homologous (FIG. 9.B.). Amino acid variability was most striking at position 10 of the mature cryptdin peptide, where either serine, threonine, alanine, isoleucine or lysine can be found. Interestingly, a single nucleotide change in the sequence of cryptdin 2 can account for each of these amino acids. In addition, position 15 can contain arginine or lysine. The amino acid variability among cryptdin peptides can be involved in conferring different antimicrobial properties to the cryptdins.

Mouse cryptdin genomic clones also were obtained and sequenced (Huttner et al., supra, 1994). Asb4/134 was used as a probe to screen a custom-made 129/SVJ mouse genomic library constructed in lambda DASH II (Stratagene Cloning Systems, Inc.; La Jolla Calif.). Approximately $1 \times 10^6$ phage were screened in duplicate and 25 positive phage were identified. Ten clones were purified and phage DNA was isolated using Qiagen 100 columns (Qiagen, Inc.; Chatsworth Calif.). Southern blots of Eco RI-digested DNA from individual phage were hybridized to asb4/134 and hybridizing fragments were subcloned into Bluescript II SK$^+$™ (Stratagene) or pUC18 (BRL; Gaithersburg Md.) for sequencing.

Sequencing was performed as described above, except that primers were selected based on the cryptdin 1 cDNA sequence and with the expectation that mouse cryptdin genes would be structurally homologous to the rabbit MCP-1 and MCP-2 defensin genes (see Huttner et al., supra, 1994). DNA sequence data were analyzed using the programs of Staden (*Biochem. Soc. Trans.* 12:1005–1008 (1984) and the University of Wisconsin Genetics Computer Group (Devereux et al., *Nucl. Acids Res.* 12:387–395 (1985)). Searches for homology were performed as described above.

As shown in FIG. 11, screening of the genomic library produced nucleic acid sequences that contained the complete coding sequences for mouse cryptdins 1, 2, 3, 5 and 6 (SEQ ID NOS: 58–62). In addition, a homologous gene, designated cryptdin i (Crypi; SEQ ID NO: 63), which apparently was inactivated due to a point mutation that changed a cysteine codon to an in-frame stop codon, was isolated. Examination of the nucleic acid sequences revealed that the cryptdin genes contain two exons, the first of which codes for the 5'-UTS and the prepro-coding region and the second of which encodes the mature cryptdin peptide and the 3'-UTS (not shown; but see FIG. 11.A.). A similar structure has been described for the human cryptdin genes (Jones and Bevins, *J. Biol. Chem.* 267:23216–23225 (1992)).

Similar methods as described above were used to obtain the cDNA sequences encoding rat cryptdins 1–3 (FIGS. 14.A. to 14.C.; SEQ ID NOS: 65–67, respectively), except that RNA was obtained from the small intestine of Sprague-Dawley rats. In addition, genomic DNA sequences encoding rat cryptdins 1–3 (FIGS. 15.A. to 15.C.; SEQ ID NOS: 68–70, respectively) were obtained using methods as described above, except that a genomic library containing Sprague-Dawley DNA cloned in EMBL3 was purchased from Clontech (Palo Alto Calif.).

Although the invention has been described with reference to the disclosed embodiments, it should be understood that various modifications can be made without departing from the spirit of the invention. Accordingly, the invention is limited only by the following claims.

We claim:

1. A substantially purified human or rat cryptdin peptide of enteric origin having an amino acid sequence as follows:

$X_1$-C-$X_2$-C-R-$X_3$-C-$X_4$-E-$X_5$-C-$X_6$-C-C-$X_7$ wherein $X_1$ is 3 to 9 amino acids;
$X_2$ is 1 amino acid;
$X_3$ is 2 or 3 amino acids;
$X_4$ is 3 amino acids;
$X_5$ is 5 amino acids;
$X_6$ is 6 to 10 amino acids; and
$X_7$ is 0 to 9 amino acids.

2. A substantially purified mouse cryptdin peptide of enteric origin having an amino acid sequence as follows:

$X_1$-L-$X_2$-C-Y-C-R-$X_3$-C-K-$X_4$-E-$X_5$-G-T-C-$X_6$-C-C-$X_7$ wherein $X_1$ is 1, 3 or 4 amino acids;
$X_2$ is 1 amino acid;
$X_3$ is 3 amino acids;
$X_4$ is 2 amino acids;
$X_5$ is 3 amino acids;
$X_6$ is 6 to 9 amino acids; and
$X_7$ is 0 to 3 amino acids.

3. The substantially purified cryptdin peptide of claim 2, wherein $X_1$ is selected from the groups consisting of LRD, G and LSKK (SEQ ID NO: 1).

4. The substantially purified cryptdin of claim 2, wherein $X_2$ is selected from the group consisting of V, L and I.

5. The substantially purified cryptdin of claim 2, wherein $X_3$ is selected from the group consisting of KGH and *RG, wherein * is selected from the group consisting of S, T, K, I and A.

6. The substantially purified cryptdin of claim 2, wherein $X_4$ is selected from the group consisting of GR, RR and RG.

7. The substantially purified cryptdin of claim 2, wherein $X_5$ is selected from the group consisting of RMN, RVR, RVF, HMN and HIN.

8. The substantially purified cryptdin of claim 2, wherein $X_6$ is selected from the group consisting of GIRFLY (SEQ ID NO: 2), RNLFLTFVF (SEQ ID NO: 3), RRGHLMYTL (SEQ ID NO: 4) and RKGHL*YT* (SEQ ID NO: 5), wherein * indicates L or M independently.

9. The substantially purified cryptdin of claim 2, wherein $X_7$ is selected from the group consisting of R, S and PRR.

10. The substantially purified cryptdin of claim 2, wherein the amino acid sequences $X_1$, L, $X_2$ are absent.

11. A substantially purified cryptdin peptide of enteric origin having an amino acid sequence selected from the group consisting of:

GLLCYCRKGHCKRGERVRGTCGIRFLYCCPRR (SEQ ID NO: 12);

LSKKLICYCRIRGCKRRERVFGTCRNLFLTFVFCCS (SEQ ID NO: 13);

LRDLVCYCRARGCKGRERMNGTCRKGHL-LYMLCCR (SEQ ID NO: 14);

LKQCHCRKFCRPYEKAEGSCR-PGLFIKRKICCIQQWTPGRT (SEQ ID NO: 15);

IGRPVRRCRCRANCGPKEYATAFCAQG-PFKQFKFCCT (SEQ ID NO: 16);

IRWPWKRCHCRSFCRPYENATSF-CAQGLFKQHKFCCLDTWPPRMK (SEQ ID NO: 10);

TSGSQARATCYCRTGRCATRESLSGV-CEISGRLYRLCCR (SEQ ID NO: 18); and

AFTCHCRRSCYSTEYSYGTCTVMGINHRFCCL (SEQ ID NO: 19).

12. A substantially purified cryptdin peptide having the following characteristics:
   a) expressed endogenously in epithelial cells of the small intestine;
   b) having a cationic charge;
   c) consisting of 30 to 45 amino acids in length;
   d) consisting of three to nine amino acids N-terminal to the first cysteine residue; and
   e) exhibiting antimicrobial activity against intestinal pathogens and opportunistic pathogens.

13. A composition, comprising a cryptdin peptide selected from the group consisting of the cryptdin peptides of claim 1, claim 2 and claim 12 and a physiologically acceptable carrier.

14. A method of inhibiting microbial growth in the intestine in a subject, comprising administering a cryptdin peptide selected from the group consisting of the cryptdin peptides of claim 1, claim 2 and claim 12 to the subject.

15. The method of claim 14, wherein said subject is immunocompromised.

16. The method of claim 15, wherein said subject is immunocompromised due to malignancy, malnutrition, radiation burns, immunosuppressive infections, autoimmune disease or neonatality, bone marrow transplantation or chemotherapy.

17. The method of claim 14, wherein said cryptdin is administered by a means selected from the group consisting of oral administration, nasogastric intubation, transabdominal catheterization, intravenous administration, aerosol inhalation and topical administration.

18. The method of claim 14, wherein more than one cryptdin is administered simultaneously or sequentially.

19. The method of claim 14, wherein said cryptdin is administered orally in a delayed release formulation designed to permit release in the small intestine.

20. A method for inhibiting microbial growth in a subject as a result of surgery, comprising administering a cryptdin selected from the group consisting of the cryptdin peptides of claim 1, claim 2 and claim 12 to said subject prior to said surgery.

* * * * *

UNITED STATES PATENT AND TRADEMARK OFFICE
CERTIFICATE OF CORRECTION

PATENT NO.   : 5,844,072
DATED         : December 1, 1998
INVENTOR(S)  : Selsted et al.

It is certified that error appears in the above-identified patent and that said Letters Patent is hereby corrected as shown below:

Title page,
Item [73], after "Calif." please insert -- The Shriner's Hospital for Crippled Children, Tampa, Fla. --

Column 10,
Line 11, please delete "MRNA" and replace with -- mRNA --.
Line 20, please delete "MRNA" and replace with -- mRNA --.

Column 17,
Line 43, please delete "MRNA" and replace with -- mRNA --.
Line 53, please delete "MRNA" and replace with -- mRNA --.

Signed and Sealed this

Fourteenth Day of January, 2003

JAMES E. ROGAN
*Director of the United States Patent and Trademark Office*

SEQUENCE LISTING ( 1 ) GENERAL INFORMATION:

( i i i ) NUMBER OF SEQUENCES: 70

( 2 ) INFORMATION FOR SEQ ID NO:1:

( i ) SEQUENCE CHARACTERISTICS:
( A ) LENGTH: 4 amino acids
( B ) TYPE: amino acid
( D ) TOPOLOGY: linear ( x i ) SEQUENCE DESCRIPTION: SEQ ID NO:1:

Leu Ser Lys Lys
1

( 2 ) INFORMATION FOR SEQ ID NO:2:

( i ) SEQUENCE CHARACTERISTICS:
( A ) LENGTH: 6 amino acids
( B ) TYPE: amino acid
( D ) TOPOLOGY: linear ( x i ) SEQUENCE DESCRIPTION: SEQ ID NO:2:

Gly Ile Arg Phe Leu Tyr
1               5

( 2 ) INFORMATION FOR SEQ ID NO:3:

( i ) SEQUENCE CHARACTERISTICS:
( A ) LENGTH: 9 amino acids
( B ) TYPE: amino acid
( D ) TOPOLOGY: linear ( x i ) SEQUENCE DESCRIPTION: SEQ ID NO:3:

Arg Asn Leu Phe Leu Thr Phe Val Phe
1               5

( 2 ) INFORMATION FOR SEQ ID NO:4:

( i ) SEQUENCE CHARACTERISTICS:
( A ) LENGTH: 9 amino acids
( B ) TYPE: amino acid
( D ) TOPOLOGY: linear ( x i ) SEQUENCE DESCRIPTION: SEQ ID NO:4:

Arg Arg Gly His Leu Met Tyr Thr Leu
1               5

( 2 ) INFORMATION FOR SEQ ID NO:5:

(i) SEQUENCE CHARACTERISTICS:
     (A) LENGTH: 9 amino acids
     (B) TYPE: amino acid
     (D) TOPOLOGY: linear (ix) FEATURE:
     (A) NAME/KEY: Peptide
     (B) LOCATION: 6
     (D) OTHER INFORMATION: /note= "Xaa = Amino acid is independently L or M."

(ix) FEATURE:
     (A) NAME/KEY: Peptide
     (B) LOCATION: 9
     (D) OTHER INFORMATION: /note= "Xaa = Amino acid is independently L or M"

(xi) SEQUENCE DESCRIPTION: SEQ ID NO:5:

Arg Lys Gly His Leu Xaa Tyr Thr Xaa
1               5

(2) INFORMATION FOR SEQ ID NO:6:

(i) SEQUENCE CHARACTERISTICS:
     (A) LENGTH: 35 amino acids
     (B) TYPE: amino acid
     (D) TOPOLOGY: linear (xi) SEQUENCE DESCRIPTION: SEQ ID NO:6:

Leu Arg Asp Leu Val Cys Tyr Cys Arg Ser Arg Gly Cys Lys Gly Arg
1               5                   10                  15

Glu Arg Met Asn Gly Thr Cys Arg Lys Gly His Leu Leu Tyr Thr Leu
                20                  25                  30

Cys Cys Arg
        35

(2) INFORMATION FOR SEQ ID NO:7:

(i) SEQUENCE CHARACTERISTICS:
     (A) LENGTH: 35 amino acids
     (B) TYPE: amino acid
     (D) TOPOLOGY: linear (xi) SEQUENCE DESCRIPTION: SEQ ID NO:7:

Leu Arg Asp Leu Val Cys Tyr Cys Arg Thr Arg Gly Cys Lys Arg Arg
1               5                   10                  15

Glu Arg Met Asn Gly Thr Cys Arg Lys Gly His Leu Met Tyr Thr Leu
                20                  25                  30

Cys Cys Arg
        35

(2) INFORMATION FOR SEQ ID NO:8:

(i) SEQUENCE CHARACTERISTICS:
     (A) LENGTH: 35 amino acids
     (B) TYPE: amino acid
     (D) TOPOLOGY: linear (xi) SEQUENCE DESCRIPTION: SEQ ID NO:8:

Leu Arg Asp Leu Val Cys Tyr Cys Arg Lys Arg Gly Cys Lys Arg Arg
1               5                   10                  15

Glu Arg Met Asn Gly Thr Cys Arg Lys Gly His Leu Met Tyr Thr Leu
                20                  25                  30

Cys Cys Arg
        35

( 2 ) INFORMATION FOR SEQ ID NO:9:

( i ) SEQUENCE CHARACTERISTICS:
        ( A ) LENGTH: 31 amino acids
        ( B ) TYPE: amino acid
        ( D ) TOPOLOGY: linear ( x i ) SEQUENCE DESCRIPTION: SEQ ID NO:9:

```
Gly Leu Leu Cys Tyr Cys Arg Lys Gly His Cys Lys Arg Gly Glu Arg
 1               5                  10                  15
Val Arg Gly Thr Cys Gly Ile Arg Phe Leu Tyr Cys Cys Pro Arg
             20                  25                  30
```

( 2 ) INFORMATION FOR SEQ ID NO:10:

( i ) SEQUENCE CHARACTERISTICS:
        ( A ) LENGTH: 35 amino acids
        ( B ) TYPE: amino acid
        ( D ) TOPOLOGY: linear ( x i ) SEQUENCE DESCRIPTION: SEQ ID NO:10:

```
Leu Ser Lys Lys Leu Ile Cys Tyr Cys Arg Ile Arg Gly Cys Lys Arg
 1               5                  10                  15
Arg Glu Arg Val Phe Gly Thr Cys Arg Asn Leu Phe Leu Thr Phe Val
             20                  25                  30
Phe Cys Cys
         35
```

( 2 ) INFORMATION FOR SEQ ID NO:11:

( i ) SEQUENCE CHARACTERISTICS:
        ( A ) LENGTH: 39 amino acids
        ( B ) TYPE: amino acid
        ( D ) TOPOLOGY: linear ( x i ) SEQUENCE DESCRIPTION: SEQ ID NO:11:

```
Leu Lys Gln Cys His Cys Arg Lys Phe Cys Arg Pro Tyr Glu Lys Ala
 1               5                  10                  15
Glu Gly Ser Cys Arg Pro Gly Leu Phe Ile Lys Arg Lys Ile Cys Cys
             20                  25                  30
Ile Gln Gln Trp Thr Pro Gly
             35
```

( 2 ) INFORMATION FOR SEQ ID NO:12:

( i ) SEQUENCE CHARACTERISTICS:
        ( A ) LENGTH: 32 amino acids
        ( B ) TYPE: amino acid
        ( D ) TOPOLOGY: linear ( x i ) SEQUENCE DESCRIPTION: SEQ ID NO:12:

```
Gly Leu Leu Cys Tyr Cys Arg Lys Gly His Cys Lys Arg Gly Glu Arg
 1               5                  10                  15
Val Arg Gly Thr Cys Gly Ile Arg Phe Leu Tyr Cys Cys Pro Arg Arg
             20                  25                  30
```

( 2 ) INFORMATION FOR SEQ ID NO:13:

( i ) SEQUENCE CHARACTERISTICS:
        ( A ) LENGTH: 36 amino acids
        ( B ) TYPE: amino acid
        ( D ) TOPOLOGY: linear ( x i ) SEQUENCE DESCRIPTION: SEQ ID NO:13:

```
Leu  Ser  Lys  Lys  Leu  Ile  Cys  Tyr  Cys  Arg  Ile  Arg  Gly  Cys  Lys  Arg
1                   5                        10                      15

Arg  Glu  Arg  Val  Phe  Gly  Thr  Cys  Arg  Asn  Leu  Phe  Leu  Thr  Phe  Val
                20                       25                      30

Phe  Cys  Cys  Ser
               35
```

( 2 ) INFORMATION FOR SEQ ID NO:14:

( i ) SEQUENCE CHARACTERISTICS:
        ( A ) LENGTH: 35 amino acids
        ( B ) TYPE: amino acid
        ( D ) TOPOLOGY: linear ( x i ) SEQUENCE DESCRIPTION: SEQ ID NO:14:

```
Leu  Arg  Asp  Leu  Val  Cys  Tyr  Cys  Arg  Ala  Arg  Gly  Cys  Lys  Gly  Arg
1                   5                        10                      15

Glu  Arg  Met  Asn  Gly  Thr  Cys  Arg  Lys  Gly  His  Leu  Leu  Tyr  Met  Leu
                20                       25                      30

Cys  Cys  Arg
          35
```

( 2 ) INFORMATION FOR SEQ ID NO:15:

( i ) SEQUENCE CHARACTERISTICS:
        ( A ) LENGTH: 41 amino acids
        ( B ) TYPE: amino acid
        ( D ) TOPOLOGY: linear ( x i ) SEQUENCE DESCRIPTION: SEQ ID NO:15:

```
Leu  Lys  Gln  Cys  His  Cys  Arg  Lys  Phe  Cys  Arg  Pro  Tyr  Glu  Lys  Ala
1                   5                        10                      15

Glu  Gly  Ser  Cys  Arg  Pro  Gly  Leu  Phe  Ile  Lys  Arg  Lys  Ile  Cys  Cys
                20                       25                      30

Ile  Gln  Gln  Trp  Thr  Pro  Gly  Arg  Thr
          35                       40
```

( 2 ) INFORMATION FOR SEQ ID NO:16:

( i ) SEQUENCE CHARACTERISTICS:
        ( A ) LENGTH: 37 amino acids
        ( B ) TYPE: amino acid
        ( D ) TOPOLOGY: linear ( x i ) SEQUENCE DESCRIPTION: SEQ ID NO:16:

```
Ile  Gly  Arg  Pro  Val  Arg  Arg  Cys  Arg  Cys  Arg  Ala  Asn  Cys  Gly  Pro
1                   5                        10                      15

Lys  Glu  Tyr  Ala  Thr  Ala  Phe  Cys  Ala  Gln  Gly  Pro  Phe  Lys  Gln  Phe
                20                       25                      30

Lys  Phe  Cys  Cys  Thr
          35
```

( 2 ) INFORMATION FOR SEQ ID NO:17:

( i ) SEQUENCE CHARACTERISTICS:
        ( A ) LENGTH: 45 amino acids
        ( B ) TYPE: amino acid
        ( D ) TOPOLOGY: linear ( x i ) SEQUENCE DESCRIPTION: SEQ ID NO:17:

```
Ile  Arg  Trp  Pro  Trp  Lys  Arg  Cys  His  Cys  Arg  Ser  Phe  Cys  Arg  Pro
1                   5                        10                      15

Tyr  Glu  Asn  Ala  Thr  Ser  Phe  Cys  Ala  Gln  Gly  Leu  Phe  Lys  Gln  His
```

|    |    | 20  |     |     | 25  |     |     | 30  |     |
|----|----|-----|-----|-----|-----|-----|-----|-----|-----|

Lys Phe Cys Cys Leu Asp Thr Trp Pro Pro Arg Met Lys
         35                  40                 45

(2) INFORMATION FOR SEQ ID NO:18:

(i) SEQUENCE CHARACTERISTICS:
        (A) LENGTH: 39 amino acids
        (B) TYPE: amino acid
        (D) TOPOLOGY: linear (xi) SEQUENCE DESCRIPTION: SEQ ID NO:18:

Thr Ser Gly Ser Gln Ala Arg Ala Thr Cys Tyr Cys Arg Thr Gly Arg
 1               5                   10                  15

Cys Ala Thr Arg Glu Ser Leu Ser Gly Val Cys Glu Ile Ser Gly Arg
             20                  25                  30

Leu Tyr Arg Leu Cys Cys Arg
             35

(2) INFORMATION FOR SEQ ID NO:19:

(i) SEQUENCE CHARACTERISTICS:
        (A) LENGTH: 32 amino acids
        (B) TYPE: amino acid
        (D) TOPOLOGY: linear (xi) SEQUENCE DESCRIPTION: SEQ ID NO:19:

Ala Phe Thr Cys His Cys Arg Arg Ser Cys Tyr Ser Thr Glu Tyr Ser
 1               5                   10                  15

Tyr Gly Thr Cys Thr Val Met Gly Ile Asn His Arg Phe Cys Cys Leu
             20                  25                  30

(2) INFORMATION FOR SEQ ID NO:20:

(i) SEQUENCE CHARACTERISTICS:
        (A) LENGTH: 103 amino acids
        (B) TYPE: amino acid
        (D) TOPOLOGY: linear (xi) SEQUENCE DESCRIPTION: SEQ ID NO:20:

Met Lys Thr Leu Val Leu Leu Ser Ala Leu Val Leu Leu Ala Phe Gln
 1               5                   10                  15

Val Gln Ala Asp Pro Ile Gln Glu Ala Glu Glu Thr Lys Thr Glu
             20                  25                  30

Glu Gln Pro Ala Asp Glu Asp Gln Asp Val Ser Val Ser Phe Glu Gly
             35                  40                  45

Pro Glu Pro Ser Ala Leu Gln Asn Leu Glu Ile Gly Trp Pro Leu Lys
             50                  55                  60

Gln Cys His Cys Arg Lys Phe Cys Arg Pro Tyr Glu Lys Ala Glu Gly
 65                      70                  75                  80

Ser Cys Arg Pro Gly Leu Phe Ile Lys Arg Lys Ile Cys Cys Ile Gln
                 85                  90                  95

Gln Trp Thr Pro Gly Arg Thr
             100

(2) INFORMATION FOR SEQ ID NO:21:

(i) SEQUENCE CHARACTERISTICS:
        (A) LENGTH: 96 amino acids
        (B) TYPE: amino acid
        (D) TOPOLOGY: linear (xi) SEQUENCE DESCRIPTION: SEQ ID NO:21:

```
Met Lys Thr Leu Val Leu Leu Ser Ala Leu Val Leu Val Ala Tyr Gln
1               5                   10                  15

Val Gln Ala Asp Pro Ile Gln Gly Ala Glu Glu Thr Lys Thr Glu
                20              25                  30

Glu Gln Pro Ser Asp Glu Asp Gln Asp Val Ser Val Ser Phe Glu Gly
            35              40                  45

Pro Glu Ala Ser Ala Leu Gln Asp Phe Glu Ile Gly Arg Pro Val Arg
        50              55              60

Arg Cys Arg Cys Arg Ala Asn Cys Gly Pro Lys Glu Tyr Ala Thr Ala
65                  70              75                      80

Phe Cys Ala Gln Gly Pro Phe Lys Gln Phe Lys Arg Phe Cys Cys Thr
                85              90                  95
```

(2) INFORMATION FOR SEQ ID NO:22:

(i) SEQUENCE CHARACTERISTICS:
        (A) LENGTH: 103 amino acids
        (B) TYPE: amino acid
        (D) TOPOLOGY: linear (xi) SEQUENCE DESCRIPTION: SEQ ID NO:22:

```
Met Lys Thr Leu Val Leu Leu Ser Ala Leu Val Leu Leu Ala Phe Gln
1               5                   10                  15

Ile Gln Ala Asp Pro Ile Gln Glu Ala Glu Glu Thr Lys Thr Glu
                20              25                  30

Glu Gln Pro Ala Asp Glu Asp Gln Asp Val Ser Val Ser Phe Glu Gly
            35              40                  45

Pro Glu Pro Ser Ala Leu Gln Asn Leu Glu Ile Arg Trp Pro Trp Lys
        50              55              60

Arg Cys His Cys Arg Ser Phe Cys Arg Pro Tyr Glu Asn Ala Thr Ser
65                  70              75                      80

Phe Cys Ala Gln Gly Leu Phe Lys Gln His Lys Phe Cys Cys Leu Asp
                85              90                  95

Thr Trp Pro Pro Arg Met Lys
                100
```

(2) INFORMATION FOR SEQ ID NO:23:

(i) SEQUENCE CHARACTERISTICS:
        (A) LENGTH: 93 amino acids
        (B) TYPE: amino acid
        (D) TOPOLOGY: linear (xi) SEQUENCE DESCRIPTION: SEQ ID NO:23:

```
Met Lys Thr Leu Val Leu Leu Ser Ala Leu Val Leu Leu Ala Phe Gln
1               5                   10                  15

Val Gln Ala Asp Pro Ile Gln Asn Thr Asp Glu Glu Thr Lys Thr Glu
                20              25                  30

Glu Gln Pro Gly Glu Asp Asp Gln Ala Val Ser Val Ser Phe Gly Asp
            35              40                  45

Pro Glu Gly Thr Ser Leu Gln Glu Glu Ser Leu Arg Asp Leu Val Cys
        50              55              60

Tyr Cys Arg Ser Arg Gly Cys Lys Gly Arg Glu Arg Met Asn Gly Thr
65                  70              75                      80

Cys Arg Lys Gly His Leu Leu Tyr Thr Leu Cys Cys Arg
                85              90
```

(2) INFORMATION FOR SEQ ID NO:24:

(  i  ) SEQUENCE CHARACTERISTICS:
    (  A  ) LENGTH: 93 amino acids
    (  B  ) TYPE: amino acid
    (  D  ) TOPOLOGY: linear (  x i  ) SEQUENCE DESCRIPTION: SEQ ID NO:24:

```
Met Lys Thr Leu Ile Leu Leu Ser Ala Leu Val Leu Leu Ala Phe Gln
1               5                   10                  15
Val Gln Ala Asp Pro Ile Gln Asn Thr Asp Glu Glu Thr Lys Thr Glu
            20              25                  30
Lys Gln Pro Gly Glu Glu Asp Gln Ala Val Ser Val Ser Phe Gly Asp
        35              40                  45
Pro Glu Gly Ser Ser Leu Gln Glu Glu Ser Leu Arg Asp Leu Val Cys
    50              55                      60
Tyr Cys Arg Thr Arg Gly Cys Lys Arg Arg Glu Arg Met Asn Gly Thr
65              70                  75                      80
Cys Arg Lys Gly His Leu Met Tyr Thr Leu Cys Cys Arg
                85                  90
```

(  2  ) INFORMATION FOR SEQ ID NO:25:

(  i  ) SEQUENCE CHARACTERISTICS:
        (  A  ) LENGTH: 93 amino acids
        (  B  ) TYPE: amino acid
        (  D  ) TOPOLOGY: linear (  x i  ) SEQUENCE DESCRIPTION: SEQ ID NO:25:

```
Met Lys Thr Leu Val Leu Leu Ser Ala Leu Val Leu Leu Ala Phe Gln
1               5                   10                  15
Val Gln Ala Asp Pro Ile Gln Asn Thr Asp Glu Glu Thr Lys Thr Glu
            20              25                  30
Glu Gln Pro Gly Glu Asp Asp Gln Ala Val Ser Val Ser Phe Gly Asp
        35              40                  45
Pro Glu Gly Ser Ser Leu Gln Glu Glu Ser Leu Arg Asp Leu Val Cys
    50              55                      60
Tyr Cys Arg Lys Arg Gly Cys Lys Arg Arg Glu Arg Met Asn Gly Thr
65              70                  75                      80
Cys Arg Lys Gly His Leu Met Tyr Thr Leu Cys Cys Arg
                85                  90
```

(  2  ) INFORMATION FOR SEQ ID NO:26:

(  i  ) SEQUENCE CHARACTERISTICS:
        (  A  ) LENGTH: 92 amino acids
        (  B  ) TYPE: amino acid
        (  D  ) TOPOLOGY: linear (  i x  ) FEATURE:
        (  A  ) NAME/KEY: Peptide
        (  B  ) LOCATION: 79
        (  D  ) OTHER INFORMATION: /note= "Xaa = Amino acid is
            independently L or M."

(  i x  ) FEATURE:
        (  A  ) NAME/KEY: Peptide
        (  B  ) LOCATION: 80
        (  D  ) OTHER INFORMATION: /note= "Xaa = Amino acid is
            independently L or M."

(  i x  ) FEATURE:
        (  A  ) NAME/KEY: Peptide
        (  B  ) LOCATION: 82
        (  D  ) OTHER INFORMATION: /note= "Xaa = Amino acid is
            independently L or M."

( x i ) SEQUENCE DESCRIPTION: SEQ ID NO:26:

| Leu | Val | Leu | Leu | Ser | Ala | Leu | Val | Leu | Leu | Ala | Phe | Gln | Val | Gln | Ala |
|---|---|---|---|---|---|---|---|---|---|---|---|---|---|---|---|
| 1 | | | | 5 | | | | | 10 | | | | | 15 | |

| Asp | Pro | Ile | Gln | Asn | Thr | Asp | Glu | Glu | Thr | Lys | Thr | Glu | Glu | Gln | Pro |
|---|---|---|---|---|---|---|---|---|---|---|---|---|---|---|---|
| | | | 20 | | | | | 25 | | | | | 30 | | |

| Gly | Glu | Glu | Asp | Gln | Ala | Val | Ser | Ile | Ser | Phe | Gly | Gly | Gln | Glu | Gly |
|---|---|---|---|---|---|---|---|---|---|---|---|---|---|---|---|
| | | 35 | | | | | 40 | | | | | 45 | | | |

| Ser | Ala | Leu | His | Glu | Lys | Ser | Leu | Arg | Gly | Leu | Leu | Cys | Tyr | Cys | Arg |
|---|---|---|---|---|---|---|---|---|---|---|---|---|---|---|---|
| | 50 | | | | | 55 | | | | | 60 | | | | |

| Lys | Gly | His | Cys | Lys | Arg | Gly | Glu | Arg | Val | Arg | Gly | Thr | Cys | Xaa | Xaa |
|---|---|---|---|---|---|---|---|---|---|---|---|---|---|---|---|
| 65 | | | | | 70 | | | | | 75 | | | | | 80 |

| Gly | Xaa | Ile | Arg | Phe | Leu | Tyr | Cys | Cys | Pro | Arg | Arg |
|---|---|---|---|---|---|---|---|---|---|---|---|
| | | | | 85 | | | | | 90 | | |

( 2 ) INFORMATION FOR SEQ ID NO:27:

( i ) SEQUENCE CHARACTERISTICS:
( A ) LENGTH: 93 amino acids
( B ) TYPE: amino acid
( D ) TOPOLOGY: linear ( x i ) SEQUENCE DESCRIPTION: SEQ ID NO:27:

| Met | Lys | Thr | Phe | Val | Leu | Leu | Ser | Ala | Leu | Val | Leu | Leu | Ala | Phe | Gln |
|---|---|---|---|---|---|---|---|---|---|---|---|---|---|---|---|
| 1 | | | | 5 | | | | | 10 | | | | | 15 | |

| Val | Gln | Ala | Asp | Pro | Ile | His | Lys | Thr | Asp | Glu | Glu | Thr | Asn | Thr | Glu |
|---|---|---|---|---|---|---|---|---|---|---|---|---|---|---|---|
| | | | 20 | | | | | 25 | | | | | 30 | | |

| Glu | Gln | Pro | Gly | Glu | Glu | Asp | Gln | Ala | Val | Ser | Ile | Ser | Phe | Gly | Gly |
|---|---|---|---|---|---|---|---|---|---|---|---|---|---|---|---|
| | | 35 | | | | | 40 | | | | | 45 | | | |

| Gln | Glu | Gly | Ser | Ala | Leu | His | Glu | Glu | Leu | Ser | Lys | Lys | Leu | Ile | Cys |
|---|---|---|---|---|---|---|---|---|---|---|---|---|---|---|---|
| | 50 | | | | | 55 | | | | | 60 | | | | |

| Tyr | Cys | Arg | Ile | Arg | Gly | Cys | Lys | Arg | Arg | Glu | Arg | Val | Phe | Gly | Thr |
|---|---|---|---|---|---|---|---|---|---|---|---|---|---|---|---|
| 65 | | | | | 70 | | | | | 75 | | | | | 80 |

| Cys | Arg | Asn | Leu | Phe | Leu | Thr | Phe | Val | Phe | Cys | Cys | Ser |
|---|---|---|---|---|---|---|---|---|---|---|---|---|
| | | | | 85 | | | | | 90 | | | |

( 2 ) INFORMATION FOR SEQ ID NO:28:

( i ) SEQUENCE CHARACTERISTICS:
( A ) LENGTH: 93 amino acids
( B ) TYPE: amino acid
( D ) TOPOLOGY: linear ( x i ) SEQUENCE DESCRIPTION: SEQ ID NO:28:

| Met | Lys | Thr | Leu | Val | Leu | Leu | Ser | Ala | Leu | Val | Leu | Leu | Ala | Phe | Gln |
|---|---|---|---|---|---|---|---|---|---|---|---|---|---|---|---|
| 1 | | | | 5 | | | | | 10 | | | | | 15 | |

| Val | Gln | Ala | Asp | Pro | Ile | Gln | Asn | Thr | Asp | Glu | Glu | Thr | Lys | Thr | Glu |
|---|---|---|---|---|---|---|---|---|---|---|---|---|---|---|---|
| | | | 20 | | | | | 25 | | | | | 30 | | |

| Glu | Gln | Pro | Gly | Glu | Glu | Asp | Gln | Ala | Val | Ser | Val | Ser | Phe | Gly | Asp |
|---|---|---|---|---|---|---|---|---|---|---|---|---|---|---|---|
| | | 35 | | | | | 40 | | | | | 45 | | | |

| Pro | Glu | Gly | Thr | Ser | Leu | Gln | Glu | Glu | Ser | Leu | Arg | Asp | Leu | Val | Cys |
|---|---|---|---|---|---|---|---|---|---|---|---|---|---|---|---|
| | 50 | | | | | 55 | | | | | 60 | | | | |

| Tyr | Cys | Arg | Ala | Arg | Gly | Cys | Lys | Gly | Arg | Glu | Arg | Met | Asn | Gly | Thr |
|---|---|---|---|---|---|---|---|---|---|---|---|---|---|---|---|
| 65 | | | | | 70 | | | | | 75 | | | | | 80 |

| Cys | Arg | Lys | Gly | His | Leu | Leu | Tyr | Met | Leu | Cys | Cys | Arg |
|---|---|---|---|---|---|---|---|---|---|---|---|---|
| | | | | 85 | | | | | 90 | | | |

( 2 ) INFORMATION FOR SEQ ID NO:29:

( i ) SEQUENCE CHARACTERISTICS:

(A) LENGTH: 93 amino acids
(B) TYPE: amino acid
(D) TOPOLOGY: linear (xi) SEQUENCE DESCRIPTION: SEQ ID NO:29:

| Met | Lys | Thr | Leu | Ile | Leu | Leu | Ser | Ala | Leu | Val | Leu | Leu | Ala | Phe | Gln |
|---|---|---|---|---|---|---|---|---|---|---|---|---|---|---|---|
| 1 | | | | 5 | | | | | 10 | | | | | 15 | |

| Val | Gln | Ala | Asp | Pro | Ile | Gln | Asn | Thr | Asp | Glu | Glu | Thr | Lys | Thr | Glu |
|---|---|---|---|---|---|---|---|---|---|---|---|---|---|---|---|
| | | | 20 | | | | | 25 | | | | | 30 | | |

| Glu | Gln | Pro | Gly | Glu | Asp | Asp | Gln | Ala | Val | Ser | Val | Ser | Phe | Gly | Asp |
|---|---|---|---|---|---|---|---|---|---|---|---|---|---|---|---|
| | | 35 | | | | | 40 | | | | | 45 | | | |

| Pro | Glu | Gly | Ser | Ser | Leu | Gln | Glu | Glu | Ser | Leu | Arg | Asp | Leu | Val | Cys |
|---|---|---|---|---|---|---|---|---|---|---|---|---|---|---|---|
| | 50 | | | | | 55 | | | | | 60 | | | | |

| Tyr | Cys | Arg | Thr | Arg | Gly | Cys | Lys | Arg | Arg | Glu | His | Met | Asn | Gly | Thr |
|---|---|---|---|---|---|---|---|---|---|---|---|---|---|---|---|
| 65 | | | | | 70 | | | | | 75 | | | | | 80 |

| Cys | Arg | Lys | Gly | His | Leu | Met | Tyr | Thr | Leu | Cys | Cys | Arg |
|---|---|---|---|---|---|---|---|---|---|---|---|---|
| | | | | 85 | | | | | 90 | | | |

(2) INFORMATION FOR SEQ ID NO:30:

(i) SEQUENCE CHARACTERISTICS:
(A) LENGTH: 93 amino acids
(B) TYPE: amino acid
(D) TOPOLOGY: linear (xi) SEQUENCE DESCRIPTION: SEQ ID NO:30:

| Met | Lys | Thr | Leu | Val | Leu | Leu | Ser | Ala | Leu | Val | Leu | Leu | Ala | Phe | Gln |
|---|---|---|---|---|---|---|---|---|---|---|---|---|---|---|---|
| 1 | | | | 5 | | | | | 10 | | | | | 15 | |

| Val | Gln | Ala | Asp | Pro | Ile | Gln | Asn | Thr | Asp | Glu | Glu | Thr | Lys | Thr | Glu |
|---|---|---|---|---|---|---|---|---|---|---|---|---|---|---|---|
| | | | 20 | | | | | 25 | | | | | 30 | | |

| Glu | Gln | Pro | Gly | Glu | Glu | Asp | Gln | Ala | Val | Ser | Val | Ser | Phe | Gly | Asp |
|---|---|---|---|---|---|---|---|---|---|---|---|---|---|---|---|
| | | 35 | | | | | 40 | | | | | 45 | | | |

| Pro | Glu | Gly | Ser | Ser | Leu | Gln | Glu | Glu | Ser | Leu | Arg | Asp | Leu | Val | Cys |
|---|---|---|---|---|---|---|---|---|---|---|---|---|---|---|---|
| | 50 | | | | | 55 | | | | | 60 | | | | |

| Tyr | Cys | Arg | Lys | Arg | Gly | Cys | Lys | Arg | Arg | Glu | His | Met | Asn | Gly | Thr |
|---|---|---|---|---|---|---|---|---|---|---|---|---|---|---|---|
| 65 | | | | | 70 | | | | | 75 | | | | | 80 |

| Cys | Arg | Lys | Gly | His | Leu | Leu | Tyr | Met | Leu | Cys | Cys | Arg |
|---|---|---|---|---|---|---|---|---|---|---|---|---|
| | | | | 85 | | | | | 90 | | | |

(2) INFORMATION FOR SEQ ID NO:31:

(i) SEQUENCE CHARACTERISTICS:
(A) LENGTH: 81 amino acids
(B) TYPE: amino acid
(D) TOPOLOGY: linear (xi) SEQUENCE DESCRIPTION: SEQ ID NO:31:

| Leu | Ala | Phe | Gln | Val | Gln | Ala | Asp | Pro | Ile | Gln | Asn | Thr | Asp | Glu | Glu |
|---|---|---|---|---|---|---|---|---|---|---|---|---|---|---|---|
| 1 | | | | 5 | | | | | 10 | | | | | 15 | |

| Thr | Lys | Thr | Glu | Glu | Gln | Pro | Gly | Glu | Asp | Asp | Gln | Ala | Val | Ser | Val |
|---|---|---|---|---|---|---|---|---|---|---|---|---|---|---|---|
| | | | 20 | | | | | 25 | | | | | 30 | | |

| Ser | Phe | Gly | Asp | Pro | Glu | Gly | Ser | Ser | Leu | Gln | Glu | Glu | Ser | Leu | Arg |
|---|---|---|---|---|---|---|---|---|---|---|---|---|---|---|---|
| | | 35 | | | | | 40 | | | | | 45 | | | |

| Asp | Leu | Val | Cys | Tyr | Cys | Arg | Lys | Arg | Gly | Cys | Lys | Arg | Arg | Glu | His |
|---|---|---|---|---|---|---|---|---|---|---|---|---|---|---|---|
| | 50 | | | | | 55 | | | | | 60 | | | | |

| Met | Asn | Gly | Thr | Cys | Arg | Lys | Gly | His | Leu | Met | Tyr | Thr | Leu | Cys | Cys |
|---|---|---|---|---|---|---|---|---|---|---|---|---|---|---|---|
| 65 | | | | | 70 | | | | | 75 | | | | | 80 |

Arg (2) INFORMATION FOR SEQ ID NO:32:

(i) SEQUENCE CHARACTERISTICS:
        (A) LENGTH: 92 amino acids
        (B) TYPE: amino acid
        (D) TOPOLOGY: linear (xi) SEQUENCE DESCRIPTION: SEQ ID NO:32:

```
Lys Thr Leu Val Leu Leu Ser Ala Leu Val Leu Leu Ala Phe Gln Val
 1               5                  10                  15
Gln Ala Asp Pro Ile Gln Asn Thr Asp Glu Glu Thr Lys Thr Glu Glu
             20                  25                  30
Gln Pro Gly Glu Asp Asp Gln Ala Val Ser Val Ser Phe Gly Asp Pro
         35                  40                  45
Glu Gly Ser Ser Leu Gln Glu Glu Ser Leu Arg Asp Leu Val Cys Tyr
     50                  55                  60
Cys Arg Lys Arg Gly Cys Lys Gly Arg Glu Arg Met Asn Gly Thr Cys
 65                  70                  75                  80
Arg Lys Gly His Leu Leu Tyr Thr Leu Cys Cys Arg
                 85                  90
```

(2) INFORMATION FOR SEQ ID NO:33:

(i) SEQUENCE CHARACTERISTICS:
        (A) LENGTH: 85 amino acids
        (B) TYPE: amino acid
        (D) TOPOLOGY: linear (xi) SEQUENCE DESCRIPTION: SEQ ID NO:33:

```
Ala Leu Val Leu Leu Ala Phe Gln Val Gln Ala Asp Pro Ile Gln Asn
 1               5                  10                  15
Thr Asp Glu Glu Thr Lys Thr Glu Glu Gln Pro Gly Glu Glu Asp Gln
             20                  25                  30
Ala Val Ser Val Ser Phe Gly Asp Pro Glu Gly Thr Ser Leu Gln Glu
         35                  40                  45
Glu Ser Leu Arg Asp Leu Val Cys Tyr Cys Arg Ser Arg Gly Cys Lys
     50                  55                  60
Gly Arg Glu Arg Met Asn Gly Thr Cys Arg Lys Gly His Leu Leu Tyr
 65                  70                  75                  80
Met Leu Cys Cys Arg
                 85
```

(2) INFORMATION FOR SEQ ID NO:34:

(i) SEQUENCE CHARACTERISTICS:
        (A) LENGTH: 93 amino acids
        (B) TYPE: amino acid
        (D) TOPOLOGY: linear (xi) SEQUENCE DESCRIPTION: SEQ ID NO:34:

```
Met Lys Thr Leu Ile Leu Leu Ser Ala Leu Val Leu Leu Ala Phe Gln
 1               5                  10                  15
Val Gln Ala Asp Pro Ile Gln Asn Thr Asp Glu Glu Thr Lys Thr Glu
             20                  25                  30
Glu Gln Pro Gly Glu Glu Asp Gln Ala Val Ser Val Ser Phe Gly Asp
         35                  40                  45
Pro Glu Gly Thr Ser Leu Gln Glu Glu Ser Leu Arg Asp Leu Val Cys
     50                  55                  60
Tyr Cys Arg Ala Arg Gly Cys Lys Gly Arg Glu Arg Met Asn Gly Thr
 65                  70                  75                  80
```

```
Cys Arg Lys Gly His Leu Met Tyr Thr Leu Cys Cys Arg
             85                      90
```

( 2 ) INFORMATION FOR SEQ ID NO:35:

( i ) SEQUENCE CHARACTERISTICS:
    ( A ) LENGTH: 93 amino acids
    ( B ) TYPE: amino acid
    ( D ) TOPOLOGY: linear ( x i ) SEQUENCE DESCRIPTION: SEQ ID NO:35:

```
Met Lys Thr Leu Val Leu Leu Ser Ala Leu Val Leu Leu Ala Phe Gln
1               5                   10                  15

Val Gln Ala Asp Pro Ile Gln Asn Thr Asp Glu Glu Thr Lys Thr Glu
            20                  25                  30

Glu Gln Pro Gly Glu Glu Asp Gln Ala Val Ser Val Ser Phe Gly Asp
        35                  40                  45

Pro Glu Gly Thr Ser Leu Gln Glu Glu Ser Leu Arg Asp Leu Val Cys
    50                  55                  60

Tyr Cys Arg Lys Arg Gly Cys Lys Arg Arg Glu His Met Asn Gly Thr
65                  70                  75                  80

Cys Arg Arg Gly His Leu Met Tyr Thr Leu Cys Cys Arg
                85                  90
```

( 2 ) INFORMATION FOR SEQ ID NO:36:

( i ) SEQUENCE CHARACTERISTICS:
    ( A ) LENGTH: 85 amino acids
    ( B ) TYPE: amino acid
    ( D ) TOPOLOGY: linear ( x i ) SEQUENCE DESCRIPTION: SEQ ID NO:36:

```
Ala Leu Val Leu Leu Ala Phe Gln Val Gln Ala Asp Pro Ile Gln Asn
1               5                   10                  15

Thr Asp Glu Glu Thr Lys Thr Glu Glu Gln Pro Gly Glu Glu Asp Gln
            20                  25                  30

Ala Val Ser Val Ser Phe Gly Asp Pro Glu Gly Ser Ser Leu Gln Glu
        35                  40                  45

Glu Ser Leu Arg Asp Leu Val Cys Tyr Cys Arg Thr Arg Gly Cys Lys
    50                  55                  60

Arg Arg Glu Arg Met Asn Gly Thr Cys Arg Lys Gly His Leu Met His
65                  70                  75                  80

Thr Leu Cys Cys Arg
                85
```

( 2 ) INFORMATION FOR SEQ ID NO:37:

( i ) SEQUENCE CHARACTERISTICS:
    ( A ) LENGTH: 93 amino acids
    ( B ) TYPE: amino acid
    ( D ) TOPOLOGY: linear ( x i ) SEQUENCE DESCRIPTION: SEQ ID NO:37:

```
Met Lys Thr Leu Val Leu Leu Ser Ala Leu Val Leu Leu Ala Phe Gln
1               5                   10                  15

Val Gln Ala Asp Pro Ile Gln Asn Thr Asp Glu Glu Thr Lys Thr Glu
            20                  25                  30

Glu Gln Pro Gly Glu Asp Asp Gln Ala Val Ser Val Ser Phe Gly Asp
        35                  40                  45

Pro Glu Gly Ser Ser Leu Gln Glu Glu Ser Leu Arg Asp Leu Val Cys
    50                  55                  60
```

```
            Tyr   Cys   Arg   Lys   Arg   Gly   Cys   Lys   Arg   Arg   Glu   His   Ile   Asn   Gly   Thr
            65                        70                          75                              80

Cys   Arg   Lys   Gly   His   Leu   Leu   Tyr   Met   Leu   Cys   Cys   Arg
                                    85                    90
```

( 2 ) INFORMATION FOR SEQ ID NO:38:

( i ) SEQUENCE CHARACTERISTICS:
        ( A ) LENGTH: 93 amino acids
        ( B ) TYPE: amino acid
        ( D ) TOPOLOGY: linear ( x i ) SEQUENCE DESCRIPTION: SEQ ID NO:38:

```
            Met   Lys   Thr   Leu   Ile   Leu   Leu   Ser   Ala   Leu   Val   Leu   Leu   Ala   Phe   Gln
            1                         5                           10                              15

Val   Gln   Ala   Asp   Pro   Ile   Gln   Asn   Thr   Asp   Glu   Glu   Thr   Lys   Thr   Glu
                                    20                          25                              30

Glu   Gln   Pro   Gly   Glu   Glu   Asp   Gln   Ala   Val   Ser   Val   Ser   Phe   Gly   Asp
                              35                          40                        45

Pro   Glu   Gly   Thr   Ser   Leu   Gln   Glu   Glu   Ser   Leu   Arg   Asp   Leu   Val   Cys
                        50                          55                        60

Tyr   Cys   Arg   Ser   Arg   Gly   Cys   Lys   Gly   Arg   Glu   Arg   Met   Asn   Gly   Thr
            65                        70                          75                              80

Cys   Arg   Lys   Gly   His   Leu   Met   Tyr   Thr   Leu   Cys   Cys   Arg
                                    85                    90
```

( 2 ) INFORMATION FOR SEQ ID NO:39:

( i ) SEQUENCE CHARACTERISTICS:
        ( A ) LENGTH: 82 amino acids
        ( B ) TYPE: amino acid
        ( D ) TOPOLOGY: linear ( x i ) SEQUENCE DESCRIPTION: SEQ ID NO:39:

```
            Leu   Leu   Ala   Phe   Gln   Val   Gln   Ala   Asp   Pro   Ile   Gln   Asn   Thr   Asp   Glu
            1                         5                           10                              15

Glu   Thr   Lys   Thr   Glu   Glu   Gln   Pro   Gly   Glu   Glu   Asp   Gln   Ala   Val   Ser
                                    20                          25                              30

Val   Ser   Phe   Gly   Asp   Pro   Glu   Gly   Thr   Ser   Leu   Gln   Glu   Glu   Ser   Leu
                              35                          40                        45

Arg   Asp   Leu   Val   Cys   Tyr   Cys   Arg   Lys   Arg   Gly   Cys   Lys   Arg   Arg   Glu
                        50                          55                        60

His   Met   Asn   Gly   Thr   Cys   Arg   Lys   Gly   His   Leu   Leu   Tyr   Thr   Leu   Cys
            65                        70                          75                              80

Cys   Arg
```

( 2 ) INFORMATION FOR SEQ ID NO:40:

( i ) SEQUENCE CHARACTERISTICS:
        ( A ) LENGTH: 422 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:40:

```
ACACATTGAG   CTCCTGCTCA   CCAATCCTCC   AGGTGACTCC   CAGCCATGAA   GACACTAGTC        60

CTCCTCTCTG   CCCTTGTCCT   GCTGGCCTTC   CAGGTCCAGG   CTGATCCTAT   CCAAAACACA       120

GATGAAGAGA   CTAAAACTGA   GGAGCAGCCA   GGGGAAGACG   ACCAGGCCGT   ATCTGTCTCC       180

TTTGGAGACC   CAGAAGGCAC   TTCTCTTCAA   GAGGAATCGT   TGAGAGATCT   GGTATGCTAT       240
```

| | | | | | | |
|---|---|---|---|---|---|---|
|TGTAGATCAA|GAGGCTGCAA|AGGAAGAGAA|CGCATGAATG|GGACCTGCAG|AAAGGGTCAT|300|
|TTATTGTACA|CGCTCTGCTG|TCGCTGAACA|TGGAGACCAC|AGAGGACAAG|ACGAACATGA|360|
|GTACTGAGGC|CACTGATGCT|GGTGCCTGAT|GACCACTTCG|CAATAAATTG|TTCGCAATAT|420|
|GC| | | | | |422|

(2) INFORMATION FOR SEQ ID NO:41:

(i) SEQUENCE CHARACTERISTICS:
    (A) LENGTH: 422 base pairs
    (B) TYPE: nucleic acid
    (C) STRANDEDNESS: double
    (D) TOPOLOGY: linear (xi) SEQUENCE DESCRIPTION: SEQ ID NO:41:

| | | | | | | |
|---|---|---|---|---|---|---|
|ACACACTGAG|CCGCTACTCA|CCAATCCTCC|AGGTGACTCC|CAGCCATGAA|GACACTAATC|60|
|CTCCTCTCTG|CCCTCGTCCT|GCTGGCCTTC|CAGGTCCAGG|CTGATCCTAT|CCAAAATACA|120|
|GATGAAGAGA|CTAAAACTGA|GAAGCAGCCA|GGGGAAGAGG|ACCAGGCCGT|ATCTGTCTCC|180|
|TTTGGAGACC|CAGAAGGCTC|TTCTCTTCAA|GAGGAATCGT|TGAGAGATCT|GGTATGCTAT|240|
|TGTAGAACAA|GAGGCTGCAA|AAGAAGAGAA|CGCATGAATG|GGACCTGCAG|AAAGGGTCAT|300|
|TTAATGTACA|CGCTCTGCTG|TCGCTGAACA|TGGAGACCAC|AGAGGACAAG|ATGACCATGA|360|
|GTACTGAGGC|CACTGATGCT|GGTGCCTGAT|GACCACTTCG|CAATAAATTG|CTTGCAATAT|420|
|GC| | | | | |422|

(2) INFORMATION FOR SEQ ID NO:42:

(i) SEQUENCE CHARACTERISTICS:
    (A) LENGTH: 422 base pairs
    (B) TYPE: nucleic acid
    (C) STRANDEDNESS: double
    (D) TOPOLOGY: linear (xi) SEQUENCE DESCRIPTION: SEQ ID NO:42:

| | | | | | | |
|---|---|---|---|---|---|---|
|ACACATTGGG|CTCCTGCTCA|CCAATCCTCC|AGGTGACTCC|CAGCCATGAA|GACACTAGTC|60|
|CTCCTCTCTG|CCCTCGTCCT|GCTGGCCTTC|CAGGTCCAGG|CTGATCCTAT|CCAAAACACA|120|
|GATGAAGAGA|CTAAAACTGA|GGAGCAGCCA|GGGGAAGACG|ACCAGGCCGT|ATCTGTCTCC|180|
|TTTGGAGACC|CAGAAGGCTC|TTCTCTTCAA|GAGGAATCGT|TGAGAGATCT|GGTATGCTAT|240|
|TGTAGAAAAA|GAGGCTGCAA|AAGAAGAGAA|CGCATGAATG|GGACCTGCAG|AAAGGGTCAT|300|
|TTAATGTACA|CACTCTGCTG|TCGCTGAACA|TGGAGACCAC|AGAGGACAAG|ACGAACATGA|360|
|GTACTGAGGC|CACTGATGCT|GGTGCCTGAT|GACCACTTCG|CAATAAATTG|TTCGCAATAT|420|
|GC| | | | | |422|

(2) INFORMATION FOR SEQ ID NO:43:

(i) SEQUENCE CHARACTERISTICS:
    (A) LENGTH: 365 base pairs
    (B) TYPE: nucleic acid
    (C) STRANDEDNESS: double
    (D) TOPOLOGY: linear (xi) SEQUENCE DESCRIPTION: SEQ ID NO:43:

| | | | | | | |
|---|---|---|---|---|---|---|
|ACTAGTCCTC|CTCTCTGCCC|TCGTCCTGCT|GGCCTTCCAG|GTCCAGGCTG|ATCCTATCCA|60|
|AAATACAGAT|GAAGAGACTA|AAACTGAGGA|GCAGCCAGGG|GAAGAGGACC|AGGCCGTATC|120|
|TGTCTCCTTT|GGAGACCCAG|AAGGCTCTGC|TCTTCATGAA|AAATCTTTGA|GAGGTTTGTT|180|

| | | | | | |
|---|---|---|---|---|---|
| ATGCTATTGT | AGAAAAGGAC | ACTGCAAAAG | AGGAGAACGA | GTTCGTGGGA | CTTGTGGAAT | 240
| ACGATTTTTG | TACTGCTGCC | CCCGCCGCTG | AACATGCAGA | TGACAAAGAT | ATGACAACCA | 300
| TTGTCTCTGA | GGCCGCTGAT | GCCGGGGCCT | GATGACCACT | TCTCAAGAAA | TGTTTGCAAT | 360
| ATGCA | | | | | | 365

( 2 ) INFORMATION FOR SEQ ID NO:44:

( i ) SEQUENCE CHARACTERISTICS:
        ( A ) LENGTH: 421 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:44:

| | | | | | |
|---|---|---|---|---|---|
| ACACATTGGG | CTCCTGCTCA | CCAATTCTCC | AGGTGACCCC | CAGCCATGAA | GACATTTGTC | 60
| CTCCTCTCTG | CCCTTGTCCT | GCTGGCCTTC | CAGGTCCAGG | CTGATCCTAT | CCACAAAACA | 120
| GATGAAGAGA | CTAATACTGA | GGAGCAGCCA | GGGGAAGAGG | ACCAGGCCGT | ATCTATCTCC | 180
| TTTGGAGGCC | AAGAAGGGTC | TGCTCTTCAT | GAGGAATTGT | CAAAAAAGCT | GATATGCTAT | 240
| TGTAGAATAA | GAGGCTGCAA | AAGAAGAGAA | CGCGTTTTTG | GGACCTGCAG | AAATCTTTTT | 300
| TTAACTTTCG | TATTCTGCTG | CAGCTGAATA | TGCAGATGAC | AAAGATATGA | CAACCATCAG | 360
| CACTGAGGCC | ACTGATGCTG | GGGTCTGATG | ATCACCTCGC | AATAAATTGT | TCGCAATATG | 420
| C | | | | | | 421

( 2 ) INFORMATION FOR SEQ ID NO:45:

( i ) SEQUENCE CHARACTERISTICS:
        ( A ) LENGTH: 422 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:45:

| | | | | | |
|---|---|---|---|---|---|
| ACACACTGAG | CTGCTACTCA | CCAATCCTCC | AGGTGACTCC | CAGCCATGAA | GACACTAATC | 60
| CTCCTCTCTG | CCCTCGTCCT | GCTGGCCTTC | CAGGTCCAGG | CTGATCCTAT | CCAAAATACA | 120
| GATGAAGAGA | CTAAAACTGA | GGAGCAGCCA | GGGGAAGAGG | ACCAGGCCGT | ATCTGTCTCC | 180
| TTTGGAGACC | CAGAAGGCAC | TTCTCTTCAA | GAGGAATCAT | TGAGATATCT | GGTATGCTAT | 240
| TGTAGAGCAA | GAGGCTGCAA | AGGAAGAGAA | CGCATGAATG | GGACCTGCAG | AAAGGGTCAT | 300
| TTATTGTACA | TGCTCTGCTG | TCGCTGAACA | TGGAGACCTC | AGAGAACAAG | ACGACCATGA | 360
| GTACTGAGGC | CACTGATGCT | GGTGCCTGAT | GACCACTTCG | CAATACATTG | TTCGCAATAT | 420
| GC | | | | | | 422

( 2 ) INFORMATION FOR SEQ ID NO:46:

( i ) SEQUENCE CHARACTERISTICS:
        ( A ) LENGTH: 420 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:46:

| | | | | | |
|---|---|---|---|---|---|
| ACACTGAGCT | GCTACTCACC | AATCCTCCAG | GTGACTCCCA | GCCATGAAGA | CACTAATCCT | 60
| CCTCTCTGCC | CTCGTCCTGC | TGGCCTTCCA | GGTCCAGGCT | GATCCTATCC | AAAACACAGA | 120
| TGAAGAGACT | AAAACTGAGG | AGCAGCCAGG | GGAAGACGAC | CAGGCCGTAT | CTGTCTCCTT | 180
| TGGAGACCCA | GAAGGCTCTT | CTCTTCAAGA | GGAATCGTTG | AGAGATCTGG | TATGCTATTG | 240

```
TAGAACAAGA  GGCTGCAAAA  GAAGAGAACA  CATGAATGGG  ACCTGCAGAA  AGGGTCATTT     300

AATGTACACG  CTCTGCTGTC  GCTGAACATG  GAGACCTCAG  AGAACAAGAC  GACCATGAGT     360

ACTGAGGCCA  CTGATGCTGG  TGCCTGATGA  CCACTTCGCA  ATAAATTGTT  CGCAATATGC     420
```

( 2 ) INFORMATION FOR SEQ ID NO:47:

( i ) SEQUENCE CHARACTERISTICS:
        ( A ) LENGTH: 342 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:47:

```
GCTGGCCTTC  CAGGTCCAGG  CTGATCCTAT  CCAAAACACA  GATGAAGAGA  CTAAAACTGA      60

GGAGCAGCCA  GGGGAAGACG  ACCAGGCCGT  ATCTGTCTCC  TTTGGAGACC  CAGAAGGCTC     120

TTCTCTTCAA  GAGGAATCGT  TGAGAGATCT  GGTATGCTAT  TGTAGAAAAA  GAGGCTGCAA     180

AAGAAGAGAA  CACATGAATG  GGACCTGCAG  AAAGGGTCAT  TTAATGTACA  CGCTCTGCTG     240

TCGCTGAACA  TGGAGACCAC  AGAGGACAAG  ACAAGCATGA  GTACTGAGGC  CACTGATGCT     300

GGTGCCTGAT  GACCACTTCG  CAATAAATTG  TTCGCAATAT  GC                         342
```

( 2 ) INFORMATION FOR SEQ ID NO:48:

( i ) SEQUENCE CHARACTERISTICS:
        ( A ) LENGTH: 377 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:48:

```
ATGAAGACAC  TAGTCCTCCT  CTCTGCCCTC  GTCCTGCTGG  CCTTCCAGGT  CCAGGCTGAT      60

CCTATCCAAA  ACACAGATGA  AGAGACTAAA  ACTGAGGAGC  AGCCAGGGGA  AGAGGACCAG     120

GCCGTATCTG  TCTCCTTTGG  AGACCCAGAA  GGCTCTTCTC  TTCAAGAGGA  ATCGTTGAGA     180

GATCTGGTAT  GCTATTGTAG  AAAAAGAGGC  TGCAAAAGAA  GAGAACACAT  GAATGGGACC     240

TGCAGAAAGG  GTCATTTATT  GTACATGCTC  TGCTGTCGCT  GAACATGGAG  ACCACAGAGG     300

ACAAGATGAA  CATGAGTACT  GAGGCCACTG  ATGCTGGTGC  CTGATGACCA  CTTCGCAATA     360

AATTGTTCGC  AATATGC                                                        377
```

( 2 ) INFORMATION FOR SEQ ID NO:49:

( i ) SEQUENCE CHARACTERISTICS:
        ( A ) LENGTH: 375 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:49:

```
GAAGACACTA  GTCCTCCTCT  CTGCCCTCGT  CCTGCTGGCC  TTCCAGGTCC  AGGCTGATCC      60

TATCCAAAAC  ACAGATGAAG  AGACTAAAAC  TGAGGAGCAG  CCAGGGGAAG  ACGACCAGGC     120

CGTATCTGTC  TCCTTTGGAG  ACCCAGAAGG  CTCTTCTCTT  CAAGAGGAAT  CGTTGAGAGA     180

TCTGGTATGC  TATTGTAGAA  AAAGAGGCTG  CAAAGGAAGA  GAACGCATGA  ATGGAACCTG     240

CAGAAAGGGT  CATTTATTGT  ACACGCTCTG  CTGTCGCTGA  ACATGGAGAC  CACAGAGGAC     300

AAGACGAACA  TGAGTACTGA  GGCCACTGAT  GCTGGTGCCT  GATGACCACT  TCGCAATAAA     360

TTGTTCGCAA  TATGC                                                          375
```

( 2 ) INFORMATION FOR SEQ ID NO:50:

( i ) SEQUENCE CHARACTERISTICS:
        ( A ) LENGTH: 352 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:50:

```
CCCTCGTCCT  GCTGGCCTTC  CAGGTCCAGG  CTGATCCTAT  CCAAAACACA  GATGAAGAGA      60

CTAAAACTGA  GGAGCAGCCA  GGGGAAGAGG  ACCAGGCCGT  ATCTGTCTCC  TTTGGAGACC     120

CAGAAGGCAC  TTCTCTTCAA  GAGGAATCGT  TGAGAGATCT  GGTATGCTAT  TGTAGATCAA     180

GAGGCTGCAA  AGGAAGAGAA  CGCATGAATG  GAACCTGCAG  AAAGGGTCAT  TTATTGTACA     240

TGCTCTGCTG  TCGCTGAACA  TGGAGACCAC  AGAGAACAAG  ACGACCATGA  GTACTGAGGC     300

CACTGATGCT  GGTGCCTGAT  GACCACTTCG  CAATACATTG  TTCGCAATAT  GC             352
```

( 2 ) INFORMATION FOR SEQ ID NO:51:

( i ) SEQUENCE CHARACTERISTICS:
        ( A ) LENGTH: 422 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:51:

```
ACACATTGGG  CTCCTGCTCA  CCAATCCTCC  AGGTGACTCC  CAGCCATGAA  GACACTAGTC      60

CTCCTCTCTG  CCCTCGTCCT  GCTGGCCTTC  CAGGTCCAGG  CTGATCCTAT  CCAAAACACA     120

GATGAAGAGA  CTAAAACTGA  GGAGCAGCCA  GGGGAAGAGG  ACCAGGCCGT  ATCTGTCTCC     180

TTTGGAGACC  CAGAAGGCAC  TTCTCTCCAA  GAGGAATAGT  TGAGAGATCT  GGTATGCTAT     240

TGTAGAGCAA  GAGGCTGCAA  AGGAAGAGAA  CGCATGAATG  GGACCTGCAG  AAAGGGTCAT     300

TTAATGTACA  CGCTCTGCTG  TCGCTGAACA  TGGAGACCTC  AGAGAACAAG  ACGACCATGA     360

GTACTGAGGC  CACTGATGCT  GGTGCCTGAT  GACCACTTCG  CAATAAATTG  TTCGCAATAT     420

GC                                                                         422
```

( 2 ) INFORMATION FOR SEQ ID NO:52:

( i ) SEQUENCE CHARACTERISTICS:
        ( A ) LENGTH: 388 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:52:

```
GACTCCCAGC  CATGAAGACA  CTAGTCCTCC  TCTCTGCCCT  TGTCCTGCTG  GCCTTCCAGG      60

TCCAGGCTGA  TCCTATCCAA  AACACAGATG  AAGAGACTAA  AACTGAGGAG  CAGCCAGGAG     120

AAGAGGACCA  GGCCGTATCT  GTCTCCTTTG  GAGACCCAGA  AGGCACTTCT  CTTCAAGAGG     180

AATCGTTGAG  AGATCTGGTA  TGCTATTGTA  GAAAAGAGG   CTGCAAAAGA  GAGAACACA      240

TGAATGGGAC  CTGCAGAAGG  GGTCATTTAA  TGTACACACT  CTGCTGTCGC  TGAACATGGA     300

GACCACAGAG  GACAAGACGA  ACATGAGTAC  TGAGGCCACT  GATGCTGGTG  CCTGATGACC     360

ACCTCGCAAT  AAATTGTTCG  CAATATGC                                           388
```

( 2 ) INFORMATION FOR SEQ ID NO:53:

( i ) SEQUENCE CHARACTERISTICS:
        ( A ) LENGTH: 352 base pairs (B) TYPE: nucleic acid
(C) STRANDEDNESS: double
(D) TOPOLOGY: linear (xi) SEQUENCE DESCRIPTION: SEQ ID NO:53:

| | | | | | |
|---|---|---|---|---|---|
| CCCTCGTCCT | GCTGGCCTTC | CAGGTCCAGG | CTGATCCTAT | CCAAAACACA | GATGAAGAGA | 60
| CTAAAACTGA | GGAGCAGCCA | GGGGAAGAGG | ACCAGGCCGT | ATCTGTCTCC | TTTGGAGACC | 120
| CAGAAGGCTC | TTCTCTTCAA | GAGGAATCGT | TGAGAGATCT | GGTATGCTAT | TGTAGAACAA | 180
| GAGGCTGCAA | AAGAAGAGAA | CGCATGAATG | GGACCTGCAG | AAAGGGTCAT | TTAATGCACA | 240
| CGCTCTGCTG | TCGCTGAACA | TGGAGACCAC | AGAGGACAAG | ACGAGCATGA | GTACTGAGGC | 300
| CACTGATGCT | GGTGCCTGAT | GACCACTTCG | CAATAAATTG | TTCGCAAAAT | GC | 352

(2) INFORMATION FOR SEQ ID NO:54:

(i) SEQUENCE CHARACTERISTICS:
(A) LENGTH: 401 base pairs
(B) TYPE: nucleic acid
(C) STRANDEDNESS: double
(D) TOPOLOGY: linear (xi) SEQUENCE DESCRIPTION: SEQ ID NO:54:

| | | | | | |
|---|---|---|---|---|---|
| CCAATCCTCC | CAGTGACTCC | CAGCCATGAA | GACACTAGTC | CTCCTCTCTG | CCCTTGTCCT | 60
| GCTGGCCTTC | CAGGTCCAGG | CTGATCCTAT | CCAAAACACA | GATGAAGAGA | CTAAAACTGA | 120
| GGAGCAGCCA | GGGGAAGACG | ACCAGGCCGT | ATCTGTCTCC | TTTGGAGACC | CAGAAGGCTC | 180
| TTCTCTTCAA | GAGGAATCGT | TGAGAGATCT | GGTATGCTAT | TGTAGAAAAA | GAGGCTGCAA | 240
| AAGAAGAGAA | CACATAAATG | GGACCTGCAG | AAAGGGTCAT | TTATTGTACA | CTCTCTGCTG | 300
| TCGCTGAACA | TGGAGACCAC | AGAGGACAAG | ATGACCATGA | GTACTGAGGC | CACTGATGCT | 360
| GGTGCCTGAT | GACCACTCGC | AATAAATTGT | TCGCAATATG | C | | 401

(2) INFORMATION FOR SEQ ID NO:55:

(i) SEQUENCE CHARACTERISTICS:
(A) LENGTH: 391 base pairs
(B) TYPE: nucleic acid
(C) STRANDEDNESS: double
(D) TOPOLOGY: linear (xi) SEQUENCE DESCRIPTION: SEQ ID NO:55:

| | | | | | |
|---|---|---|---|---|---|
| GGTGACTCCC | AGCCATGAAG | ACACTAATCC | TCCTCTCTGC | CCTCGTCCTG | CTGGCCTTCC | 60
| AGGTCCAGGC | TGATCCTATC | CAAAACACAG | ATGAAGAGAC | TAAAACTGAG | GAGCAGCCAG | 120
| GAGAAGAGGA | CCAGGCCGTA | TCTGTCTCCT | TTGGAGACCC | AGAAGGCACT | TCTCTTCAAG | 180
| AGGAATCGTT | GAGAGATCTG | GTATGCTATT | GTAGATCAAG | AGGCTGCAAA | GGAAGAGAAC | 240
| GCATGAATGG | GACCTGCAGA | AAGGGTCATT | TAATGTACAC | GCTCTGCTGT | CGCTGAACAT | 300
| GGAGACCTCA | GAGAACAAGA | CGACCATGAG | TACTGAGGCC | ACTGATGCTG | GTGCCTGATG | 360
| ACCACTTCGC | AATAAATTGT | TCGCAATATG | C | | | 391

(2) INFORMATION FOR SEQ ID NO:56:

(i) SEQUENCE CHARACTERISTICS:
(A) LENGTH: 342 base pairs
(B) TYPE: nucleic acid
(C) STRANDEDNESS: double
(D) TOPOLOGY: linear (xi) SEQUENCE DESCRIPTION: SEQ ID NO:56:

| | | | | | |
|---|---|---|---|---|---|
| GCTGGCCTTC | CAGGTCCAGG | CTGATCCTAT | CCAAAATACA | GATGAAGAGA | CTAAAACTGA | 60

| | | | | | | |
|---|---|---|---|---|---|---|
| GGAGCAGCCA | GGAGAAGAGG | ACCAGGCCGT | ATCTGTCTCC | TTTGGAGACC | CAGAAGGCAC | 120 |
| TTCTCTTCAA | GAGGAATCGT | TGAGAGATCT | GGTATGCTAT | TGTAGAAAAA | GAGGCTGCAA | 180 |
| AAGAAGAGAA | CACATGAATG | GGACCTGCAG | AAAGGGTCAT | TTATTGTACA | CGCTCTGCTG | 240 |
| TCGCTGAACA | TGGAGACCAC | AGAGGACAAG | ATGACCATGA | GTACTGAGGC | CACTGATGCT | 300 |
| GGTGCCTGAT | GACCACCTCG | CAATAAATTG | CTTGCAATAT | GC | | 342 |

(2) INFORMATION FOR SEQ ID NO:57:

(i) SEQUENCE CHARACTERISTICS:
        (A) LENGTH: 403 base pairs
        (B) TYPE: nucleic acid
        (C) STRANDEDNESS: double
        (D) TOPOLOGY: linear (xi) SEQUENCE DESCRIPTION: SEQ ID NO:57:

| | | | | | | |
|---|---|---|---|---|---|---|
| ACACATGGCT | CTCTCACCAA | TCCTCCAGGT | GACTCCCAGC | CATGAAGACA | CTAGTCCTCC | 60 |
| TCTCTGCCTG | TCCTGCTGGC | CTTCCAGGTC | CAGGCTGATC | CTATCCAAAA | CACAGATGAA | 120 |
| GAGACTAAAA | CTGAGGAGCA | GCCAGGGGAA | GAGACCAGGC | TGTGTCTGTC | TCTTTTGGAG | 180 |
| ACCCAGAAGG | CCTTCTCTTC | AAGAGGAATC | GTTGAGAGAT | CTGGTATGCT | ATTGTAGAAA | 240 |
| GAGGCTGCAA | AGAAGAGAAC | CATGAATGGG | ACCTGCAGAA | AGGGTCATTT | ATGTACAGCT | 300 |
| CTGCTGTCGC | TGAACATGGA | GACCCAGAGA | CAAGAACATG | AGTACTGAGG | CCACTGATGC | 360 |
| TGGTGCCTGA | TGACCACTTC | TCAATAAATT | GTTCGCAATA | TGC | | 403 |

(2) INFORMATION FOR SEQ ID NO:58:

(i) SEQUENCE CHARACTERISTICS:
        (A) LENGTH: 419 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 279..286
        (D) OTHER INFORMATION: /note= "N represents DNA that was
            not sequenced."

(xi) SEQUENCE DESCRIPTION: SEQ ID NO:58:

| | | | | | | |
|---|---|---|---|---|---|---|
| TATAAATGCA | GGCTGGATAT | TCACTGTCCA | CACATTGAGC | TCCTGCTCAC | CAATCCTCCA | 60 |
| GGTGACTCCC | AGCCATGAAG | ACACTAGTCC | TCCTCTCTGC | CCTTGTCCTG | CTGGCCTTCC | 120 |
| AGGTCCAGGC | TGATCCTATC | CAAAACACAG | ATGAAGAGAC | TAAAACTGAG | GAGCAGCCAG | 180 |
| GAGAAGAGGA | CCAGGCCGTA | TCTGTCTCCT | TGGAGACCC | AGAAGGCACT | TCTCTTCAAG | 240 |
| AGGAATGTGA | GTACTGGTGT | CCAGAGTGAT | GGATGCTTNN | NNNNNTTTT | GTATCTCCAG | 300 |
| CGTTGAGAGA | TCTGGTATGC | TATTGTAGAT | CAAGAGGCTG | CAAAGGAAGA | GAACGCATGA | 360 |
| ATGGAACCTG | CAGAAAGGGT | CATTTATTGT | ACACGCTCTG | CTGTCGCTGA | ACATGGAGA | 419 |

(2) INFORMATION FOR SEQ ID NO:59:

(i) SEQUENCE CHARACTERISTICS:
        (A) LENGTH: 419 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 279..286
        (D) OTHER INFORMATION: /note= "N represents DNA that was not sequenced."

( x i ) SEQUENCE DESCRIPTION: SEQ ID NO:59:

| | | | | | | |
|---|---|---|---|---|---|---|
| TATAAATGCA | GACTGGCTCC | TCACTCTCCA | CACATTGGGC | TCCTGCTCAC | CAATCCTCCC | 60 |
| AGTGACTCCC | AGCCATGAAG | CCACTTGTCC | TCCTTTCTGC | CCTTGTCCTA | CTGTCCTTTC | 120 |
| AGGTCCAGGC | TGATCCTATC | CAAAACACAG | ATGAAGAGAC | TAAAACTGAG | GAGCAGTCAG | 180 |
| GTGAAGAGGA | CCAGGCTGTG | TCTGTCTCCT | TTGGAGACCG | AGAAGGCGCT | TCTCTTCAAG | 240 |
| AAGAATGTGA | GTACTGGTGC | CCAGTGTGAT | GGATGCTTNN | NNNNNTTTT | GTGTCTCCAG | 300 |
| CGTTGAGAGA | TCTGGTATGC | TATTGTAGAA | CAAGAGGTTG | CAAAAGAAGA | GAACGCATGA | 360 |
| ATGGGACCTG | CAGAAAGGGT | CATTTAATGT | ACACGCTCTG | CTGCCGCTGA | ACATGGAGA | 419 |

( 2 ) INFORMATION FOR SEQ ID NO:60:

( i ) SEQUENCE CHARACTERISTICS:
        ( A ) LENGTH: 419 base pairs
        ( B ) TYPE: nucleic acid
        ( C ) STRANDEDNESS: single
        ( D ) TOPOLOGY: linear ( i x ) FEATURE:
        ( A ) NAME/KEY: misc_feature
        ( B ) LOCATION: 279..286
        ( D ) OTHER INFORMATION: /note= "N represents DNA that was
            not sequenced."

( x i ) SEQUENCE DESCRIPTION: SEQ ID NO:60:

| | | | | | | |
|---|---|---|---|---|---|---|
| TATAAATGCA | GGCTGGATAT | TCACTCTCCA | CACATTGGGC | TCCTGCTCAC | CAATCCTCCA | 60 |
| GGTGACTCCC | AGCCATGAAG | ACACTAGTCC | TCCTCTCTGC | CCTCGTCCTG | CTGGCCTTCC | 120 |
| AGGTCCAGGC | TGATCCTATC | CAAAACACAG | ATGAAGAGAC | TAAAACTGAG | GAGCAGCCAG | 180 |
| GGGAAGACGA | CCAGGCTGTG | TCTGTCTCTT | TTGGAGACCC | AGAAGGCTCT | TCTCTTCAAG | 240 |
| AGGAATGTGA | GTATTGGTGT | CCTGTGTGAT | GGATGCTTNN | NNNNNTTTT | GTGTCTCCAG | 300 |
| CGTTGAGAGA | TCTGGTATGC | TATTGTAGAA | AAAGAGGCTG | CAAAAGAAGA | GAACGCATGA | 360 |
| ATGGGACCTG | CAGAAAGGGT | CATTTAATGT | ACACACTCTG | CTGTCGCTGA | ACATGGAGA | 419 |

( 2 ) INFORMATION FOR SEQ ID NO:61:

( i ) SEQUENCE CHARACTERISTICS:
        ( A ) LENGTH: 419 base pairs
        ( B ) TYPE: nucleic acid
        ( C ) STRANDEDNESS: single
        ( D ) TOPOLOGY: linear ( i x ) FEATURE:
        ( A ) NAME/KEY: misc_feature
        ( B ) LOCATION: 279..286
        ( D ) OTHER INFORMATION: /note= "N represents DNA that was
            not sequenced."

( x i ) SEQUENCE DESCRIPTION: SEQ ID NO:61:

| | | | | | | |
|---|---|---|---|---|---|---|
| TATAAATGCA | AGTTGGCTAC | TCACTCTCCA | CACATTGGGC | TCCTGCTCAC | CAATTCTCCA | 60 |
| GGTGACCCCC | AGCCATGAAG | ACATTTGTCC | TCCTCTCTGC | CCTTGTCCTG | CTGGCCTTCC | 120 |
| AGGTCCAGGC | TGATCCTATC | CACAAAACAG | ATGAAGAGAC | TAATACTGAG | GAGCAGCCAG | 180 |
| GGGAAGAGGA | CCAGGCTGTG | TCAGTCTCCT | TTGGAGGCCA | AGAAGGGTCT | GCTCTTCATG | 240 |
| AAGAATGTGA | GTAGTGGTAC | GCAGTGTGAT | GGATGCTTNN | NNNNNTTTT | GTGTCTCCAG | 300 |
| TGTCAAAAAA | GCTGATATGC | TATTGTAGAA | TAAGAGGCTG | CAAAAGAAGA | GAACGCGTTT | 360 |
| TTGGGACCTG | CAGAAATCTT | TTTTTAACTT | TCGTATTCTG | CTGTAGCTGA | ATATGCAGA | 419 |

( 2 ) INFORMATION FOR SEQ ID NO:62:

( i ) SEQUENCE CHARACTERISTICS:
        ( A ) LENGTH: 419 base pairs
        ( B ) TYPE: nucleic acid
        ( C ) STRANDEDNESS: single
        ( D ) TOPOLOGY: linear ( i x ) FEATURE:
        ( A ) NAME/KEY: misc_feature
        ( B ) LOCATION: 279..286
        ( D ) OTHER INFORMATION: /note= "N represents DNA that was
            not sequenced."

( x i ) SEQUENCE DESCRIPTION: SEQ ID NO:62:

```
TATAAATGCA  GGCTGGATAT  TCACTCTCCA  CACACTGAGC  TGCTACTCAC  CAATCCTCCA     60
GGTGACTCCC  AGCCATGAAG  ACACTAATCC  TCCTCTCTGC  CCTCGTCCTG  CTGGCCTTCC    120
AGGTCCAGGC  TGATCCTATC  CAAAATACAG  ATGAAGAGAC  TAAAACTGAG  GAGCAGCCAG    180
GGGAAGAGGA  CCAGGCTGTG  TCTGTCTCTT  TTGGAGACCC  AGAAGGCACT  TCTCTTCAAG    240
AGGAATGTGA  GTACTGGTGT  CCAGTGTGAT  GGATGCTTNN  NNNNNNTTTT  GTGTCTCCAG    300
CATTGAGAGA  TCTGGTATGC  TATTGTAGAG  CAAGAGGCTG  CAAAGGAAGA  GAACGCATGA    360
ATGGGACCTG  CAGAAAGGGT  CATTTATTGT  ACATGCTCTG  CTGTCGCTGA  ACATGGAGA    419
```

( 2 ) INFORMATION FOR SEQ ID NO:63:

( i ) SEQUENCE CHARACTERISTICS:
        ( A ) LENGTH: 419 base pairs
        ( B ) TYPE: nucleic acid
        ( C ) STRANDEDNESS: single
        ( D ) TOPOLOGY: linear ( i x ) FEATURE:
        ( A ) NAME/KEY: misc_feature
        ( B ) LOCATION: 279..286
        ( D ) OTHER INFORMATION: /note= "N represents DNA that was
            not sequenced."

( x i ) SEQUENCE DESCRIPTION: SEQ ID NO:63:

```
ACTTGAGGGT  AACAGCCTCT  CCCAATTCCA  CACATTGAGC  TCCTGCTCAC  CAATCCTCCA     60
GGTGACTCCC  AGCCATGAAG  ACACTAGTCC  TCCTCTCTGC  CCTTGCCCTG  CTGGCCTTCC    120
AAGTCCAGGC  TGATCCTATC  CAAAACACAG  ATGAAGAGAC  TAAAACTGAG  GAGCAGCCAG    180
GGAAAGAAGA  CCAAGCTGTT  TCTGTCTCCT  TTGGAGACCC  AGAAGGCTCT  TCTCTTCAAG    240
AGGAATGTGA  GTACTGGTGC  CCAGTGTGAT  GGATGCTTNN  NNNNNNTTTT  GTGTCTCCAG    300
CGTTGAGAGA  TCTGATATGA  TATTGTAGAA  CAAGAGGCTG  CAAAAGAAGA  GAACGCCTGA    360
ATGGGACCTG  AAGAAAGGGT  CATTTATTGT  ACATGCTCTG  CTGCTGCTGA  ACATGGAGA    419
```

( 2 ) INFORMATION FOR SEQ ID NO:64:

( i ) SEQUENCE CHARACTERISTICS:
        ( A ) LENGTH: 411 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:64:

```
TATAAATGCA  RRCTGGMTMY  TCACTNTCCA  CACATTGRGC  TCCTGCTCAC  CAATCCTCCA     60
GGTGACTCCC  AGCCATGAAG  ACACTWGTCC  TCCTCTCTGC  CCTYGTCCTG  CTGGCCTTCC    120
AGGTCCAGGC  TGATCCTATC  CAAAAHACAG  ATGAAGAGAC  TAAAACTGAG  GAGCAGCCAG    180
GDGAAGARGA  CCAGGCTGTD  TCTGTCTCYT  TTGGAGACCV  AGAAGGCDCT  TCTCTTCAAG    240
```

```
ARGAATGTGA GTABTGGTGY CCAGTGTGAT GGATGCTTTT TTGTGTCTCC AGCGTTGAGA      300

GATCTGRTAT GCTATTGTAG ADHAAGAGGC TGCAAARGAA GAGAACGCVT GAATGGGACC      360

TGCAGAAAGG GTCATTTAWT GTACANNCTC TGCTGYRGCT GAACATGGAG A               411
```

( 2 ) INFORMATION FOR SEQ ID NO:65:

( i ) SEQUENCE CHARACTERISTICS:
        ( A ) LENGTH: 445 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:65:

```
ACACTGGTCT CCAGCTCACC AATCCTCCAG GTGACTTCCA GCCATGAAGA CTCTTGTCCT       60

CCTCTCTGCC CTTGTCCTGC TGGCATTCCA GGTCCAGGCT GATCCCATTC AAGAGGCAGA      120

AGAAGAGACT AAAACTGAGG AGCAGCCAGC AGATGAGGAC CAGGATGTGT CTGTCTCCTT      180

TGAAGGCCCA GAACCCTCTG CTCTTCAAAA TTTAGAGATA GGATGGCCAT TAAAGCAGTG      240

CCATTGCCGA AAGTTCTGCA GACCTTATGA AAAGGCCGAG GGGTCCTGTC GTCCAGGTCT      300

ATTTATAAAA CGCAAAATCT GCTGCATACA ACAATGGACA CCAGGGAGGA CATAACCACG      360

TGAACTGGGA CCTCACAATC TGTCATTCTT GGGCTTCAAC TCGACTGCTT TTCCTTCTCC      420

AATAAACCCC TTGCAGACAA AAAAA                                           445
```

( 2 ) INFORMATION FOR SEQ ID NO:66:

( i ) SEQUENCE CHARACTERISTICS:
        ( A ) LENGTH: 445 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:66:

```
ACACTGGTCT CCAGCTCACC AATCCTCCAG GTGACTTCCA GCCATGAAGA CTCTTGTCCT       60

CCTCTCTGCC CTTGTCCTGG TGGCCTACCA GGTCCAGGCT GATCCCATTC AAGGGGCAGA      120

AGAAGAGACT AAAACTGAAG AGCAACCATC AGATGAGGAC CAGGATGTGT CTGTCTCCTT      180

TGAAGGCCCA GAAGCCTCTG CTCTTCAAGA TTTTGAGATA GGAAGGCCAG TGAGGAGGTG      240

CCGTTGCAGA GCAAACTGCG GACCTAAAGA ATATGCCACT GCGTTCTGTG CTCAAGGTCC      300

ATTTAAACAG TTCAAATTCT GCTGCACATG AACATGGATC CCAAGTCTGA GATAACCACG      360

TGCTCTGGGA CCTCACAATC TGTCATTATT GTGCTTGACC TCAACTGCTT TTCCTTCTCC      420

AATAAACTCC TGGCAGACAA AAAAA                                           445
```

( 2 ) INFORMATION FOR SEQ ID NO:67:

( i ) SEQUENCE CHARACTERISTICS:
        ( A ) LENGTH: 445 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:67:

```
ACACTGGTCT CCAGCTCACC AATCCTCCAG GTGACTTCCA GCCATGAAGA CTCTTGTCCT       60

CCTCTCTGCC CTTGTCCTGC TGGCATTCCA GATCCAGGCT GATCCCATTC AAGAGGCAGA      120

AGAAGAGACT AAAACTGAGG AGCAGCCAGC AGATGAGGAC CAGGATGTGT CTGTCTCCTT      180

TGAAGGCCCA GAACCCTCTG CTCTTCAAAA TTTAGAGATC AGATGGCCAT GGAAGAGGTG      240
```

| | | | | | |
|---|---|---|---|---|---|
| CCATTGCAGA | AGTTTCTGCA | GACCTTATGA | AAATGCCACT | TCGTTCTGTG | CTCAAGGTCT | 300 |
| ATTTAAACAA | CACAAATTCT | GCTGCCTAGA | AACATGGCCC | CCAAGGATGA | AATAACCACG | 360 |
| TGCTCTGGGA | CCTCACAATC | TGTCATCATT | GTGCTTGGCC | TCAACTTCTT | TTCCTTCTCC | 420 |
| AATAAACTCC | TTGCAGACAA | AAAAA | | | | 445 |

( 2 ) INFORMATION FOR SEQ ID NO:68:

( i ) SEQUENCE CHARACTERISTICS:
        ( A ) LENGTH: 2457 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:68:

| | | | | | |
|---|---|---|---|---|---|
| CCTGAGACCA | ACTCTGTGAT | AATCAGAAAA | GTCAATAATG | TGTCTGAAAT | GTAAGGTGTG | 60 |
| CTTCTTGACT | GATAGTTCTA | AGCCTACAGA | GAGATTCATG | TGGTCATATC | CCATTTAACA | 120 |
| ATGATATATA | TGTTAAATAT | ATAAGATAT | ATGTATGTTC | AGTATGTATG | TTCAATATGT | 180 |
| ATGTAAATAA | TATTCTTGCT | GCTTCACTAG | CTTTTACACA | GAGCTGTAAG | TAAAAACATT | 240 |
| GTAGCCAATG | AATAGTATTT | ATTAACATGT | AAATAGGAGC | TGGCACCTGT | GACAGTGGGA | 300 |
| CTCCATACAC | TGACTGTAAA | CAACAGGATG | CTCTGGACCT | TTTGCTGTGT | GTGTGGTGAG | 360 |
| AGACATGGGA | TAAACACAGA | CTGAAGAGTG | TTCCTGAATG | ACATGGCGGC | ACTTCTCGAG | 420 |
| ACCGGGTAGC | AGCTTCTGAG | CCTCTCTACA | TTGTGGATGT | CCTTTCCTGT | AGGTCAGGTC | 480 |
| TCATTGTCTA | AAAGTAAAAG | CATTGCAGCA | TCTCAGACCT | GGGAAACACC | CCATGGCTTG | 540 |
| AGGGTCCTGA | GCATGAAGAG | CCACCTGGAG | CTCACTCTTG | GCAGATGTGT | TCCATGACTT | 600 |
| TGGCTTCTTC | AGAACAACCC | ACTACAGCTT | CACTCTGACA | AATCCTAGAA | ACTTGAACTC | 660 |
| AATTCACTAG | AGGGCACCAT | AAAGCCATCA | TACCTTATAA | TGGCCCCAAA | GGAGGTGATT | 720 |
| CACAAAGTTT | GCCTTGATGA | GGACAATTGC | TAATACACAA | AAACTTGCAA | AAAAAAATTG | 780 |
| AGTGTCCAGT | CCACCTGGTC | AAGGACTGGT | CCCGGATCCA | CAGTTTCTGA | AATAGCAGG | 840 |
| CTCTAACTTG | AAAACACAAA | AATTGTTTGT | TCTATGAGCT | CATTAAATTA | GGCAGTGTTC | 900 |
| AGCTATTTTC | TTTCCTGACC | ACTGAGAGGT | AAATACTCAA | GCAGATGGGA | AACAGGGGAG | 960 |
| GACAGTAAAG | CCTGTTCATC | ATTATCAGTG | GGAGTGTGCA | TGAGGGGAGG | GGTGTCAGTG | 1020 |
| AACACACAGA | GCATCAGGAA | GGAAGCCTTG | AGGACAGAGG | AACATCAAAG | GGATCCTGAG | 1080 |
| GACAACAGCT | GGGAGCAGTT | GCCATCAATG | AGTGCCTTCT | CTAAGTATGG | GGCATGTTCT | 1140 |
| TTGCCCTATA | AATGCAGGCT | GGCTTCTCTC | TCCACACACT | GGTCTCCAGC | TCACCAATCC | 1200 |
| TCCAGGTGAC | TTCCAGCCAT | GAAGACTCTT | GTCCTCCTCT | CTGCCCTTGT | CCTGCTGGCA | 1260 |
| TTCCAGGTCC | AGGCTGATCC | CATTCAAGAG | GCAGAAGAAG | AGACTAAAAC | TGAGGAGCAG | 1320 |
| CCAGCAGATG | AGGACCAGGA | TGTGTCTGTC | TCCTTTGAAG | GCCCAGAACC | CTCTGCTCTT | 1380 |
| CAAAATTTAG | GTGCGTGCTT | GTGCACAGAA | TGATGGAGGC | TTGGAGTCTC | CTGATGGAGG | 1440 |
| GTTGTAGATT | AGCCCTGGAG | TCCTGTCAAG | GACAGTCTGG | TTCAGGTAGC | TGTCTACTGA | 1500 |
| TCCTTTCAGA | ACTTCCCTGT | CTTATTCATA | GAAATAACAG | TGAGAGACAA | GCCATTGGGC | 1560 |
| TTGACTTTTT | CCTTTTAAGA | TTTCGGTCTA | ACAATTTATC | TGTGAAAAAC | CTTTAAAATA | 1620 |
| TAAAACATAT | TGATTAGTTC | TTTAAACCTG | AGTGATAATT | TTCTTACAGG | AAGAAATATC | 1680 |
| CGTTTTACCC | TAAAAATTAG | ATTGGTACCC | AAATGCCAGT | GTATGAAGGT | GTTGGGTCAA | 1740 |
| GAAAACACAA | AAAAACTGTT | AGAATATGGT | GTAGATGAAA | ATTCCTATAT | GTGATTAACA | 1800 |
| CTTGTTAAAC | ATCTTATCTC | CATGTGTTTG | GGGTTGATCA | CTGTGCTGGC | TGTGATGTCA | 1860 |

-continued

| | | | | | |
|---|---|---|---|---|---|
| CCCACACAGC | AAACCTACTC | TCTACCATGC | ACAGGACATC | TTCATGGGGT | AGTTCACTGT | 1920 |
| TACACACTAC | TGGCCTCCTT | ACTTCATGCC | TGATGCTTTC | TTGTTTCCTC | AGAGATAGGA | 1980 |
| TGGCCATTAA | AGCAGTGCCA | TTGCCGAAAG | TTCTGCAGAC | CTTATGAAAA | GGCCGAGGGG | 2040 |
| TCCTGTCGTC | CAGGTCTATT | TATAAAACGC | AAAATCTGCT | GCATACAACA | ATGGACACCA | 2100 |
| GGGAGGACAT | AACCACGTGA | ACTGGGACCT | CACAATCTGT | CATTCTTGGG | CTTCAACTCG | 2160 |
| ACTGCTTTTC | CTTCTCCAAT | AAACCCCTTG | CAGACAAATA | ACCTGTTTAT | GTTTTTTTGA | 2220 |
| TGCTTTCTAT | GTGGCGTAGA | CAGGACTCTC | CTGAGCCATG | TAGCAAAATC | TTCAGTGAAT | 2280 |
| CCTTTGTAAA | AGAAGTCTTG | GTCACATTTC | AGCAGTCATA | TCAAGGATGA | GCAGGAGGTT | 2340 |
| AGATCCAAAG | AGACAAGATG | GTCTGCGCCA | GCTGCTTCTG | TGTCTATCAA | GTCTTCTGTC | 2400 |
| CTTTAGATTA | GAGTCACCCT | CAAAAATTAG | TTCCAGATTT | TCATGTTCTA | TTTTTTC | 2457 |

( 2 ) INFORMATION FOR SEQ ID NO:69:

( i ) SEQUENCE CHARACTERISTICS:
    ( A ) LENGTH: 2408 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:69:

| | | | | | |
|---|---|---|---|---|---|
| TATTACGAAT | TCGAGCTCGG | TACCGGTATA | TGAAGAGCGA | CCACTGCCAG | GACGAAAGTG | 60 |
| CAATGCGGCA | TACCTCAGTG | GCGTGGAGTG | CAGGTATACA | GATTAATCCG | GCAGCGTCCG | 120 |
| TCGTTGTTGA | TATTGCTTAT | GAAGGCTCCG | GCAGTGGCGA | CTGGCGTACT | GACGGATTCA | 180 |
| TCGTTGGGGT | CGGTTATAAA | TTCTGATTAG | CCAGGTAACA | CAGTGTTATG | ACAGCCCGCC | 240 |
| GGAACCGGTG | GGCTTTTTTG | TGGGGTGAAT | ATGGCAGTAA | AGATTTCAGG | AGTCCTGAAA | 300 |
| GACGGCACAG | GAAAACCGGT | ACAGAACTGC | ACCATTCAGC | TGAAAGCCAG | ACGTAACAGC | 360 |
| ACCACGGTGG | TGGTGAACAC | GGTGGGCTCA | GAGAATCCGG | ATGAAGCCTG | CTTTTTTATA | 420 |
| CTAAGTTGGC | ATTATAAAAA | AGCATTGCTT | ATCAATTTGT | TGCAACGAAC | AGGTCACTAT | 480 |
| CAGTCAAAAT | AAAATCATTA | TTTGATTTCA | ATTTTGTCCC | ACTCCCTGCC | TCTGTCATCA | 540 |
| CGATACTGTG | ATGCCATGGT | GTCCGACTTA | TGCCCGAGAA | GATGTTGAGC | AAACTTATCG | 600 |
| CTTATCTGCT | TCTCATAGAG | TCTTGCAGAC | AAACTGCGCA | ACTCGTGAAA | GGTAGGCGGA | 660 |
| TCTGGGTCGA | CTCTAGGCCT | CACTGGCCTA | ATACGACTCA | CTATAGGGAG | CTCGAGGATC | 720 |
| ATTGCTAATA | CCATGAAACT | TGACCACCTG | GTCAAGGACT | GGTCCAGGGT | CCACAGTTTC | 780 |
| TGAGAAGAGC | AGGCTCCAAC | TTCTAACCAC | AAAAACTATT | TTTTCCATGC | GCTCCTTAAA | 840 |
| TTAGGCAGCG | CCCAGCTATT | TTCTTTCCTG | ACCACTGAGA | GGTAAATACT | CAAGCAGATG | 900 |
| GGAAACAGGG | GAAGATAGCA | AGGCCTCTTC | ATCATTATCA | CTGGGTGTGT | GCGTGAGGGG | 960 |
| AGGGGTGTCA | TTGCATACAC | AGGGCAACAT | CAGGATGGAA | GCCTTGAGGA | CAGAGGAACA | 1020 |
| TCAAAGGGAT | CCTGAGGACA | ACAGCTGGGA | GCAGTTGCCA | TCAGTGAGTG | CCTTCTCTAA | 1080 |
| GTGTGGGGCC | TTTCTCTGCC | ACATAAATGC | AGGCTGCCTC | CTCTCTCCAC | ACACTGGTCT | 1140 |
| CCAGCTCACC | AATCCTCCAG | GTGACTTCCA | GCCATGAAGA | CTCTTGTCCT | CCTCTCTGCC | 1200 |
| CTTGTCCTGG | TGGCCTACCA | GGTCCAGGCT | GATCCCATTC | AAGGGCAGA | AGAAGAGACT | 1260 |
| AAAACTGAAG | AGCAACCATC | AGATGAGGAC | CAGGATGTGT | CTGTCTCCTT | TGAAGGCCCA | 1320 |
| GAAGCCTCTG | CTCTTCAAGA | TTTTGGTGAG | TGCTTATGCA | CAGAATGATG | GAGGCTTGGA | 1380 |
| GTCTCCTGAT | GGAGGGTTGT | AGATTAGACC | TGGAATCCTG | TCAAGAACTG | TCTGGTTCAG | 1440 |

| | | | | | | |
|---|---|---|---|---|---|---|
| GTAGCTGTCT | CTTGGTCCCT | TTACATTCCT | TGTCTTCTTC | ATAGAAGTAA | CGGAGAGAGA | 1500 |
| TTAACCATTG | GGCTTGACTT | TTTTCCTTTT | AAAATTTTG | ATCTAACAAT | TTATCTGTGG | 1560 |
| AAAACCTTTA | AAATATAAAA | CATATTGATT | AGTTCTTTTA | GACCTGATTG | ATAATTTTGT | 1620 |
| TATAAGAAGA | AATATTCGTT | CTACTTTAAA | AATTAGATTT | GGGACCCAAA | TGCCAGTGTA | 1680 |
| TGAAGCTGTT | GGGTAAGGAA | AAACCAAAAA | TGGTGATAGA | ATGTTGTGTA | GATGACAATT | 1740 |
| CCTTTATGCG | ATTAACACTT | TTTAAAATGT | CTTATCTCCA | TGTGTTTGGG | GTTGATCATG | 1800 |
| GTGCTGACTG | TGATGTCACC | CACAGAGCAA | ACCTACTCTC | TACCATGCAC | AGGACATCTT | 1860 |
| CATAGGGTAG | TTCACTGTCA | CACACTGCTG | GCCTCGTTAC | TTCATGCCTG | ATGCTTTCTT | 1920 |
| GTTTCCTCAG | AGATAGGAAG | GCCAGTGAGG | AGGTGCCGTT | GCAGAGCAAA | CTGCGGACCT | 1980 |
| AAAGAATATG | CCACTGCGTT | CTGTGCTCAA | GGTCCATTTA | AACAGTTCAA | ATTCTGCTGC | 2040 |
| ACATGAACAT | GGATCCCAAG | TCTGAGATAA | CCACGTGCTC | TGGGACCTCA | CAATCTGTCA | 2100 |
| TTATTGTGCT | TGACCTCAAC | TGCTTTTCCT | TCTCCAATAA | ACTCCTGGCA | GACAAATAAT | 2160 |
| CGGTATATGT | TTATTTGATG | CTTTCTATTT | GGCTTAGACA | GAACTCTCCT | GAGCCATGTA | 2220 |
| GCTGAATCTT | CAGTGAATCC | TTTGTAAAGG | TCACATTTCA | GCAGTCATAT | CAAGGATGAG | 2280 |
| CAGGAGGTTA | GATACAAAGA | GACAAGATGG | TCTGCGCCAG | CTGCTTCTTT | GTCTATCAAG | 2340 |
| TCTGCTTTCC | TTTAGATTAG | AGTCACCATC | AAAAATTATT | CCCACATTTT | CATGTTCTAT | 2400 |
| ATTTTTTT | | | | | | 2408 |

( 2 ) INFORMATION FOR SEQ ID NO:70:

( i ) SEQUENCE CHARACTERISTICS:
        ( A ) LENGTH: 2551 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:70:

| | | | | | | |
|---|---|---|---|---|---|---|
| CCTGAGACCA | ACTCTGTGAT | AATCAGAAAA | GACAATTATG | TGTCTTAAAT | GTAAGGTTTG | 60 |
| CTTCTTGACT | GATAGATCTA | ACCCTACAGA | GAGATTCAAG | TGGTCTTGTC | CCATTGAACA | 120 |
| ATAGTATATA | TGTTTTATAT | ATATATATAT | ATATATGTAT | ATGTATATAT | ATATGTGTGT | 180 |
| GTGTGTGTGT | GTGTGTCTGT | GTCTGTGTGT | CTGTGTGTCT | GTGTGTCTGT | GTGTCTGTGT | 240 |
| GTGTATGTGT | GTGTATGTGT | ACATATGTTC | AATATGTCTG | TAAAATAGTA | TTCTTGTAGC | 300 |
| TTCACTTACT | TTTGCACAGA | GCTGTAAATA | AGAACATTGT | AGCCAATGAA | TAGTATTTAT | 360 |
| TAACATGTAA | ATAGGAGCTG | GCACCTCTGA | CAGTGGGACT | CCATACAGTG | ACTGTAAACA | 420 |
| ACAGGATGCT | CTAGACCTTT | TGCTGTGTGT | GTGGTGAGAG | ACATGGGATA | AACACAGACT | 480 |
| GAAGTGTATG | ACATGGCGGC | ACTTCTCGAG | ACCGGGTAGC | AGCTTCTGAG | CCTCTCTACA | 540 |
| TTGTGGATGT | CCTTTCCTGT | AGGTCAGGTC | TCATTGTCTA | AAAGTAAAAG | CATTGCAGCA | 600 |
| TCTCAGACCT | GGGAAACACC | CCATGGCTTG | AGGGTCCCGC | AGGTGAAGAG | CCACCTGGAG | 660 |
| CTCACTCTTG | GCAGATGTGT | TCCATGACTT | TGGCTTCTTC | AGAACCACCC | ACTACAGCTT | 720 |
| CACTCTGACA | AATCTTAGAA | ACTTGAACTC | AATTCACTGG | AGGGCACAAT | AAAGCCATCT | 780 |
| TACTTTCTCT | AAAATGGCCC | CAAAGGAGGG | GATTCACAAA | GTTTGCCTTG | ATGAGGACCA | 840 |
| TTGCTAATAC | CCCAAAACTT | GCAAAAAAAA | TTGAGTGTCC | AGTCAACCTG | GTCAAGGACT | 900 |
| GGTCCTGGAT | CCACAGTTTC | TGAGAAAAGA | AGGCTCCAAC | TTCAAAACAC | AAACCACTCC | 960 |
| TGTTCTATGC | GCTCATTAAA | TTAGGCAGTG | TTAAGCTATT | TTCTTTCCTG | ACCACTGAGA | 1020 |
| GGTAAATACT | CAAGCAGATG | GGAAACAGGG | GAGGACAGCA | AAGCCTGTTC | ATCATTATCA | 1080 |

| | | | | | | |
|---|---|---|---|---|---|---|
|GTGGGAGTGT|GCGTGAGGGG|AGGGGTGTCA|GTGAACACAC|AGAGCATCAG|GAAGGAAGCC|1140|
|TTGAGGACAG|AGGAACATCA|AAGGGATCCT|GAGGACAACA|GCTGGGAGCA|GTTGGCATCA|1200|
|CTGAGTGCCG|TCTCTAAGTG|TGGGGCCTTT|CTCTGCCACA|TAAATGCAGG|CTGGCTCCTC|1260|
|TCTCCACACA|CTGGTCTCCA|GCTCACCAAT|CCTCCAGGTG|ACTTCCAGCC|ATGAAGACTC|1320|
|TTGTCCTCCT|CTCTGCCCTT|GTCCTGCTGG|CATTCCAGAT|CCAGGCTGAT|CCCATTCAAG|1380|
|AGGCAGAAGA|AGAGACTAAA|ACTGAGGAGC|AGCCAGCAGA|TGAGGACCAG|GATGTGTCTG|1440|
|TCTCCTTTGA|AGGCCCAGAA|CCCTCTGCTC|TTCAAAATTT|AGGTGCGTGC|TTGTGCACAG|1500|
|AATGATGGAG|GCTTGGAGTC|TCCTGATGGA|GGGTTGTAGA|TTAGCCCTGG|AGTCCTGTCA|1560|
|AGGACAGTCT|GGTTCAGGTA|GCTGTCTATT|GATCCTTTCA|GAACTTCCCT|GTCTTATTCA|1620|
|TAGAAATAAC|AGTGAGAGAC|AAGCCATTGG|GCTTGACTTT|TTCCTTTTAA|GATTTTGGTC|1680|
|TAACAATTTA|TCTGTGAAAA|ACCTTTAAAA|TATAAAACAT|ATTGATTAGT|TCTTTTAAAC|1740|
|CTGATTGATA|ATTTTGTTAT|AGGAAGAAAT|AACTGTTCTA|CTTTAAAAAT|TAGATTTGGT|1800|
|ACCTAAATGC|CAGTGTATTA|AGGTGTTGGG|TCAGGAAAAC|ACAATAATGC|TGATAGAATG|1860|
|TGGTGTAGAT|GACAATTCCT|ATATGCGATT|AACACTTGTT|AAATTGTCCT|ATCTCCATGT|1920|
|GTTTGGGGTT|GATCATGGTG|CTGGCTGTGA|TGTCACCCAC|ACAGCAAACC|TACTTTCTAC|1980|
|CATGCACAGG|ACATCTTCAT|AGGGTAGTTC|ACTGTCACAC|ACTGCTGGCC|TCCTTACTTC|2040|
|ATGCCTGATG|CTTTCTCGTT|TCCTCAGAGA|TCAGATGGCC|ATGGAAGAGG|TGCCATTGCA|2100|
|GAAGTTTCTG|CAGACCTTAT|GAAAATGCCA|CTTCGTTCTG|TGCTCAAGGT|CTATTTAAAC|2160|
|AACACAAATT|CTGCTGCCTA|GAAACATGGC|CCCCAAGGAT|GAAATAACCA|CGTGCTCTGG|2220|
|GACCTCACAA|TCTGTCATCA|TTGTGCTTGG|CCTCAACTTC|TTTTCCTTCT|CCAATAAACT|2280|
|CCTTGCAGAC|AAATAACCTG|TTTATGTTTT|TTTGATGCTT|TCTATGTGGC|TTAGACAGGG|2340|
|CTCTCCTGAG|CCATGTAGCA|GAATCTTCAG|TGAATCCTTT|GTAAAGAAG|TCTTGGTCAC|2400|
|ATTTCAACAG|TCATATCAAG|GATGAGCAGG|AGGTTAGATC|CAAAGAGACA|AGATGCTCTG|2460|
|CTCCAGCTGC|TTCTTGACTA|TCAAGTCTTC|TGTCCTTCAG|ATTAGAGTCA|CCCTCAAAAA|2520|
|TTAGTCCCAC|CTTTTCATGT|TCTATTTTTT|T| | |2551|